United States Patent
Butler et al.

(10) Patent No.: US 12,233,067 B2
(45) Date of Patent: *Feb. 25, 2025

(54) TOPICAL TREATMENT OF VITILIGO BY A JAK INHIBITOR

(71) Applicant: Incyte Corporation, Wilmington, DE (US)

(72) Inventors: Kathleen Butler, Wilmington, DE (US); Jim Lee, Devon, PA (US); Kang Sun, Wallingford, PA (US); Fiona Kuo, West Chester, PA (US); Michael Howell, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 48 days.

This patent is subject to a terminal disclaimer.

(21) Appl. No.: 18/077,315

(22) Filed: Dec. 8, 2022

(65) Prior Publication Data

US 2023/0355628 A1   Nov. 9, 2023

Related U.S. Application Data

(63) Continuation of application No. 16/897,923, filed on Jun. 10, 2020, now Pat. No. 11,602,536.

(60) Provisional application No. 62/967,879, filed on Jan. 30, 2020, provisional application No. 62/911,845, filed on Oct. 7, 2019, provisional application No. 62/894,496, filed on Aug. 30, 2019, provisional application No. 62/894,581, filed on Aug. 30, 2019, provisional application No. 62/894,541, filed on Aug. 30, 2019, provisional application No. 62/894,564, filed on Aug. 30, 2019, provisional application No. 62/894,514, filed on Aug. 30, 2019, provisional application No. 62/859,506, filed on Jun. 10, 2019, provisional application No. 62/859,601, filed on Jun. 10, 2019, provisional application No. 62/859,495, filed on Jun. 10, 2019, provisional application No. 62/859,584, filed on Jun. 10, 2019, provisional application No. 62/859,532, filed on Jun. 10, 2019.

(51) Int. Cl.
| | |
|---|---|
| *A61K 31/519* | (2006.01) |
| *A61P 17/00* | (2006.01) |
| *A61K 9/00* | (2006.01) |
| *A61K 9/06* | (2006.01) |
| *A61K 9/107* | (2006.01) |

(52) U.S. Cl.
CPC ............ *A61K 31/519* (2013.01); *A61P 17/00* (2018.01); *A61K 9/0014* (2013.01); *A61K 9/06* (2013.01); *A61K 9/107* (2013.01)

(58) Field of Classification Search
CPC .................................................. A61K 31/519
See application file for complete search history.

(56) References Cited

U.S. PATENT DOCUMENTS

| | | |
|---|---|---|
| 5,521,184 A | 5/1996 | Zimmerman |
| 7,598,257 B2 | 10/2009 | Rodgers et al. |
| 8,415,362 B2 | 4/2013 | Rodgers et al. |
| 8,722,693 B2 | 5/2014 | Rodgers et al. |
| 8,822,481 B1 | 9/2014 | Rodgers et al. |
| 9,079,912 B2 | 7/2015 | Rodgers et al. |
| 9,974,790 B2 | 5/2018 | Rodgers et al. |
| 10,610,530 B2 | 4/2020 | Li et al. |
| 10,639,310 B2 | 5/2020 | Rodgers et al. |
| 10,758,543 B2 | 9/2020 | Parikh et al. |
| 10,869,870 B2 | 12/2020 | Parikh et al. |
| 11,219,624 B2 | 1/2022 | Parikh et al. |
| 11,602,536 B2 * | 3/2023 | Butler ................... A61P 37/00 |
| 2008/0312259 A1 | 12/2008 | Rodgers |
| 2015/0250790 A1 | 9/2015 | Parikh et al. |
| 2019/0060311 A1 | 2/2019 | Shanler et al. |
| 2019/0125750 A1 | 5/2019 | Rodgers et al. |
| 2020/0069965 A1 | 3/2020 | King et al. |
| 2020/0211707 A1 | 7/2020 | Chen et al. |
| 2021/0030672 A1 | 2/2021 | Butler et al. |
| 2022/0211712 A1 | 7/2022 | Parikh et al. |

FOREIGN PATENT DOCUMENTS

| | | |
|---|---|---|
| WO | 2000/009495 A1 | 2/2000 |
| WO | 2000/053595 A1 | 9/2000 |
| WO | 2001/014402 A1 | 3/2001 |
| WO | 2001/064655 A1 | 9/2001 |
| WO | 2003/024967 A1 | 3/2003 |
| WO | 2003/037347 A1 | 5/2003 |
| WO | 2003/099771 A1 | 12/2003 |
| WO | 2004/005281 A1 | 1/2004 |
| WO | 2004/026406 A1 | 4/2004 |
| WO | 2004/046120 A1 | 6/2004 |
| WO | 2004/056786 A1 | 7/2004 |
| WO | 2004/080980 A1 | 9/2004 |
| WO | 2005/028444 A1 | 3/2005 |
| WO | 2006/056399 A1 | 6/2006 |
| WO | 2018/087202 A1 | 5/2018 |

(Continued)

OTHER PUBLICATIONS

A Study of INCB018424 Phosphate Cream in Subjects With Vitiligo NCT03099304, Version 19: Mar. 25, 2019.
European Search Report for European Application No. 20823024.3, dated Jul. 18, 2023.
Rothstein Brooke et al: "Treatment of vitiligo with the topical Janus kinase inhibitor ruxolitinib", Journal of the American Academy of Dermatology, Mosby, Inc, US, vol. 76, No. 6, Apr. 5, 2017 (Apr. 5, 2017), pp. 1054-1060.e1, XP085024421, ISSN: 0190-9622, DOI: 10.1016/J.JAAD.2017.02.049.
Rosmarin David et al., "Ruxolitinib cream for treatment of vitiligo: a randomized, controlled, phase 2 trial," The Lancet, Elsevier, Amsterdam, NL, vol. 396, No. 10244, Jul. 9, 2020 (Jul. 9, 2020), pp. 110-120, XP086211925.

(Continued)

*Primary Examiner* — Paul V Ward
(74) *Attorney, Agent, or Firm* — Finnegan, Henderson, Farabow, Garrett & Dunner, LLP

(57) ABSTRACT

The present disclosure relates to topical treatment of vitiligo using ruxolitinib, or a pharmaceutically acceptable salt thereof.

15 Claims, 64 Drawing Sheets

(56) References Cited

FOREIGN PATENT DOCUMENTS

| WO | 2018/200786 A1 | 11/2018 |
| WO | 2019/040706 A1 | 2/2019 |
| WO | 2020/252012 A1 | 12/2020 |

OTHER PUBLICATIONS

Diqin Yan et al., "The efficacy and safety of JAK inhibitors for alopecia areata: A systematic review and meta-analysis of prospective studies," Systemic Review, Aug. 24, 2022, pp. 1-13.

Investor and Analyst Event, "Building Value through Innovative Medicines," Jun. 21, 2018, 108 pages.

Joshipura, et al., JAM ACAD Dermatol, "Treatment of vitiligo with the topical Janus kinase inhibitor ruxolitinib: A 32-week open-label extension study with optional narrow-band ultraviolet B," Jun. 2018, 4 pages.

Craig low BG, King BA. Tofacitinib citrate for the treatment of vitiligo: a pathogenesis-directed Therapy. JAMA Dermatol 2015; 151:1110-1112.

Frisoli ML, Harris JE. Vitiligo: mechanistic insights lead to novel treatments. J Allergy Clin Immunol 2017; 140:654-662.

The Ultimate Guide to pH and Your Skin, Paula's Choice, publication date (acquired from the source code of the webpage): Nov. 15, 2018 (Year: 2018).

* cited by examiner

Mean and Standard Error of Change from Baseline in T-VASI Score by Visit and Treatment Group (Population: Intent-to-Treat Subjects; Double-Blind Period)-Head and Neck only Mean and Standard Error of Change from Baseline in T-VASI Score by Visit and Treatment Group (Population: Intent-to-Treat Subjects: Double-Blind Period)-Head and Neck only Mean and Standard Error of Change from Baseline in T-VASI Score by Visit and Treatment Group
(Population: Intent-to-Treat Subjects: Double-Blind Period)-Hands only FIG. 44 Proportion of Subjects Achieving T-VASI25 Response by Visit and Treatment Group up to Week 52 (Population: Intent-to-Treat Subjects: Double-Blind Period-Lower Extremities Only)

Proportion of Subjects Achieving T-VASI25 Response by Visit and Treatment Group up to Week 52
(Population: Intent-to-Treat Subjects; Double-Blind Period-Feet Only)

FIG. 53

P-Values from Fisher Exact Test between Combined Group and Vehicle Group at Week 24:

|  | Head | Hands | Upper | Trunk | Lower | Feet |
|---|---|---|---|---|---|---|
| T-VAS125 | 0.0147 | 0.0307 | 0.0079 | 0.1236 | 0.0127 | 0.0279 |
| T-VAS150 | 0.0046 | 0.4382 | 0.0957 | 0.0549 | 0.0151 | 0.1027 |
| T-VAS175 | 0.0085 | 0.5684 | 0.0545 | 0.3162 | 0.1815 | 0.1831 |

FIG. 59

| PARAMETER, N (%) | WEEK 24 | | | | WEEK 52 | | |
|---|---|---|---|---|---|---|---|
| | VEHICLE BID (N=31) | 0.15% QD (N=31) | RUXOLITINIB CREAM 0.5% QD (N=31) | 1.5% QD (N=31) | 0.5% QD (N=31) | 1.5% QD (N=30) | 1.5% BID (N=33) |
| PATIENTS WITH TEAE MOST COMMON TEAEs* | 20 (62.5) | 20 (64.5) | 26 (83.9) | | | 23 (76.7) | 23 (69.7) |
| ACNE | 1 (3.1) | 4 (12.9) | 5 (16.1) | | | 3 (10.0) | 6 (18.2) |
| VIRAL UPPER RESPIRATORY TRACT INFECTION | 5 (15.6) | 3 (9.7) | 3 (9.7) | | | 6 (20.0) | 1 (3.0) |
| APPLICATION SITE PRURITUS | 3 (9.4) | 6 (19.4) | 3 (9.7) | | | 3 (10.0) | 1 (3.0) |
| PRURITUS | 3 (9.4) | 1 (3.2) | 5 (16.1) | | | 4 (13.3) | 3 (9.1) |
| UPPER RESPIRATORY TRACT INFECTION HEADACHE | 0 | 1 (3.2) | 5 (16.1) | | | 1 (3.3) | 3 (9.1) |
| SINUSITIS | 3 (9.4) | 1 (3.2) | 0 | | | 3 (10.0) | 2 (6.1) |
| | 1 (3.1) | 2 (6.5) | 1 (3.2) | | | 2 (6.7) | 2 (6.1) |
| PATIENTS WITH TREATMENT-RELATED TEAE MOST COMMON TREATMENT-RELATED TEAEs* | 12 (37.5) | 11 (35.5) | 12 (38.7) | | | 12 (40.0) | 10 (30.3) |
| APPLICATION SITE PRURITUS | 3 (9.4) | 6 (19.4) | 3 (9.7) | | | 3 (10.0) | 1 (3.0) |
| ACNE | 1 (3.1) | 1 (3.2) | 3 (9.7) | | | 3 (10.0) | 6 (18.2) |
| PRURITUS | 2 (6.3) | 1 (3.2) | 4 (12.9) | | | 3 (10.0) | 2 (6.1) |
| | 1 (3.1) | 1 (3.2)‡ | 0 | | | 1 (3.3) | 0 |
| PATIENTS WITH TEAE LEADING TO DISCONTINUATION† | 0 | 0 | 2 (6.5) | | | 1 (3.3) | 1 (3.0) |
| PATIENTS WITH SERIOUS TEAEs§ | | | | | | | |

BID, TWICE DAILY; QD, ONCE DAILY; TEAE, TREATMENT-EMERGENT ADVERSE EVENT.
* OCCURIG IN >5% OF THE TOTAL PATIENT POPULATION.
† TEAEs LEADING TO DISCONTINUATION WERE NOT RELATED TO TREATMENT UNLESS OTHERWISE INDICATED.
‡ HEADACHE RELATED TO TREATMENT.
§ NO SERIOUS TEAEs WERE RELATED TO TREATMENT.

TOPICAL TREATMENT OF VITILIGO BY A JAK INHIBITOR

CROSS-REFERENCE TO RELATED APPLICATIONS

This is a continuation of U.S. application Ser. No. 16/897,923, filed Jun. 10, 2020, now U.S. Pat. No. 11,602,536, issued on Mar. 14, 2023, which claims priority to U.S. Provisional Application No. 62/859,584, filed Jun. 10, 2019, U.S. Provisional Application No. 62/894,564, filed Aug. 30, 2019, U.S. Provisional Application No. 62/911,845, filed Oct. 7, 2019, U.S. Provisional Application No. 62/967,879, filed Jan. 30, 2020, U.S. Provisional Application No. 62/859,601, filed Jun. 10, 2019, U.S. Provisional Application No. 62/894,514, filed Aug. 30, 2019, U.S. Provisional Application No. 62/859,495, filed Jun. 10, 2019, U.S. Provisional Application No. 62/894,581, filed Aug. 30, 2019, U.S. Provisional Application No. 62/859,506, filed Jun. 10, 2019, U.S. Provisional Application No. 62/894,496, filed Aug. 30, 2019, U.S. Provisional Application No. 62/859,532, filed Jun. 10, 2019, and U.S. Provisional Application No. 62/894,541, filed Aug. 30, 2019, each of which is incorporated herein by reference in its entirety.

TECHNICAL FIELD

The present disclosure relates to topical treatment of vitiligo using ruxolitinib, or a pharmaceutically acceptable salt thereof.

BACKGROUND

Vitiligo occurs when the cells that produce melanin die or stop functioning, resulting in patchy loss of skin pigmentation. Nonsegmental vitiligo involves depigmentation in patches of skin all over the body. Depigmentation typically occurs on the face, neck, and scalp, and around body openings. Loss of pigmentation is also frequently seen in areas that tend to experience rubbing, impact, or other trauma, such as the hands, and arms. Segmental vitiligo is associated with smaller patches of depigmented skin that appear on one side of the body in a limited area.

Vitiligo is estimated to affect 0.5% to 2% of the population worldwide (Krüger C, Schallreuter K U. A review of the worldwide prevalence of vitiligo in children/adolescents and adults. Int J Dermatol 2012; 51:1206-1212). The prevalence is similar between men and women, and there is no known difference in presentation according to skin type or race. Almost 50% of patients present before 20 years of age, and many of them present before 10 years of age (Rodrigues M, Ezzedine K, Hamzavi I, Pandya A G, Harris J E, Vitiligo Working Group. New discoveries in the pathogenesis and classification of vitiligo. J Am Acad Dermatol 2017; 77:1-13). Generalized (nonsegmental) vitiligo is the most common type, accounting for up to 90% of cases (Taieb A, Picardo M. Clinical practice. Vitiligo. N Engl J Med 2009; 360:160-169). Vitiligo is associated with autoimmune diseases such as Sutton nevus, thyroid disorders, juvenile diabetes mellitus, pernicious anemia, and Addison's disease. The natural course of the disease is generally unpredictable, but it is often progressive. Some degree of spontaneous repigmentation may occur in 10% to 20% of patients; however, it is typically not cosmetically acceptable (Castanet J, Ortonne J P. Pathophysiology of vitiligo. Clin Dermatol 1997:15:845-851).

Vitiligo is a serious disease owing to its substantial psychological impact on patients' day-to-day functioning, and its progressive course if left untreated. Studies have shown that the effect vitiligo has on quality of life, particularly psychological impairment, is similar to other skin diseases, such as psoriasis and atopic dermatitis (AD) (Linthorst Homan M W, Spuls P I, de Korte J, Bos J D, Sprangers M A, van der Veen J P. The burden of vitiligo: patient characteristics associated with quality of life. J Am Acad Dermatol 2009; 61:411-420). Involvement of exposed skin, such as the face and hands, can have a major impact on self-esteem and eventually link to the psychological burden and quality of life (Silverberg J I, Silverberg N B. Association between vitiligo extent and distribution and quality of life impairment. JAMA Dermatol 2013; 149:159-164). In some societies, there is poor acceptance and understanding of the disease, to the extent of discrimination against affected individuals (Yazdani Abyanch M A, Griffith R, Falto-Aizpurua L, Nouri K. The dark history of white spots. JAMA Dermatol 2014; 150:936). Approximately 75% of vitiligo sufferers feel their appearance is moderately to severely intolerable, and 41% of patients feel that there is little they can do to improve their condition, and feelings of hopelessness increase with time (Salzer B A, Schallreuter K U. Investigation of the personality structure in patients with vitiligo and a possible association with impaired catecholamine metabolism. Dermatology 1995; 190:109-115). In studies, 66% of patients report being distressed by their disease, and 92% have experienced stigmatization (Krüger C, Panske A, Schallreuter K U. Disease-related behavioral patterns and experiences affect quality of life in children and adolescents with vitiligo. Int J Dermatol 2014; 53:43-50). Feelings of embarrassment and fear of rejection can cause vitiligo patients to withdraw and lead to social isolation in both personal and professional relationships. A majority of patients with vitiligo have reported feelings of anxiety and embarrassment when meeting strangers or beginning a new sexual relationship (Porter J, Beuf A and Lerner A et al. The effect of vitiligo on sexual relationship. J Am Acad Dermatol 1990; 22:221-222). Additionally, clinical depression or depressive symptoms are associated with vitiligo. Patients with vitiligo were approximately 5 times more likely to suffer from depression than healthy controls (Lai Y C, Yew Y W, Kennedy C, Schwartz R A. Vitiligo and depression: a systematic review and meta-analysis of observational studies. Br J Dermatol 2017; 177:708-718; Osinubi O, Grainge M J, Hong L, et al. The prevalence of psychological comorbidity in people with vitiligo: a systematic review and meta-analysis. Br J Dermatol 2018; 178:863-878). A recent analysis indicated that the pooled prevalence of depression across 17 unique populations (n=1711) was 29% (Wang G, Qiu D, Yang H, Liu W. The prevalence and odds of depression in patients with vitiligo: a meta-analysis [published online ahead of print Dec. 9, 2017]. J Eur Acad Dermatol Venercol. doi: 10.1111/jdv.14739).

Studies also suggest that the onset of vitiligo beginning in childhood can be associated with significant psychological trauma that may have long lasting effects on self-esteem. The extent of vitiligo is associated with quality of life (QOL) impairment in children and adolescents, especially self-consciousness, but also bullying and teasing. Teenagers ages 15 to 17 years seem to experience the most self-consciousness of all pediatric age groups (Silverberg, supra). In a study comparing social development and the health-related quality of life of young adult patients with childhood vitiligo with healthy controls, vitiligo patients reporting negative childhood experiences reported significantly more problems in social development than those not reporting negative experiences. Negative childhood experiences were significantly associated with more health-related quality of life impairment in early adulthood (Linthorst Homan M W, De Korte J, Grootenhuis M A, Bos J D, Sprangers M A, Van Der Veen J P. Impact of childhood vitiligo on adult life. Br J Dermatol 2008; 159 (4): 915-20). Vitiligo is considered to be one of the most psychologically devastating diseases in dermatology.

Currently there is no approved drug treatment for vitiligo. Drugs have been used off-label; however, the clinical evidence that has been generated consists of a few, small, randomized, controlled studies. The off-label topical treatments that have been used for vitiligo include corticosteroids, calcineurin inhibitors, and vitamin D analogues. Other therapies include oral drugs, phototherapies, and some surgical methods (e.g., implantation of melanocytes into depigmented lesions). Due to the low level of evidence for any of these treatments, definitive clinical recommendation for treatment of vitiligo could not be proposed, and the management of vitiligo is empirical and based on the most recent consensus guidelines.

Vitiligo pathogenesis involves intrinsic defects within melanocytes and autoimmunity that targets these cells. Once melanocytes become stressed, they release inflammatory signals that activate innate immunity, which may represent the initiation event in vitiligo. Janus kinases are intracellular signaling enzymes that act downstream of key proinflammatory cytokines implicated in vitiligo pathogenesis. The oxidative stress, cell damage, and cytokines secreted from innate immune cells then trigger CXCL10 release by skin cells, and that recruits CD8+ T cells to the site. Activated CD8+ T cells produce IFN-γ and other inflammatory mediators to target and destroy melanocytes (Frisoli M L, Harris J E. Vitiligo: mechanistic insights lead to novel treatments. J Allergy Clin Immunol 2017; 140:654-662). IFN-γ signaling utilizes the Janus kinase-signal transducers and activators of transcription (JAK-STAT) pathway. Inhibition of JAK signaling may play a role in the treatment of vitiligo. Case reports of administering JAK inhibitors to patients with vitiligo include a patient with both alopecia arcata and vitiligo who was treated with oral ruxolitinib 20 mg BID for 20 weeks and subsequently had hair regrowth as well as repigmentation of areas affected with vitiligo (Harris J E, Rashighi M, Nguyen N, et al. Rapid skin repigmentation on oral ruxolitinib in a patient with coexistent vitiligo and alopecia areata (AA). J Am Acad Dermatol 2016; 74:370-371). In another report, a patient with widespread and progressive vitiligo who did not have a response to topical steroids, tacrolimus ointment, and NB-UVB phototherapy treated with oral tofacitinib at 5 mg QD and resulted in near complete repigmentation after 5 months of treatment (Craiglow B G, King B A. Tofacitinib citrate for the treatment of vitiligo: a pathogenesis-directed Therapy. JAMA Dermatol 2015; 151:1110-1112). There was a 20-week open-label study using topical ruxolitinib cream in 12 participants with vitiligo who had a minimum of 1% BSA affected. The results showed a 76% improvement in Face Vitiligo Area Scoring Index (F-VASI) and 26% improvement in Total Body Vitiligo Area Scoring Index (T-VASI) within 7 of 9 participants who completed the study (Rothstein B, Joshipura D, Saraiya A, et al. Treatment of vitiligo with the topical Janus kinase inhibitor ruxolitinib. J Am Acad Dermatol 2017; 76:1054-1060). The same group conducted an additional 32-week extension study with optional NB-UVB treatment (Joshipura D, Alomran A, Zancanaro P, Rosmarin D. Treatment of vitiligo with the topical Janus kinase inhibitor ruxolitinib: a 32-week open-label extension study with optional narrow-band ultraviolet B. J Am Acad Dermatol 2018; 78:1205-1207). Five participants completed the study, and 3 of them received NB-UVB. At Week 52 (Week 20+Week 32), results showed 92% improvement in F-VASI and 37% in T-VASI. The results also indicated that 2 participants who had failed prior phototherapy and topical cream monotherapy on truncal lesions responded after combined therapies. Additionally, participants were followed up with at 6 months after treatment discontinuation, and all 5 participants maintained response with maximum duration of more than 40 weeks. The results, however, were from studies that were open label and from exceedingly small sample sizes. Accordingly, the efficacy of ruxolitinib cream in treating vitiligo has yet to be clinically demonstrated in randomized, double-blind, vehicle-controlled trials excluding disparate treatment regimens.

SUMMARY

Accordingly, the present invention provides, inter alia, methods of treating patients suffering from vitiligo with ruxolitinib cream 0.15% QD, 0.5% QD, 1.5% QD, or 1.5% BID.

The present disclosure further provides a ruxolitinib composition or cream for use in any of the methods described herein.

The present disclosure also provides use of a ruxolitinib composition or cream for manufacture of a medicament for use in any of the methods described herein.

The details of one or more embodiments of the invention are set forth in the accompanying figures and the description below. Other features, objects, and advantages of the invention will be apparent from the description and drawings, and from the claims.

DESCRIPTION OF THE FIGURES

FIG. 53 is a table showing p-values from Fisher Exact Test for T-VASI25, T-VASI50, and T-VASI75 between combined group and vehicle group at Week 24.

FIG. 59 is a table of TEAEs through 52 weeks of treatment.

DETAILED DESCRIPTION

Figure 1:
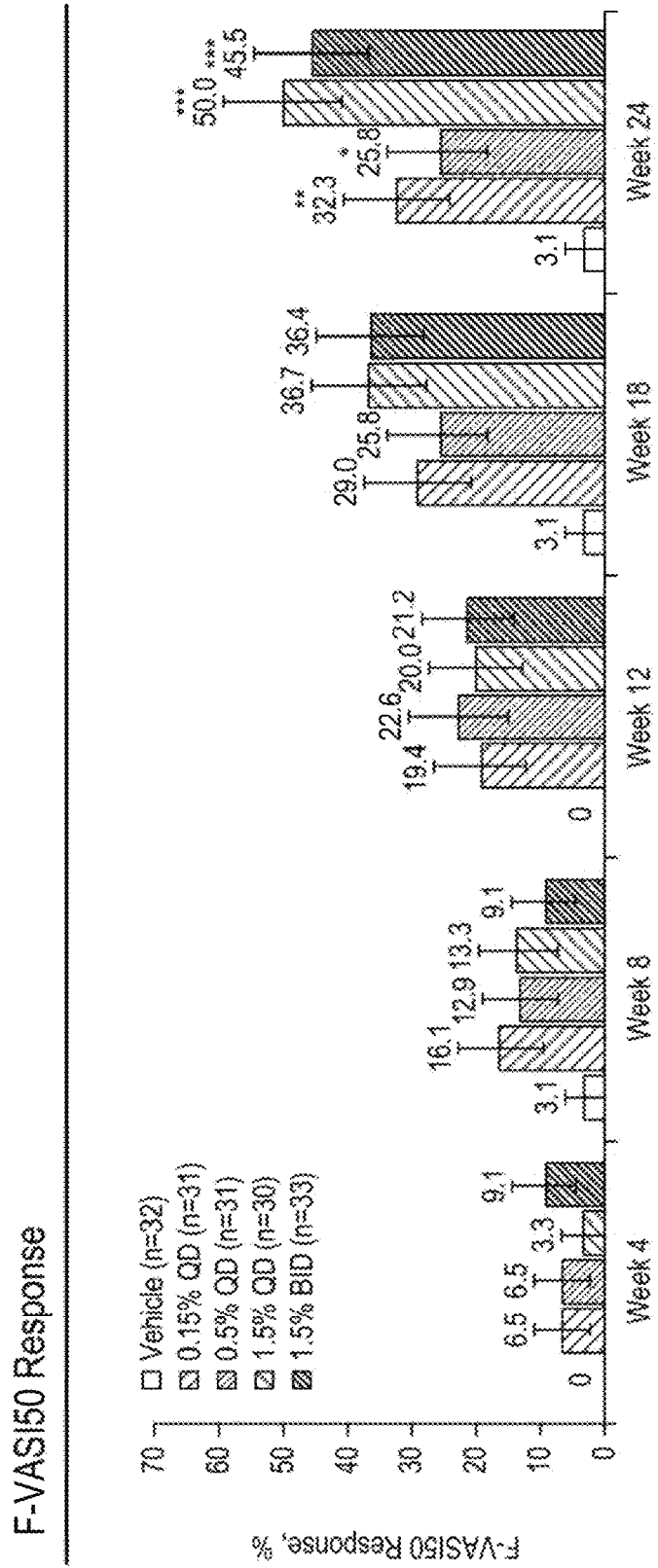
FIG. 1 is a graph of F-VASI-50 response (%) at Week 4, Week 8, Week 12, Week 18, and Week 24 for vehicle, 0.15% QD ruxolitinib cream, 0.5% QD ruxolitinib cream, 1.5% QD ruxolitinib cream, and 1.5% BID ruxolitinib cream (bars for each group shown consecutive order).
Figure 2:
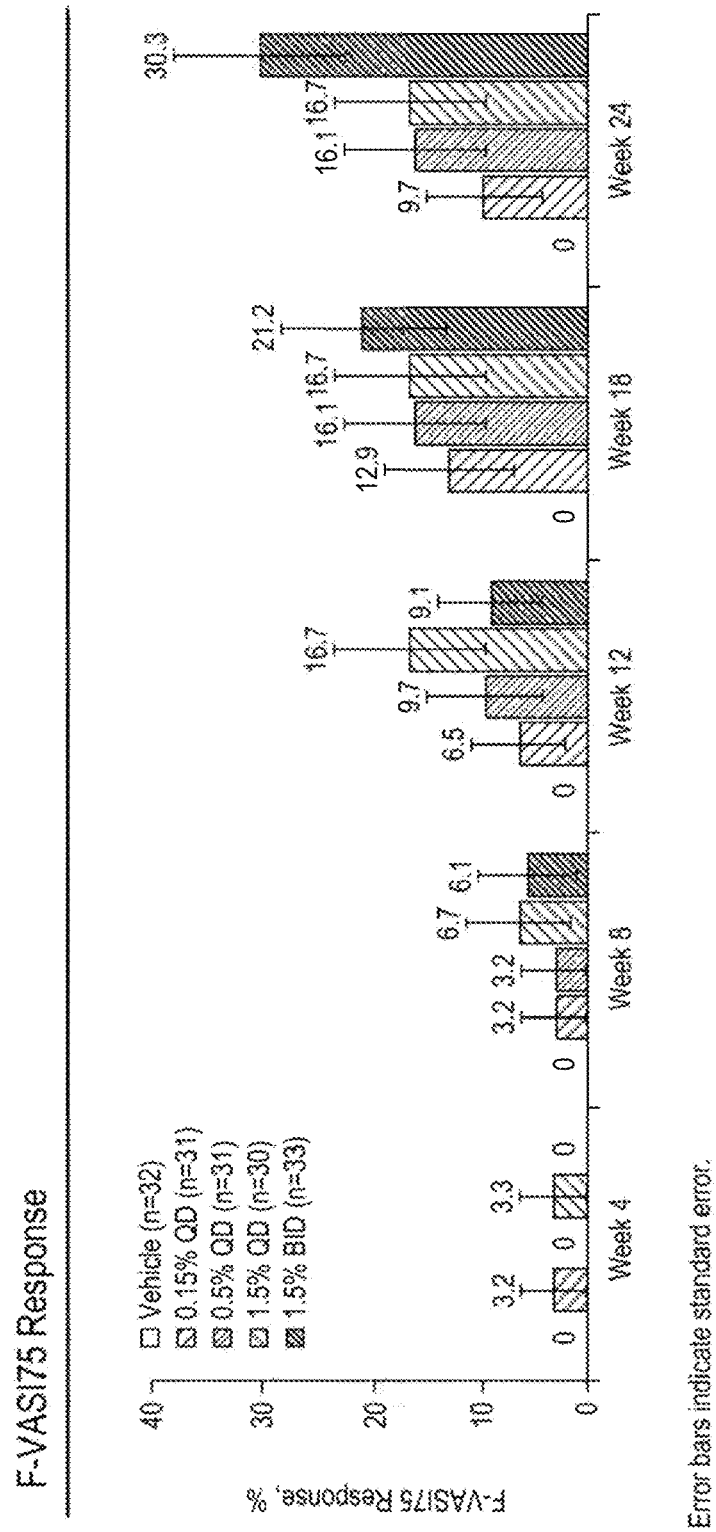
FIG. 2 is a graph of F-VASI-75 response (%) at Week 4, Week 8, Week 12, Week 18, and Week 24 for vehicle, 0.15% QD ruxolitinib cream, 0.5% QD ruxolitinib cream, 1.5% QD ruxolitinib cream, and 1.5% BID ruxolitinib cream (bars for each group shown consecutive order).

Ruxolitinib ((R)-3-(4-(7H-pyrrolo[2,3-d]pyrimidin-4-yl)-1H-pyrazol-1-yl)-3-cyclopentylpropanenitrile) (sometimes referred to as INCB018424), having the structure shown below, and its pharmaceutically acceptable salts have been previously been described in U.S. Pat. No. 7,598,257, which is incorporated herein by reference in its entirety. Ruxolitinib phosphate is described in U.S. Pat. No. 8,722,693, which is incorporated herein by reference in its entirety. The present disclosure describes, inter alia, methods of treating generalized vitiligo using ruxolitinib, or a pharmaceutically acceptable salt thereof.

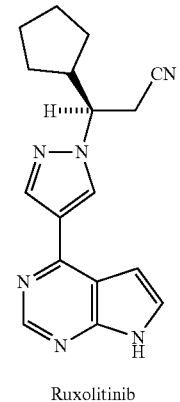 [SMILES: N#CC[C@H](C1CCCC1)n1cc(-c2ncnc3[nH]ccc23)cn1]

Ruxolitinib

Methods of Treatment

Accordingly, the present invention provides for the treatment of patients suffering from vitiligo with ruxolitinib cream 0.15% QD, 0.5% QD, 1.5% QD, or 1.5% BID. All percentages are on a (w/w) basis of ruxolitinib, or a pharmaceutically acceptable salt thereof (e.g., ruxolitinib phosphate) in the cream, on a free base basis.

In another embodiment, the present disclosure provides a method of treating vitiligo in a patient comprising administering to the patient in need thereof a composition (e.g., a cream) containing about 0.15% w/w ruxolitinib, or a pharmaceutically acceptable salt thereof, on a free base basis, once per day. In another embodiment, the present disclosure provides a method of treating vitiligo in a patient comprising administering to the patient in need thereof a composition (e.g., a cream) containing about 0.5% w/w ruxolitinib, or a pharmaceutically acceptable salt thereof, on a free base basis, once per day. In another embodiment, the present disclosure provides a method of treating vitiligo in a patient comprising administering to the patient in need thereof a composition (e.g., a cream) containing about 1.5% w/w ruxolitinib, or a pharmaceutically acceptable salt thereof, on a free base basis, once per day. In another embodiment, the present disclosure provides a method of treating vitiligo in a patient comprising administering to the patient in need thereof a composition (e.g., a cream) containing about 1.5% w/w ruxolitinib, or a pharmaceutically acceptable salt thereof, on a free base basis, twice per day.

In some embodiments, the patient is administered ruxolitinib cream 1.5% BID for up to 24 weeks.

In some embodiments, the patient is administered ruxolitinib cream 1.5% BID for up to 52 weeks.

In some embodiments, the patient is administered ruxolitinib cream 1.5% QD for up to 24 weeks.

In some embodiments, the patient is administered ruxolitinib cream 1.5% QD for up to 52 weeks.

In some embodiments, the patient is administered ruxolitinib cream 0.5% QD for up to 24 weeks.

In some embodiments, the patient is administered ruxolitinib cream 0.5% QD for up to 52 weeks.

In some embodiments, the patient is administered ruxolitinib cream 0.15% QD for up to 24 weeks.

In some embodiments, the patient is administered ruxolitinib cream 0.15% QD for up to 52 weeks.

In another embodiment, the present disclosure provides a method of treating vitiligo in a patient comprising administering to the patient in need thereof a cream containing about 1.5% w/w ruxolitinib, or a pharmaceutically acceptable salt thereof, on a free base basis, twice per day. In some embodiments, the cream contains 1.5% w/w ruxolitinib phosphate on a free base basis. In some embodiments, patients achieve a 25% or greater improvement in Face Vitiligo Area Scoring Index. In some embodiments, patients achieve a 50% or greater improvement in Face Vitiligo Area Scoring Index. In some embodiments, patients achieve a 75% or greater improvement in Face Vitiligo Area Scoring Index. In some embodiments, patients achieve a 90% or greater improvement in Face Vitiligo Area Scoring Index. In some embodiments, patients achieve a 25% or greater improvement in Total Body Vitiligo Area Scoring Index. In some embodiments, patients achieve a 50% or greater improvement in Total Body Vitiligo Area Scoring Index. In some embodiments, patients achieve a 75% or greater improvement in Total Body Vitiligo Area Scoring Index. In some embodiments, patients achieve a Facial Patient's Global Vitiligo Assessment response of 0 (no white patches) or 1 (mild) and at least a 1 point reduction from baseline. patients achieve a Facial Physician's Global Vitiligo Assessment of 0 (clear) or 1 (almost clear). In some embodiments, patients achieve a Total Physician's Global Vitiligo Assessment of 0 (clear) or 1 (almost clear). In some embodiments, patients achieve a Patient global impression of change for vitiligo of 1 (very much improved) or 2 (much improved).

In a further embodiment, the present disclosures provides a method of treating vitiligo in a patient comprising administering to the patient in need thereof a cream containing about 1.5% w/w ruxolitinib, or a pharmaceutically acceptable salt thereof, on a free base basis, once per day. In some embodiments, the cream contains 1.5% w/w ruxolitinib phosphate on a free base basis. In some embodiments, patients achieve a 25% or greater improvement in Face Vitiligo Area Scoring Index. In some embodiments, patients achieve a 50% or greater improvement in Face Vitiligo Area Scoring Index. In some embodiments, patients achieve a 75% or greater improvement in Face Vitiligo Area Scoring Index. In some embodiments, patients achieve a 90% or greater improvement in Face Vitiligo Area Scoring Index. In some embodiments, patients achieve a 25% or greater improvement in Total Body Vitiligo Area Scoring Index. In some embodiments, patients achieve a 50% or greater improvement in Total Body Vitiligo Area Scoring Index. In some embodiments, patients achieve a 75% or greater improvement in Total Body Vitiligo Area Scoring Index. In some embodiments, patients achieve a Facial Patient's Global Vitiligo Assessment response of 0 (no white patches) or 1 (mild) and at least a 1 point reduction from baseline. In some embodiments, patients achieve a Facial Physician's Global Vitiligo Assessment of 0 (clear) or 1 (almost clear). In some embodiments, patients achieve a Total Physician's Global Vitiligo Assessment of 0 (clear) or 1 (almost clear). In some embodiments, patients achieve a Patient global impression of change for vitiligo of 1 (very much improved) or 2 (much improved).

In another embodiment, the present disclosure provides a method of treating vitiligo in a patient comprising administering to the patient in need thereof a cream containing about 0.5% w/w ruxolitinib, or a pharmaceutically acceptable salt thereof, on a free base basis, once per day. In some embodiments, the cream contains 0.5% w/w ruxolitinib phosphate on a free base basis. In some embodiments, patients achieve a 25% or greater improvement in Face Vitiligo Area Scoring Index. In some embodiments, patients achieve a 50% or greater improvement in Face Vitiligo Area Scoring Index. In some embodiments, patients achieve a 75% or greater improvement in Face Vitiligo Area Scoring Index. In some embodiments, patients achieve a 90% or greater improvement in Face Vitiligo Area Scoring Index. In some embodiments, patients achieve a 25% or greater improvement in Total Body Vitiligo Area Scoring Index. In some embodiments, patients achieve a 50% or greater improvement in Total Body Vitiligo Area Scoring Index. In some embodiments, patients achieve a 75% or greater improvement in Total Body Vitiligo Area Scoring Index. In some embodiments, patients achieve a Facial Patient's Global Vitiligo Assessment response of 0 (no white patches) or 1 (mild) and at least a 1 point reduction from baseline. In some embodiments, wherein patients achieve a Facial Physician's Global Vitiligo Assessment of 0 (clear) or 1 (almost clear). In some embodiments, patients achieve a Total Physician's Global Vitiligo Assessment of 0 (clear) or 1 (almost clear). In some embodiments, patients achieve a Patient global impression of change for vitiligo of 1 (very much improved) or 2 (much improved).

In another embodiment, the present disclosure provides a method of treating vitiligo in a patient comprising administering to the patient in need thereof a cream containing about 0.15% w/w ruxolitinib, or a pharmaceutically acceptable salt thereof, on a free base basis, once per day. In some embodiments, the cream contains 0.15% w/w ruxolitinib phosphate on a free base basis. In some embodiments, patients achieve a 25% or greater improvement in Face Vitiligo Area Scoring Index. In some embodiments, patients achieve a 50% or greater improvement in Face Vitiligo Area Scoring Index. In some embodiments, patients achieve a 75% or greater improvement in Face Vitiligo Area Scoring Index. In some embodiments, patients achieve a 90% or greater improvement in Face Vitiligo Area Scoring Index. In some embodiments, patients achieve a 25% or greater improvement in Total Body Vitiligo Area Scoring Index. In some embodiments, patients achieve a 50% or greater improvement in Total Body Vitiligo Area Scoring Index. In some embodiments, patients achieve a 75% or greater improvement in Total Body Vitiligo Area Scoring Index. In some embodiments, patients achieve a Facial Patient's Global Vitiligo Assessment response of 0 (no white patches) or 1 (mild) and at least a 1 point reduction from baseline. In some embodiments, patients achieve a Facial Physician's Global Vitiligo Assessment of 0 (clear) or 1 (almost clear). In some embodiments, patients achieve a Total Physician's Global Vitiligo Assessment of 0 (clear) or 1 (almost clear). In some embodiments, patients achieve a Patient global impression of change for vitiligo of 1 (very much improved) or 2 (much improved).

In a further embodiment, the present disclosure provides treating vitiligo in a patient comprising topically administering a pharmaceutical composition (e.g., a cream) to an affected skin area of the patient, wherein the composition comprises about 0.15%, about 0.5%, or about 1.5% ruxolitinib, or a pharmaceutically acceptable salt thereof, by weight of the composition (or cream) (w/w) on a free base basis.

In some embodiments, the ruxolitinib, or the pharmaceutically acceptable salt thereof, is ruxolitinib phosphate. In some embodiments, the composition is a cream.

In some embodiments, the composition (or cream) comprises 0.15% ruxolitinib phosphate on a free base basis and is administered to the skin of the patient once-daily (QD).

In some embodiments, the composition (or cream) comprises 0.5% ruxolitinib phosphate on a free base basis and is administered to the skin of the patient once-daily (QD).

In some embodiments, the composition (or cream) comprises 1.5% ruxolitinib phosphate on a free base basis and is administered to the skin of the patient once-daily (QD).

In some embodiments, the composition (or cream) comprises 1.5% ruxolitinib phosphate on a free base basis and is administered to the skin of the patient twice-daily (BID).

In some embodiments, no more than than 60 grams of the composition (or cream) is administered in a 4 day period.

In some embodiments, the affected skin area of the patient is affected skin on the face of the patient.

In some embodiments, the affected skin area of patients is affected skin area on the face and body of the patient.

In some embodiments, the affected skin area of the patient is affected skin on the trunk of the patient.

In some embodiments, the affected skin area of the patient is affected skin on the upper extremities.

In some embodiments, the affected skin area of the patient is affected skin on the lower extremities.

In some embodiments, the affected skin area of the patient is affected skin on the hands.

In some embodiments, the affected skin area of the patient is affected skin on the feet.

In some embodiments, the affected skin area of the patient is affected skin on the head and neck.

In some embodiments, the patient achieves a 50% or greater improvement in Vitiligo Area Scoring Index score on the head and neck. In some embodiments, the patient achieves a 50% or greater improvement in Vitiligo Area Scoring Index score on the head and neck at Week 4; or at Week 8; or at Week 12; or at Week 18; or at Week 24; or at Week 28; or at Week 34; or at Week 40; or at Week 46; or at Week 52.

In some embodiments, the patient achieves a 50% or greater improvement in Vitiligo Area Scoring Index score on the upper extremities. In some embodiments, the patient achieves a 50% or greater improvement in Vitiligo Area Scoring Index score on the upper extremities at Week 4; or at Week 8; or at Week 12; or at Week 18; or at Week 24; or at Week 28; or at Week 34; or at Week 40; or at Week 46; or at Week 52.

In some embodiments, the patient achieves a 50% or greater improvement in Vitiligo Area Scoring Index score on the lower extremities. In some embodiments, the patient achieves a 50% or greater improvement in Vitiligo Area Scoring Index score on the lower extremities at Week 4; or at Week 8; or at Week 12; or at Week 18; or at Week 24; or at Week 28; or at Week 34; or at Week 40; or at Week 46; or at Week 52.

In some embodiments, the patient achieves a 50% or greater improvement in Vitiligo Area Scoring Index score on the hands. In some embodiments, the patient achieves a 50% or greater improvement in Vitiligo Area Scoring Index score on the hands at Week 4; or at Week 8; or at Week 12; or at Week 18; or at Week 24; or at Week 28; or at Week 34; or at Week 40; or at Week 46; or at Week 52.

In some embodiments, the patient achieves a 50% or greater improvement in Vitiligo Area Scoring Index score on the feet. In some embodiments, the patient achieves a 50% or greater improvement in Vitiligo Area Scoring Index score on the feet at Week 4; or at Week 8; or at Week 12; or at Week 18; or at Week 24; or at Week 28; or at Week 34; or at Week 40; or at Week 46; or at Week 52.

In some embodiments, the patient achieves a 75% or greater improvement in Vitiligo Area Scoring Index score on the head and neck. In some embodiments, the patient achieves a 75% or greater improvement in Vitiligo Area Scoring Index score on the head and neck at Week 4; or at Week 8; or at Week 12; or at Week 18; or at Week 24; or at Week 28; or at Week 34; or at Week 40; or at Week 46; or at Week 52.

In some embodiments, the patient achieves a 75% or greater improvement in Vitiligo Area Scoring Index score on the upper extremities. In some embodiments, the patient achieves a 75% or greater improvement in Vitiligo Area Scoring Index score on the upper extremities at Week 4; or at Week 8; or at Week 12; or at Week 18; or at Week 24; or at Week 28; or at Week 34; or at Week 40; or at Week 46; or at Week 52.

In some embodiments, the patient achieves a 75% or greater improvement in Vitiligo Area Scoring Index score on the lower extremities. In some embodiments, the patient achieves a 75% or greater improvement in Vitiligo Area Scoring Index score on the lower extremities at Week 4; or at Week 8; or at Week 12; or at Week 18; or at Week 24; or at Week 28; or at Week 34; or at Week 40; or at Week 46; or at Week 52. In some embodiments, the patient achieves a 75% or greater improvement in Vitiligo Area Scoring Index score on the hands.

In some embodiments, the patient achieves a 75% or greater improvement in Vitiligo Area Scoring Index score on the feet. In some embodiments, the patient achieves a 75% or greater improvement in Vitiligo Area Scoring Index score on the feet at Week 4; or at Week 8; or at Week 12; or at Week 18; or at Week 24; or at Week 28; or at Week 34; or at Week 40; or at Week 46; or at Week 52.

In some embodiments, the patient achieves a 25% or greater improvement in Vitiligo Area Scoring Index score on the head and neck. In some embodiments, the patient achieves a 25% or greater improvement in Vitiligo Area Scoring Index score on the head and neck at Week 4; or at Week 8; or at Week 12; or at Week 18; or at Week 24; or at Week 28; or at Week 34; or at Week 40; or at Week 46; or at Week 52.

In some embodiments, the patient achieves a 25% or greater improvement in Vitiligo Area Scoring Index score on the upper extremities. In some embodiments, the patient achieves a 25% or greater improvement in Vitiligo Area Scoring Index score on the upper extremities at Week 4; or at Week 8; or at Week 12; or at Week 18; or at Week 24; or at Week 28; or at Week 34; or at Week 40; or at Week 46; or at Week 52.

In some embodiments, the patient achieves a 25% or greater improvement in Vitiligo Area Scoring Index score on the lower extremities. In some embodiments, the patient achieves a 25% or greater improvement in Vitiligo Area Scoring Index score on the lower extremities at Week 4; or at Week 8; or at Week 12; or at Week 18; or at Week 24; or at Week 28; or at Week 34; or at Week 40; or at Week 46; or at Week 52.

In some embodiments, the patient achieves a 25% or greater improvement in Vitiligo Area Scoring Index score on the hands. In some embodiments, the patient achieves a 25% or greater improvement in Vitiligo Area Scoring Index score on the hands at Week 4; or at Week 8; or at Week 12; or at Week 18; or at Week 24; or at Week 28; or at Week 34; or at Week 40; or at Week 46; or at Week 52.

In some embodiments, the patient achieves a 25% or greater improvement in Vitiligo Area Scoring Index score on the feet. In some embodiments, the patient achieves a 25% or greater improvement in Vitiligo Area Scoring Index score on the feet at Week 4; or at Week 8; or at Week 12; or at Week 18; or at Week 24; or at Week 28; or at Week 34; or at Week 40; or at Week 46; or at Week 52.

In some embodiments, the patient suffers from generalized vitiligo.

In some embodiments, the patient suffers from segmental vitiligo.

In some embodiments, the patient suffers from segmental vitiligo and achieves a 25% or greater improvement in Facial Vitiligo Area Scoring Index score. In some embodiments, the patient suffers from segmental vitiligo and achieves a 25% or greater improvement in Facial Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 50% or greater improvement in Facial Vitiligo Area Scoring Index score. In some embodiments, the patient suffers from segmental vitiligo and achieves a 50% or greater improvement in Facial Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 75% or greater improvement in Facial Vitiligo Area Scoring Index score. In some embodiments, the patient suffers from segmental vitiligo and achieves a 75% or greater improvement in Facial Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 90% or greater improvement in Facial Vitiligo Area Scoring Index score. In some embodiments, the patient suffers from segmental vitiligo and achieves a 90% or greater improvement in Facial Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 25% or greater improvement in Total Body Vitiligo Area Scoring Index score. In some embodiments, the patient suffers from segmental vitiligo and achieves a 25% or greater improvement in Total Body Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 50% or greater improvement in Total Body Vitiligo Area Scoring Index score. In some embodiments, the patient suffers from segmental vitiligo and achieves a 50% or greater improvement in Total Body Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 75% or greater improvement in Total Body Vitiligo Area Scoring Index score. In some embodiments, the patient suffers from segmental vitiligo and achieves a 75% or greater improvement in Total Body Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient suffers from segmental vitiligo and achieves a 90% or greater improvement in Total Body Vitiligo Area Scoring Index score. In some embodiments, the patient suffers from segmental vitiligo and achieves a 90% or greater improvement in Total Body Vitiligo Area Scoring Index score at Week 4; or at Week 8; or at Week 12; or at Week 18; or at Week 24; or at Week 28; or at Week 34; or at Week 40; or at Week 46; or at Week 52.

In some embodiments, the patient is white.

In some embodiments, the patient is non-white.

In some embodiments, the patient is female.

In some embodiments, the patient is male.

In some embodiments, the patient has Fitzpatrick scale Type I, II, or III skin type.

In some embodiments, the patient has 1.5% or less facial BSA at baseline.

In some embodiments, the patient has an F-VASI score of from 0.75 to less than 1.5 at baseline.

In some embodiments, the patient has stable vitiligo at baseline.

In some embodiments, the patient has progressive vitiligo at baseline. For example, a patient with progressive vitiligo experiences new lesions and/or other objective clinical signs of active disease (e.g., confetti-like macules and/or trichrome lesions).

In some embodiments, the patient has a disease duration at baseline of at least 5 years.

In some embodiments, the patient has a disease duration at baseline of at least 10 years.

In some embodiments, the patient has a disease duration at baseline of at least 20 years.

In some embodiments, the patient was previously treated with topical corticosteroids.

In some embodiments, the patient has total BSA of 20% or lower.

In some embodiments, the patient has total BSA of 10% or greater. In some embodiments, the patient has total BSA of greater than 10%.

In some embodiments, the patient has total BSA of 15% or greater. In some embodiments, the patient has total BSA of greater than 15%.

In some embodiments, the patient has total BSA of 20% or greater. In some embodiments, the patient has total BSA of greater than 20%.

In some embodiments, the patient has long standing vitiligo.

In some embodiments, the patient has a % facial body surface area affected by vitiligo (F-BSA) of greater than 1.5%.

In some embodiments, the patient has a % facial body surface area affected by vitiligo (F-BSA) of greater than 1.5% and achieves achieves a 50% or greater improvement in Facial Vitiligo Area Scoring Index score at Week 24.

In some embodiments, the patient suffers from generalized vitiligo with depigmented area of: (i) 0.5% or greater body surface area (BSA) on the face, (ii) 3% or greater BSA on non-facial areas, and (iii) total body not exceeding 10% BSA.

In some embodiments, the patient suffers from generalized vitiligo with depigmented area of: (i) 0.5% or greater body surface area (BSA) on the face, (ii) 3% or greater BSA on non-facial areas, and (iii) total body not exceeding 20% BSA.

Total % BSA (includes facial and nonfacial areas) afflicted by vitiligo can be approximated to the nearest 0.1% using the Palmar Method as guides, the palm plus 5 digits, with fingers tucked together and thumb tucked to the side (handprint), as 1% BSA and the thumb as 0.1% BSA.

In some embodiments, the patient is an individual aged 12 years or older.

In some embodiments, the patient is an individual aged 50 years or younger.

In some embodiments, the patient is an individual aged 12 years to 50 years.

In some embodiments, the patient is an adult.

In some embodiments, the patient is an adolescent.

In some embodiments, the patient has Fitzpatrick scale Type I or II skin type.

In some embodiments, the patient has Fitzpatrick scale Type III, IV, V, or VI skin type.

In some embodiments, the patient is not:
(i) a patient having no pigmented hair within the affected facial area;
(ii) a patient with a non-generalized form of vitiligo (including, but not limited to, segmental vitiligo) or other differential diagnosis of vitiligo or other skin depigmentation disorder (including, but not limited to piebaldism, pityriasis alba, leprosy, postinflammatory hypopigmentation, progressive macule hypomelanosis, nevus anemicus, chemical leukoderma, and tinea versicolor);
(iii) a patient who previously used depigmentation treatment other than bleaching for past treatment of vitiligo or other pigmented areas; and
(iv) a patient who previously used (a) active acute bacterial, fungal, or viral skin infection; (b) a history of thrombosis (including deep venous thrombosis (DVT), pulmonary embolism (PE) or arterial thrombosis); (c) clinically significant or uncontrolled cardiac disease, including unstable angina, acute myocardial infarction within 6 months from Day 1 of study drug administration, New York Heart Association Class III or IV congestive heart failure, and arrhythmia requiring therapy or uncontrolled hypertension (blood pressure>150/90 mmHg); (d) current liver disease (including known hepatitis B or C, with hepatic or biliary abnormalities); (e) history of alcoholism or drug addiction within 1 year before screening or current alcohol or drug use that, in the opinion of a physician, will interfere with the participant's ability to comply with the administration schedule and treatment assessment; and (f) mental health institution by virtue of an order issued either by the judicial or the administrative authorities;
(v) a patient having any of the laboratory values at screening (a) hemoglobin (<10 g/dL); (b) liver function tests: aspartate aminotransferase or alanine aminotransferase≥2× upper limit of normal; or alkaline phosphatase and/or bilirubin>1.5× upper limit of normal; (c) Severe renal disease on dialysis (serum creatinine>2 mg/dL); (d) Clinically significant abnormal thyroid-stimulating hormone or free T4 at screening as determined by a physician; or (e) positive serology test results at screening for HIV antibody;
(vi) a patient with a body mass index<17 or >40 kg/m$^2$; and
(vii) pregnant or lactating.

In some embodiments, the patient is not:
(i) a patient having no pigmented hair within the affected facial area;
(ii) a patient with a non-generalized form of vitiligo (including, but not limited to, segmental vitiligo) or other differential diagnosis of vitiligo or other skin depigmentation disorder (including, but not limited to piebaldism, pityriasis alba, leprosy, postinflammatory hypopigmentation, progressive macule hypomelanosis, nevus anemicus, chemical leukoderma, and tinea versicolor);
(iii) a patient who previously used depigmentation treatment other than bleaching for past treatment of vitiligo or other pigmented areas; and
(iv) a patient who previously used (a) active acute bacterial, fungal, or viral skin infection; (b) a history of thrombosis (including deep venous thrombosis (DVT), pulmonary embolism (PE) or arterial thrombosis); (c) clinically significant or uncontrolled cardiac disease, including unstable angina, acute myocardial infarction within 6 months from Day 1 of study drug administration, New York Heart Association Class III or IV congestive heart failure, and arrhythmia requiring therapy or uncontrolled hypertension (blood pressure>150/90 mmHg); (d) current liver disease (including known hepatitis B or C, with hepatic or biliary abnormalities); (e) history of alcoholism or drug addiction within 1 year before screening or current alcohol or drug use that, in the opinion of a physician, will interfere with the participant's ability to comply with the administration schedule and treatment assessment; and (f) mental health institution by virtue of an order issued either by the judicial or the administrative authorities;
(v) a patient having any of the laboratory values at screening (a) hemoglobin (<10 g/dL); (b) liver function tests: aspartate aminotransferase or alanine aminotransferase≥2× upper limit of normal; or alkaline phosphatase and/or bilirubin>1.5× upper limit of normal; (c) Severe renal disease on dialysis (serum creatinine>2 mg/dL); (d) Clinically significant abnormal thyroid-stimulating hormone or free T4 at screening as determined by a physician; or (c) positive serology test results at screening for HIV antibody;
(vi) a patient with a body mass index<17 or >40 kg/m$^2$; or
(vii) pregnant or lactating.

In some embodiments, the patient did not previously receive a JAK inhibitor, systemic or topical.

In some embodiments, the method does not comprise administering a topical drug on the affected area (including but not limited to, corticosteroids, calcineurin, and phosphodiesterase type 4 inhibitors or retinoids). In some embodiments, the method does not comprise, within 1 week after initiation of treating with the composition (or cream), administering a topical drug on the affected area (including but not limited to, corticosteroids, calcineurin, and phosphodiesterase type 4 inhibitors or retinoids).

In some embodiments, the method does not comprise administering melanocyte-stimulating agents (including but not limited to, afamelanotide), immunomodulating systemic medications (including but not limited to, corticosteroids, methotrexate, cyclosporine), any systemic therapies that could increase the skin sensitivity to UV/visible light or impact skin pigmentation (including but not limited to, tetracyclines and metoxypsoralens), and live vaccine. In some embodiments, the method does not comprise, within 4 weeks after initiation of treating with the composition (or cream), administering melanocyte-stimulating agents (including but not limited to, afamelanotide), immunomodulating systemic medications (including but not limited to, corticosteroids, methotrexate, cyclosporine), any systemic therapies that could increase the skin sensitivity to UV/visible light or impact skin pigmentation (including but not limited to, tetracyclines and metoxypsoralens), and live vaccine.

In some embodiments, the method does not comprise administering laser or any kind of phototherapy (including but not limited to, a tanning bed or intentional UV exposure). In some embodiments, the method does not comprise, within 8 weeks after initiation of treating with the composition (or cream), laser or any kind of phototherapy (including but not limited to, a tanning bed or intentional UV exposure).

In some embodiments, the method does not comprise administering a biologic for treatment of vitiligo. In some embodiments, the method does not comprise, within 12 weeks after initiation of treating with the composition (or cream), administering a biologic for treatment of vitiligo.

In some embodiments, the patient previously received phototherapy (e.g., including narrowband ultraviolet B phototherapy, psoralen ultraviolet A photochemotherapy, or excimer laser).

In some embodiments, the patient achieves a 50% or greater improvement in Face Vitiligo Area Scoring Index (F-VASI50). In some embodiments, the patient achieves a 75% or greater improvement in Face Vitiligo Area Scoring Index (F-VASI75). In some embodiments, the patient achieves a 90% or greater improvement in Face Vitiligo Area Scoring Index (F-VASI90.

In some embodiments, the patient achieves a 75% or greater improvement in Face Vitiligo Area Scoring Index (F-VASI75) at week 24.

In some embodiments, the patient achieves a 75% or greater improvement in Face Vitiligo Area Scoring Index (F-VASI75) at week 52.

In some embodiments, the patient achieves a 50% or greater improvement in Face Vitiligo Area Scoring Index (F-VASI50) at week 24.

In some embodiments, the patient achieves a 50% or greater improvement in Face Vitiligo Area Scoring Index (F-VASI50) at week 52.

In some embodiments, the patient achieves a 90% or greater improvement in Face Vitiligo Area Scoring Index (F-VASI90) at week 24.

In some embodiments, the patient achieves a 90% or greater improvement in Face Vitiligo Area Scoring Index (F-VASI90) at week 52.

In some embodiments, the patient achieves a 25% or greater improvement in Total Body Vitiligo Area Scoring Index (T-VASI25). In some embodiments, the patient achieves a 50% or greater improvement in Total Body Vitiligo Area Scoring Index (T-VASI50). In some embodiments, the patient achieves a 75% or greater improvement in Total Body Vitiligo Area Scoring Index (T-VASI75).

In some embodiments, the patient achieves a 25% or greater improvement in Total Body Vitiligo Area Scoring Index (T-VASI25) at week 24.

In some embodiments, the patient achieves a 25% or greater improvement in Total Body Vitiligo Area Scoring Index (T-VASI25) at week 52.

In some embodiments, the patient achieves a 50% or greater improvement in Total Body Vitiligo Area Scoring Index (T-VASI50) at week 24.

In some embodiments, the patient achieves a 50% or greater improvement in Total Body Vitiligo Area Scoring Index (T-VASI50) at week 52.

In some embodiments, the patient achieves a 75% or greater improvement in Total Body Vitiligo Area Scoring Index (T-VASI75) at week 24.

In some embodiments, the patient achieves a 75% or greater improvement in Total Body Vitiligo Area Scoring Index (T-VASI75) at week 52.

In some embodiments, the patient achieves a score of 4 or 5 in Vitiligo Noticeability Scale (VNS). The VNS is a patient-reported measure of vitiligo treatment success, which has a 5-point scale (Batchelor J M, Tan W, Tour S, Yong A, Montgomery A A, Thomas K S. Validation of the Vitiligo Noticeability Scale: a patient-reported outcome measure of vitiligo treatment success. Br J Dermatol 2016; 174:386-394): (1) More noticeable, (2) As noticeable, (3) Slightly less noticeable, (4) A lot less noticeable, and (5) No longer noticeable.

In some embodiments, the patient achieves improvement in % facial body surface area affected by vitiligo (F-BSA) from baseline.

In some embodiments, the improvement in F-BSA from baseline is about 10 percentage points.

In some embodiments, the improvement in F-BSA from baseline is about 15 percentage points.

In some embodiments, the improvement in F-BSA from baseline is about 20 percentage points.

In some embodiments, the present disclosure further provides a method of treating nonfacial vitiligo in a patient, comprising administering to the patient in need thereof a composition (e.g., a cream) containing about 1.5% w/w ruxolitinib, or a pharmaceutically acceptable salt thereof, on a free base basis, twice per day.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient previously received phototherapy for vitiligo.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient had high inflammatory burden before the administering step.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the composition (e.g., a cream) is applied to the patient's hands, feet, or both.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient is a female and equal to or younger than 50 years of age.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein patients who are female and equal to or younger than 50 years of age respond better after 24 weeks of administering the composition (e.g., a cream) than men of the same age.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient is a female.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein patients who are female respond better after 24 weeks of administering the composition (e.g., a cream) than men.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient has had vitiligo for greater than 20 years before the administering step.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein patients who have had vitiligo for greater than 20 years before the administering step respond better after 24 weeks of administering the composition (e.g., a cream) than patients who have not had vitiligo for greater than 20 years before the administering step.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient has a skin type I-III.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient has a skin type I-II.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein patients having skin type I-III respond better after 24 weeks of administering the composition (e.g., a cream) than patients who do not have skin type I-III.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein there is no substantial difference in response between white patients and non-white patients.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein there is no substantial difference in response between patients having stable vitiligo and patients having progressive vitiligo.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patients have progressive vitiligo.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein there is no substantial difference in response between patients having BSA equal to or less than 20 and patients having BSA greater than 20.

In some embodiments, the present disclosure further provides a method of treating vitiligo in a patient, comprising administering to the patient in need thereof a composition (e.g., a cream) containing about 1.5% w/w ruxolitinib, or a pharmaceutically acceptable salt thereof, on a free base basis, twice per day; wherein the patient has a BSA greater than 20.

The severity of vitiligo can be assessed by the physician using the Physician's Global Vitiligo Assessment (PhGVA), which has a 5-point scale as shown in the table below. Response can be reported for face or overall (F-PhGVA or T-PhGVA).

| Score | Severity | Description |
| --- | --- | --- |
| 0 | Clear | No signs of vitiligo. Complete repigmentation. |
| 1 | Almost clear | Only specks of depigmentation present. |

| Score | Severity | Description |
|---|---|---|
| 2 | Mild disease | Pigmented and depigmented areas are equal. |
| 3 | Moderate disease | More or complete depigmentation (may include < 30% hair whitening). |
| 4 | Severe disease | Complete depigmentation plus > 30% hair whitening. |

In some embodiments, the patient achieves a Patient global impression of change for vitiligo of 1 (very much improved) or 2 (much improved). The PaGIC-V is an assessment of improvement by the patient on a 7-point scale comparing the vitiligo areas at baseline with the participant's treated areas of vitiligo: (1) Very much improved, (2) Much improved, (3) Minimally improved, (4) No change, (5) Minimally worse, (6) Much worse, and (7) Very much worse. Response can be reported for face or total body (F-PaGVA or T-PaGVA)

In some embodiments, the mean plasma concentration of ruxolitinib is less than 150 nM after two hours of administering BID.

In some embodiments, the mean plasma concentration of ruxolitinib is less than 120 nM after two hours of administering BID.

In some embodiments, the mean plasma concentration of ruxolitinib is less than 80 nM after two hours of administering QD.

In some embodiments, the mean plasma concentration of ruxolitinib is less than 60 nM after two hours of administering QD.

As used herein, the term "human subject", "individual" or "patient," used interchangeably, refers to any animal, including mammals, preferably mice, rats, other rodents, rabbits, dogs, cats, swine, cattle, sheep, horses, or primates, and most preferably humans. In some embodiments, the patient is a human. In some embodiments, the patient is a human aged 12 years or older.

As used herein embodiments that refer to patient may be combined with embodiments that refer to patients and vice versa. In some embodiments, "patients" means one patient. In some embodiments, "patients" means a patient population. In some embodiments, "patients" means one or more patients. In some embodiments, "a patient" means one patient. In some embodiments, "a patient" means a patient population. In some embodiments, "a patient" means one or more patients.

As used herein. "contains" is equivalent to "comprises".

Pharmaceutical Compositions

In some embodiments, the pharmaceutical composition is a cream formulation. In some embodiments, the cream formulation is an oil-in-water emulsion. In some embodiments, the cream formulation is described in U.S. Patent Publ. No. 2015/0250790, which is incorporated herein by reference in its entirety.

In some embodiments, the oil-in-water emulsion comprises water, an oil component, an emulsifier, and the 1.5% by weight of the formulation of the ruxolitinib, or the pharmaceutically acceptable salt thereof, on a free base basis. In some embodiments, the oil-in-water emulsion comprises water, an oil component, an emulsifier, and the 1.5% by weight of the formulation of the ruxolitinib phosphate on a free base basis.

In some embodiments, the pH of the cream formulation is about 2.8 to about 3.9. In some embodiments, the pH of the cream formulation is about 2.8 to about 3.6. In some embodiments, the pH of the cream formulation is about 2.9 to about 3.6. In some embodiments, the pH of the cream formulation is not greater than 3.6.

As used herein, the term "emulsifier component" refers, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

In transport studies with freshly excised mouse skin, the oil-in-water formulations also displayed a general trend of increased permeability when the strength of the solubilized cream was increased from 0.5% w/w to 1.5% w/w. Further, the formulations described herein are relatively simple to manufacture with a repeatable process of formulation. The resultant product is easily packaged. The formulations appear to have good stability and relatively consistent permeation profiles.

In some embodiments, the oil component is present in an amount of about 10% to about 40% by weight of the formulation.

In some embodiments, the oil component is present in an amount of about 17% to about 27% by weight of the formulation.

In some embodiments, the oil component is present in an amount of about 20% to about 27% by weight of the formulation.

In some embodiments, the oil component is present in an amount of about 17% to about 24% by weight of the formulation.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent component is present in an amount of about 2% to about 15% by weight of the formulation.

In some embodiments, the occlusive agent component is present in an amount of about 5% to about 10% by weight of the formulation.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol). vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the oil component comprises a stiffening agent component.

In some embodiments, the stiffening agent component is present in an amount of about 2% to about 8% by weight of the formulation.

In some embodiments, the stiffening agent component is present in an amount of about 3% to about 6% by weight of the formulation.

In some embodiments, the stiffening agent component is present in an amount of about 4% to about 7% by weight of the formulation.

As used herein, the term "stiffening agent component" refers to a substance or mixture of substances that increases the viscosity and/or consistency of the formulation or improves the rheology of the formulation.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the oil component comprises an emollient component.

In some embodiments, the emollient component is present in an amount of about 5% to about 15% by weight of the formulation.

In some embodiments, the emollient component is present in an amount of about 7% to about 13% by weight of the formulation.

As used herein, the term "emollient component" refers to an agent that softens or soothes the skin or soothes an irritated internal surface.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the emollient component comprises one or more substances independently selected from light mineral oil, medium chain triglycerides, and dimethicone.

In some embodiments, the water is present in an amount of about 35% to about 65% by weight of the formulation.

In some embodiments, the water is present in an amount of about 40% to about 60% by weight of the formulation.

In some embodiments, the water is present in an amount of about 45% to about 55% by weight of the formulation.

In some embodiments, the emulsifier component is present in an amount of about 1% to about 9% by weight of the formulation.

In some embodiments, the emulsifier component is present in an amount of about 2% to about 6% by weight of the formulation.

In some embodiments, the emulsifier component is present in an amount of about 3% to about 5% by weight of the formulation.

In some embodiments, the emulsifier component is present in an amount of about 4% to about 7% by weight of the formulation.

In some embodiments, the pharmaceutical formulation comprises an emulsifier component and a stiffening agent component, wherein the combined amount of emulsifier component and stiffening agent component is at least about 8% by weight of the formulation.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the pharmaceutical formulation further comprises a stabilizing agent component.

In some embodiments, the stabilizing agent component is present in an amount of about 0.05% to about 5% by weight of the formulation.

In some embodiments, the stabilizing agent component is present in an amount of about 0.1% to about 2% by weight of the formulation.

In some embodiments, the stabilizing agent component is present in an amount of about 0.3 to about 0.5% by weight of the formulation.

As used herein, the term "stabilizing agent component" refers to a substance or mixture of substances that improves the stability of the pharmaceutical formulation and/or the compatibility of the components in the formulation. In some embodiments, the stabilizing agent component prevents agglomeration of the emulsion and stabilizes the droplets in the oil-in-water emulsion.

In some embodiments, the stabilizing agent component comprises one or more substances independently selected from polysaccharides.

In some embodiments, the stabilizing agent component comprises xanthan gum.

In some embodiments, the pharmaceutical formulation further comprises a solvent component.

In some embodiments, the solvent component is present in an amount of about 10% to about 35% by weight of the formulation.

In some embodiments, the solvent component is present in an amount of about 15% to about 30% by weight of the formulation.

In some embodiments, the solvent component is present in an amount of about 20% to about 25% by weight of the formulation.

As used herein, the term "solvent component" is a liquid substance or mixture of liquid substances capable of dissolving ruxolitinib or other substances in the formulation. In some embodiments, the solvent component is a liquid substance or mixture of liquid substances in which ruxolitinib, or its pharmaceutically acceptable salt, has reasonable solubility. For example, solubilities of ruxolitinib (free base) or its phosphate salt are reported in Table 21 of U.S. Patent Publ. No. 2015/0250790. In some embodiments, a solvent is a substance or mixture thereof, in which ruxolitinib, or its pharmaceutically acceptable salt (whichever is used), has a solubility of at least about 10 mg/mL or greater, at least about 15 mg/mL or greater, or at least about 20 mg/mL or greater, when measured as described in Example 4 of U.S. Patent Publ. No. 2015/0250790.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the therapeutic agent is present in an amount of about 0.5% to about 1.5% by weight of the formulation on a free base basis.

In some embodiments, the therapeutic agent is present in an amount of about 0.5% by weight of the formulation on a free base basis.

In some embodiments, the therapeutic agent is present in an amount of about 1% by weight of the formulation on a free base basis.

In some embodiments, the therapeutic agent is present in an amount of about 1.5% by weight of the formulation on a free base basis.

In some embodiments, the therapeutic agent is (R)-3-cyclopentyl-3-[4-(7H-pyrrolo[2,3-d]pyrimidin-4-yl)-1H-pyrazol-1-yl]propanenitrile phosphate.

In some embodiments, the pharmaceutical formulation comprises:
  from about 35% to about 65% of water by weight of the formulation;
  from about 10% to about 40% of an oil component by weight of the formulation;
  from about 1% to about 9% of an emulsifier component by weight of the formulation;
  from about 10% to about 35% of a solvent component by weight of the formulation;
  from about 0.05% to about 5% of a stabilizing agent component by weight of the formulation; and
  about 1.5% of ruxolitinib, or a pharmaceutically acceptable salt thereof, by weight of the formulation on a free base basis.

In some embodiments, the pharmaceutical formulation comprises:
  from about 40% to about 60% of water by weight of the formulation;
  from about 15% to about 30% of an oil component by weight of the formulation;
  from about 2% to about 6% of an emulsifier component by weight of the formulation;
  from about 15% to about 30% of a solvent component by weight of the formulation;
  from about 0.1% to about 2% of a stabilizing agent component by weight of the formulation; and
  about 1.5% of ruxolitinib, or a pharmaceutically acceptable salt thereof, by weight of the formulation on a free base basis.

In some embodiments, the pharmaceutical formulation comprises:
  from about 45% to about 55% of water by weight of the formulation;
  from about 17% to about 27% of an oil component by weight of the formulation;
  from about 3% to about 5% of an emulsifier component by weight of the formulation;
  from about 20% to about 25% of a solvent component by weight of the formulation;
  from about 0.3% to about 0.5% of a stabilizing agent component by weight of the formulation; and
  about 1.5% of ruxolitinib, or a pharmaceutically acceptable salt thereof, by weight of the formulation on a free base basis.

In some embodiments, the pharmaceutical formulation comprises:
  from about 45% to about 55% of water by weight of the formulation;
  from about 17% to about 27% of an oil component by weight of the formulation;
  from about 4% to about 7% of an emulsifier component by weight of the formulation;
  from about 20% to about 25% of a solvent component by weight of the formulation;
  from about 0.3% to about 0.5% of a stabilizing agent component by weight of the formulation; and
  about 1.5% of ruxolitinib, or a pharmaceutically acceptable salt thereof, by weight of the formulation on a free base basis.

In some embodiments, the pharmaceutical formulation comprises:
  from about 45% to about 55% of water by weight of the formulation;
  from about 17% to about 24% of an oil component by weight of the formulation;
  from about 4% to about 7% of an emulsifier component by weight of the formulation;
  from about 20% to about 25% of a solvent component by weight of the formulation;
  from about 0.3% to about 0.5% of a stabilizing agent component by weight of the formulation; and
  about 1.5% of ruxolitinib, or a pharmaceutically acceptable salt thereof, by weight of the formulation on a free base basis.

In some embodiments:
  the oil component comprises one or more substances independently selected from petrolatums, fatty alcohols, mineral oils, triglycerides, and dimethicones;
  the emulsifier component comprises one or more substances independently selected from glyceryl fatty esters and sorbitan fatty esters;
  the solvent component comprises one or more substances independently selected from alkylene glycols and polyalkylene glycols; and
  the stabilizing agent component comprises one or more substances independently selected from polysaccharides.

In some embodiments:
  the oil component comprises one or more substances independently selected from white petrolatum, cetyl alcohol, stearyl alcohol, light mineral oil, medium chain triglycerides, and dimethicone;
  the emulsifier component comprises one or more substances independently selected from glyceryl stearate and polysorbate 20;
  the solvent component comprises one or more substances independently selected from propylene glycol and polyethylene glycol; and
  the stabilizing agent component comprises xanthan gum.

In some embodiments, the pharmaceutical formulation comprises:
  from about 35% to about 65% of water by weight of the formulation;
  from about 2% to about 15% of an occlusive agent component by weight of the formulation;

from about 2% to about 8% of a stiffening agent component by weight of the formulation;
from about 5% to about 15% of an emollient component by weight of the formulation;
from about 1% to about 9% of an emulsifier component by weight of the formulation;
from about 0.05% to about 5% of a stabilizing agent component by weight of the formulation;
from about 10% to about 35% of a solvent component by weight of the formulation; and
about 1.5% of ruxolitinib, or a pharmaceutically acceptable salt thereof, by weight of the formulation on a free base basis.

In some embodiments, the pharmaceutical formulation comprises:
from about 40% to about 60% of water by weight of the formulation;
from about 5% to about 10% of an occlusive agent component by weight of the formulation;
from about 2% to about 8% of a stiffening agent component by weight of the formulation;
from about 7% to about 12% of an emollient component by weight of the formulation;
from about 2% to about 6% of an emulsifier component by weight of the formulation;
from about 0.1% to about 2% of a stabilizing agent by weight of the formulation;
from about 15% to about 30% of a solvent component by weight of the formulation; and
about 1.5% of ruxolitinib, or a pharmaceutically acceptable salt thereof, by weight of the formulation on a free base basis.

In some embodiments, the pharmaceutical formulation comprises:
from about 45% to about 55% of water by weight of the formulation;
from about 5% to about 10% of an occlusive agent component by weight of the formulation;
from about 3% to about 6% of a stiffening agent component by weight of the formulation;
from about 7% to about 13% of an emollient component by weight of the formulation;
from about 3% to about 5% of an emulsifier component by weight of the formulation;
from about 0.3% to about 0.5% of a stabilizing agent component by weight of the formulation;
from about 20% to about 25% of a solvent component by weight of the formulation; and
about 1.5% of ruxolitinib, or a pharmaceutically acceptable salt thereof, by weight of the formulation on a free base basis.

In some embodiments, the pharmaceutical formulation comprises:
from about 45% to about 55% of water by weight of the formulation;
from about 5% to about 10% of an occlusive agent component by weight of the formulation;
from about 4% to about 7% of a stiffening agent component by weight of the formulation;
from about 7% to about 13% of an emollient component by weight of the formulation;
from about 4% to about 7% of an emulsifier component by weight of the formulation;
from about 0.3% to about 0.5% of a stabilizing agent component by weight of the formulation;
from about 20% to about 25% of a solvent component by weight of the formulation; and
about 1.5% of ruxolitinib, or a pharmaceutically acceptable salt thereof, by weight of the formulation on a free base basis.

In some embodiments, the pharmaceutical formulation comprises:
from about 45% to about 55% of water by weight of the formulation;
about 7% of an occlusive agent component by weight of the formulation;
from about 4.5% to about 5% of a stiffening agent component by weight of the formulation;
about 10% of an emollient component by weight of the formulation;
from about 4% to about 4.5% of an emulsifier component by weight of the formulation; about 0.4% of a stabilizing agent component by weight of the formulation;
about 22% of a solvent component by weight of the formulation; and about 1.5% of ruxolitinib, or a pharmaceutically acceptable salt thereof, by weight of the formulation on a free base basis.

In some embodiments, the combined amount of the stiffening agent component and the emulsifier component is at least about 8% by weight of the formulation.

In some embodiments:
the occlusive agent component comprises a petrolatum;
the stiffening agent component comprises one or more substances independently selected from one or more fatty alcohols;
the emollient component comprises one or more substances independently selected from mineral oils and triglycerides;
the emulsifier component comprises one or more substances independently selected from glyceryl fatty esters and sorbitan fatty esters;
the stabilizing agent component comprises one or more substances independently selected from polysaccharides; and
the solvent component comprises one or more substances independently selected from alkylene glycols and polyalkylene glycols.

In some embodiments:
the occlusive agent component comprises white petrolatum;
the stiffening agent component comprises one or more substances independently selected from cetyl alcohol and stearyl alcohol;
the emollient component comprises one or more substances independently selected from light mineral oil, medium chain triglycerides, and dimethicone;
the emulsifier component comprises one or more substances independently selected from glyceryl stearate and polysorbate 20;
the stabilizing agent component comprises xanthan gum; and
the solvent component comprises one or more substances independently selected from propylene glycol and polyethylene glycol.

In some embodiments, the pharmaceutical formulation further comprises an antimicrobial preservative component.

In some embodiments, the antimicrobial preservative component is present in an amount of about 0.05% to about 3% by weight of the formulation.

In some embodiments, the antimicrobial preservative component is present in an amount of about 0.1% to about 1% by weight of the formulation.

As used herein, the phrase "antimicrobial preservative component" is a substance or mixtures of substances which inhibits microbial growth in the formulation.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the pharmaceutical formulation further comprises a chelating agent component.

As used herein, the phrase "chelating agent component" refers to a compound or mixtures of compounds that has the ability to bind strongly with metal ions.

In some embodiments, the chelating agent component comprises edetate disodium.

As used herein, "% by weight of the formulation" means the percent concentration of the component in the formulation is on weight/weight basis. For example, 1% w/w of component A=[(mass of component A)/(total mass of the formulation)]×100.

As used herein, "% by weight of the formulation on a free base basis" of ruxolitinib, or pharmaceutically acceptable salt thereof" means that the % w/w is calculated based on the weight of ruxolitinib in the total formulation. For example, "0.5% w/w on a free base basis" of ruxolitinib phosphate means that for 100 grams of total formulation, there are 0.66 grams of ruxolitinib phosphate in the formulation (which equates to 0.5 grams of the free base, ruxolitinib).

In some embodiments, the components are present in exactly the ranges specified (e.g., the term "about" is not present). In some embodiments, "about" means plus or minus 10% of the value.

As will be appreciated, some components of the pharmaceutical formulations described herein can possess multiple functions. For example, a given substance may act as both an emulsifying agent component and a stabilizing agent. In some such cases, the function of a given component can be considered singular, even though its properties may allow multiple functionality. In some embodiments, each component of the formulation comprises a different substance or mixture of substances.

As used herein, the term "component" can mean one substance or a mixture of substances.

As used herein, the term "fatty acid" refers to an aliphatic acid that is saturated or unsaturated. In some embodiments, the fatty acid is in a mixture of different fatty acids. In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in combination with other terms, refers to a group of formula-O-alkylene-. In some embodiments, the polyalkylene glycol is polyethylene glycol.

As used herein, the term, "sorbitan fatty ester" includes products derived from sorbitan or sorbitol and fatty acids and, optionally, poly(ethylene glycol) units, including sorbitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxyethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyethylene units. In some embodiments, the polyoxyethylene portion of the compound or mixture has about 4 to about 80 oxyethylene units. In some embodiments, the polyoxyethylene portion of the compound or mixture has about 4 to about 40 oxyethylene units. In some embodiments, the polyoxyethylene portion of the compound or mixture has about 4 to about 20 oxyethylene units. Suitable polyethoxylated sorbitan esters include, but are not limited to the Tween™ series (available from Uniqema), which includes Tween 20 (POE (20) sorbitan monolaurate), 21 (POE (4) sorbitan monolaurate), 40 (POE (20) sorbitan monopalmitate), 60 (POE (20) sorbitan monostearate), 60K (POE (20) sorbitan monostearate), 61 (POE (4) sorbitan monostearate), 65 (POE (20) sorbitan tristearate), 80 (POE (20) sorbitan monooleate), 80K (POE (20) sorbitan monooleate), 81 (POE (5) sorbitan monooleate), and 85 (POE (20) sorbitan trioleate). As used herein, the abbreviation "POE" refers to polyoxyethylene. The number following the POE abbreviation refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the polyethoxylated sorbitan ester is a polysorbate. In some embodiments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suitable fatty acids for deriving glycerides of fatty acids include, but are not limited to, those described herein. In some embodiments, the glyceryl fatty ester is a mono-glyceride of a fatty acid having 12 to 18 carbon atoms. In some embodiments, the glyceryl fatty ester is glyceryl stearate.

As used herein, the term "triglycerides" refers to a triglyceride of a fatty acid. In some embodiments, the triglyceride is medium chain triglycerides.

As used herein, the term "alkylene glycol" refers to a group of formula-O-alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer.

In some embodiments of the methods described herein, the biological sample is blood, serum, plasma, urine, spinal fluid, saliva, lacrimal fluid, or sweat. In some embodiments, the biological sample is blood, serum, or plasma.

In some embodiments of the methods described herein, the concentration of the protein is measured by an immunological method (e.g., selected from the group consisting of enzyme-linked immunosorbent assay, enzyme immunoassay, radioimmunoassay, chemiluminescent immunoassay, electrochemiluminescence immunoassay, latex turbidimetric immunoassay, latex photometric immunoassay, immunochromatographic assay, and western blotting).

In some embodiments of the methods described herein, the concentration of the protein is measured by mass spectrometry.

The term "baseline concentration" of protein refers to the concentration of a protein in a subject prior to initiation of treatment with ruxolitinib.

The term "reduced concentration" means a concentration of the protein being analyzed that is lower than the concentration of that protein in a control or in a previous sample. For example, the concentration of the protein being analyzed can be at least 1.5, 2, 3, 4, 5, 6, 7, 8, 9, 10, 20, 25, 50, 75, or 100 times lower, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% lower, than the concentration of that protein in a control.

The term "increased concentration" means a concentration of the protein being analyzed that is higher than the concentration of that protein in a control or in a previous sample. For example, the concentration of the protein being analyzed can be at least 1.5, 2, 3, 4, 5, 6, 7, 8, 9, 10, 20, 25, 50, 75, or 100 times higher, or at least 10%, 20%, 30%, 40%, 50%, 60%, 70%, 80%, 90%, 100%, 200%, 300%, 400%, 500%, 600%, 700%, 800%, 900%, 1,000%, 1,500%, 2,000%, 2,500%, 3,000%, 3,500%, 4,000%, 4,500%, or 5,000% higher, than the concentration of that protein in a control.

The term "respond to a therapy" means that the subject administered with the therapy shows a positive response to ruxolitinib therapy provided.

Combination Therapies

One or more additional pharmaceutical agents such as, for example, anti-inflammatory agents, steroids, immunosuppressants, as well as Bcr-Abl, Flt-3, RAF and FAK kinase inhibitors such as, for example, those described in WO 2006/056399, or other agents can be used in combination with the formulations of the present invention for treatment of vitiligo. The one or more additional pharmaceutical agents can be administered to a patient simultaneously or sequentially.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the formulations of the invention can be used in combination with one or more other kinase inhibitors including imatinib, particularly for treating patients resistant to imatinib or other kinase inhibitors.

In some embodiments, a corticosteroid such as dexamethasone is administered to a patient in combination with the compound of the invention where the dexamethasone is administered intermittently as opposed to continuously.

The following embodiments are provided:
1. A method of treating vitiligo in a patient, comprising administering to the patient in need thereof a cream containing about 1.5% w/w ruxolitinib, or a pharmaceutically acceptable salt thereof, on a free base basis, twice per day.
2. The method of embodiment 1, wherein the cream contains 1.5% w/w ruxolitinib phosphate on a free base basis.
3. The method of any one of embodiments 1-2, wherein the patient achieves a 25% or greater improvement in Face Vitiligo Area Scoring Index.
4. The method of any one of embodiments 1-2, wherein the patient achieves a 50% or greater improvement in Face Vitiligo Area Scoring Index.

5. The method of any one of embodiments 1-2, wherein the patient achieves a 75% or greater improvement in Face Vitiligo Area Scoring Index.
6. The method of any one of embodiments 1-2, wherein the patient achieves a 90% or greater improvement in Face Vitiligo Area Scoring Index.
7. The method of any one of embodiments 1-6, wherein the patient achieves a 25% or greater improvement in Total Body Vitiligo Area Scoring Index.
8. The method of any one of embodiments 1-6, wherein the patient achieves a 50% or greater improvement in Total Body Vitiligo Area Scoring Index.
9. The method of any one of embodiments 1-6, wherein the patient achieves a 75% or greater improvement in Total Body Vitiligo Area Scoring Index.
10. The method of any one of embodiments 1-9, wherein the patient achieves a Facial Patient's Global Vitiligo Assessment response of 0 (no white patches) or 1 (mild) and at least a 1 point reduction from baseline.
11. The method of any one of embodiments 1-9, wherein the patient achieves a Facial Physician's Global Vitiligo Assessment of 0 (clear) or 1 (almost clear).
12. The method of any one of embodiments 1-9, wherein the patient achieves a Total Physician's Global Vitiligo Assessment of 0 (clear) or 1 (almost clear).
13. The method of any one of embodiments 1-9, wherein the patient achieves a Patient global impression of change for vitiligo of 1 (very much improved) or 2 (much improved).
14. The method of any one of embodiments 1-13, wherein the patient has a disease duration at baseline of at least 10 years.
15. The method of any one of embodiments 1-13, wherein the patient has a disease duration at baseline of at least 20 years.
16. The method of any one of embodiments 1-13, wherein the patient has progressive vitiligo at baseline.
17. The method of any one of embodiments 1-13, wherein the patient suffers from segmental vitiligo.
18. The method of any one of embodiments 1-17, wherein the administering is for up to 24 weeks.
19. The method of any one of embodiments 1-17, wherein the administering is for up to 52 weeks.
20. The method of embodiment 1, wherein the patient suffers from segmental vitiligo and achieves a 50% or greater improvement in Facial Vitiligo Area Scoring Index score at Week 52.
21. The method of embodiment 1, wherein the patient suffers from segmental vitiligo and achieves a 75% or greater improvement in Facial Vitiligo Area Scoring Index score at Week 52.
22. The method of any one of embodiments 1 and 20-21, wherein the patient suffers from segmental vitiligo and achieves a 50% or greater improvement in Total Body Vitiligo Area Scoring Index score at Week 52.
23. The method of embodiment 1, wherein the patient achieves a 25% or greater improvement in Vitiligo Area Scoring Index score on the upper extremities at Week 24.
24. The method of embodiment 1, wherein the patient achieves a 50% or greater improvement in Vitiligo Area Scoring Index score on the upper extremities at Week 24.
25. The method of embodiment 1, wherein the patient achieves a 75% or greater improvement in Vitiligo Area Scoring Index score on the upper extremities at Week 24.
26. The method of embodiment 1, wherein the patient achieves a 25% or greater improvement in Vitiligo Area Scoring Index score on the upper extremities at Week 52.
27. The method of embodiment 1, wherein the patient achieves a 50% or greater improvement in Vitiligo Area Scoring Index score on the upper extremities at Week 52.
28. The method of embodiment 1, wherein the patient achieves a 75% or greater improvement in Vitiligo Area Scoring Index score on the upper extremities at Week 52.
29. The method of embodiment 1, wherein the patient achieves a 25% or greater improvement in Vitiligo Area Scoring Index score on the lower extremities at Week 24.
30. The method of embodiment 1, wherein the patient achieves a 50% or greater improvement in Vitiligo Area Scoring Index score on the lower extremities at Week 24.
31. The method of embodiment 1, wherein the patient achieves a 75% or greater improvement in Vitiligo Area Scoring Index score on the lower extremities at Week 24.
32. The method of embodiment 1, wherein the patient achieves a 25% or greater improvement in Vitiligo Area Scoring Index score on the lower extremities at Week 52.
33. The method of embodiment 1, wherein the patient achieves a 50% or greater improvement in Vitiligo Area Scoring Index score on the lower extremities at Week 52.
34. The method of embodiment 1, wherein the patient achieves a 75% or greater improvement in Vitiligo Area Scoring Index score on the lower extremities at Week 52.
35. The method of embodiment 1, wherein the patient achieves a 25% or greater improvement in Vitiligo Area Scoring Index score on the hands at Week 24.
36. The method of embodiment 1, wherein the patient achieves a 50% or greater improvement in Vitiligo Area Scoring Index score on the hands at Week 24.
37. The method of embodiment 1, wherein the patient achieves a 75% or greater improvement in Vitiligo Area Scoring Index score on the hands at Week 24.
38. The method of embodiment 1, wherein the patient achieves a 25% or greater improvement in Vitiligo Area Scoring Index score on the hands at Week 52.
39. The method of embodiment 1, wherein the patient achieves a 50% or greater improvement in Vitiligo Area Scoring Index score on the hands at Week 52.
40. The method of embodiment 1, wherein the patient achieves a 75% or greater improvement in Vitiligo Area Scoring Index score on the hands at Week 52.
41. The method of embodiment 1, wherein the patient achieves a 25% or greater improvement in Vitiligo Area Scoring Index score on the feet at Week 24.
42. The method of embodiment 1, wherein the patient achieves a 50% or greater improvement in Vitiligo Area Scoring Index score on the feet at Week 24.
43. The method of embodiment 1, wherein the patient achieves a 75% or greater improvement in Vitiligo Area Scoring Index score on the feet at Week 24.
44. The method of embodiment 1, wherein the patient achieves a 25% or greater improvement in Vitiligo Area Scoring Index score on the feet at Week 52.

45. The method of embodiment 1, wherein the patient achieves a 50% or greater improvement in Vitiligo Area Scoring Index score on the feet at Week 52.
46. The method of embodiment 1, wherein the patient achieves a 75% or greater improvement in Vitiligo Area Scoring Index score on the feet at Week 52.
47. The method of any one of embodiments 1-46, wherein the cream is an oil-in-water emulsion.
48. The method of any one of embodiments 1-47, wherein the cream has a pH of about 2.8 to about 3.9.
49. The method of any one of embodiments 1-48, wherein the patient has a % facial body surface area affected by vitiligo (F-BSA) of greater than 1.5%.
50. The method of any one of embodiments 1-48, wherein the patient has a % facial body surface area affected by vitiligo (F-BSA) of greater than 1.5% and achieves a 50% or greater improvement in Facial Vitiligo Area Scoring Index score at Week 24.
51. The method of any one of embodiments 1-50, wherein the patient is an individual aged 50 years old or less.
52. The method of any one of embodiments 1-51, wherein the patient is female.
53. The method of any one of embodiments 1-52, wherein the patient previously received phototherapy.
54. A method of treating vitiligo in a patient comprising administering to the patient in need thereof a cream containing about 1.5% w/w ruxolitinib, or a pharmaceutically acceptable salt thereof, on a free base basis, twice per day.
55. The method of embodiment 54 wherein the cream contains 1.5% w/w ruxolitinib phosphate on a free base basis.
56. The method of embodiment 54 wherein patients achieve a 25% or greater improvement in Face Vitiligo Area Scoring Index.
57. The method of embodiment 54 wherein patients achieve a 50% or greater improvement in Face Vitiligo Area Scoring Index.
58. The method of embodiment 54 wherein patients achieve a 75% or greater improvement in Face Vitiligo Area Scoring Index.
59. The method of embodiment 54 wherein patients achieve a 90% or greater improvement in Face Vitiligo Area Scoring Index.
60. The method of embodiment 54 wherein patients achieve a 25% or greater improvement in Total Body Vitiligo Area Scoring Index.
61. The method of embodiment 54 wherein patients achieve a 50% or greater improvement in Total Body Vitiligo Area Scoring Index.
62. The method of embodiment 54 wherein patients achieve a 75% or greater improvement in Total Body Vitiligo Area Scoring Index.
63. The method of embodiment 54 wherein patients achieve a Facial Patient's Global Vitiligo Assessment response of 0 (no white patches) or 1 (mild) and at least a 1 point reduction from baseline.
64. The method of embodiment 54 wherein patients achieve a Facial Physician's Global Vitiligo Assessment of 0 (clear) or 1 (almost clear).
65. The method of embodiment 54 wherein patients achieve a Total Physician's Global Vitiligo Assessment of 0 (clear) or 1 (almost clear).
66. The method of embodiment 54 wherein patients achieve a Patient global impression of change for vitiligo of 1 (very much improved) or 2 (much improved).
67. A method of treating vitiligo in a patient comprising administering to the patient in need thereof a cream containing about 1.5% w/w ruxolitinib, or a pharmaceutically acceptable salt thereof, on a free base basis, once per day.
68. The method of embodiment 67 wherein the cream contains 1.5% w/w ruxolitinib phosphate on a free base basis.
69. The method of embodiment 67 wherein patients achieve a 25% or greater improvement in Face Vitiligo Area Scoring Index.
70. The method of embodiment 67 wherein patients achieve a 50% or greater improvement in Face Vitiligo Area Scoring Index.
71. The method of embodiment 67 wherein patients achieve a 75% or greater improvement in Face Vitiligo Area Scoring Index.
72. The method of embodiment 67 wherein patients achieve a 90% or greater improvement in Face Vitiligo Area Scoring Index.
73. The method of embodiment 67 wherein patients achieve a 25% or greater improvement in Total Body Vitiligo Area Scoring Index.
74. The method of embodiment 67 wherein patients achieve a 50% or greater improvement in Total Body Vitiligo Area Scoring Index.
75. The method of embodiment 67 wherein patients achieve a 75% or greater improvement in Total Body Vitiligo Area Scoring Index.
76. The method of embodiment 67 wherein patients achieve a Facial Patient's Global Vitiligo Assessment response of 0 (no white patches) or 1 (mild) and at least a 1 point reduction from baseline.
77. The method of embodiment 67 wherein patients achieve a Facial Physician's Global Vitiligo Assessment of 0 (clear) or 1 (almost clear).
78. The method of embodiment 67 wherein patients achieve a Total Physician's Global Vitiligo Assessment of 0 (clear) or 1 (almost clear).
79. The method of embodiment 67 wherein patients achieve a Patient global impression of change for vitiligo of 1 (very much improved) or 2 (much improved).
80. A method of treating vitiligo in a patient comprising administering to the patient in need thereof a cream containing about 0.5% w/w ruxolitinib, or a pharmaceutically acceptable salt thereof, on a free base basis, once per day.
81. The method of embodiment 80 wherein the cream contains 0.5% w/w ruxolitinib phosphate on a free base basis.
82. The method of embodiment 80 wherein patients achieve a 25% or greater improvement in Face Vitiligo Area Scoring Index.
83. The method of embodiment 80 wherein patients achieve a 50% or greater improvement in Face Vitiligo Area Scoring Index.
84. The method of embodiment 80 wherein patients achieve a 75% or greater improvement in Face Vitiligo Area Scoring Index.
85. The method of embodiment 80 wherein patients achieve a 90% or greater improvement in Face Vitiligo Area Scoring Index.
86. The method of embodiment 80 wherein patients achieve a 25% or greater improvement in Total Body Vitiligo Area Scoring Index.

87. The method of embodiment 80 wherein patients achieve a 50% or greater improvement in Total Body Vitiligo Area Scoring Index.
88. The method of embodiment 80 wherein patients achieve a 75% or greater improvement in Total Body Vitiligo Area Scoring Index.
89. The method of embodiment 80 wherein patients achieve a Facial Patient's Global Vitiligo Assessment response of 0 (no white patches) or 1 (mild) and at least a 1 point reduction from baseline.
90. The method of embodiment 80 wherein patients achieve a Facial Physician's Global Vitiligo Assessment of 0 (clear) or 1 (almost clear).
91. The method of embodiment 80 wherein patients achieve a Total Physician's Global Vitiligo Assessment of 0 (clear) or 1 (almost clear).
92. The method of embodiment 80 wherein patients achieve a Patient global impression of change for vitiligo of 1 (very much improved) or 2 (much improved).
93. A method of treating vitiligo in a patient comprising administering to the patient in need thereof a cream containing about 0.15% w/w ruxolitinib, or a pharmaceutically acceptable salt thereof, on a free base basis, once per day.
94. The method of embodiment 93 wherein the cream contains 0.15% w/w ruxolitinib phosphate on a free base basis.
95. The method of embodiment 93 wherein patients achieve a 25% or greater improvement in Face Vitiligo Area Scoring Index.
96. The method of embodiment 93 wherein patients achieve a 50% or greater improvement in Face Vitiligo Area Scoring Index.
97. The method of embodiment 93 wherein patients achieve a 75% or greater improvement in Face Vitiligo Area Scoring Index.
98. The method of embodiment 93 wherein patients achieve a 90% or greater improvement in Face Vitiligo Area Scoring Index.
99. The method of embodiment 93 wherein patients achieve a 25% or greater improvement in Total Body Vitiligo Area Scoring Index.
100. The method of embodiment 93 wherein patients achieve a 50% or greater improvement in Total Body Vitiligo Area Scoring Index.
101. The method of embodiment 93 wherein patients achieve a 75% or greater improvement in Total Body Vitiligo Area Scoring Index.
102. The method of embodiment 93 wherein patients achieve a Facial Patient's Global Vitiligo Assessment response of 0 (no white patches) or 1 (mild) and at least a 1 point reduction from baseline.
103. The method of embodiment 93 wherein patients achieve a Facial Physician's Global Vitiligo Assessment of 0 (clear) or 1 (almost clear).
104. The method of embodiment 93 wherein patients achieve a Total Physician's Global Vitiligo Assessment of 0 (clear) or 1 (almost clear).
105. The method of embodiment 93 wherein patients achieve a Patient global impression of change for vitiligo of 1 (very much improved) or 2 (much improved).
106. A method of treating vitiligo in a patient comprising topically administering to affected skin area of the patient in need thereof a pharmaceutical composition containing about 1.5% w/w ruxolitinib, or a pharmaceutically acceptable salt thereof, on a free base basis, twice per day.
107. The method of embodiment 106, wherein the vitiligo is generalized vitiligo.
108. A method of treating vitiligo in a patient comprising topically administering to an affected skin area of the patient in need thereof a pharmaceutical composition containing about 1.5% w/w ruxolitinib, or a pharmaceutically acceptable salt thereof, on a free base basis, twice per day, wherein the affected area is selected from lower extremities, trunk, hands, upper extremities, and feet.
109. The method of embodiment 108, wherein the affected skin area is the lower extremities of the patient.
110. The method of embodiment 108, wherein the affected skin area is the trunk of the patient.
111. The method of embodiment 108, wherein the affected skin area is the hands of the patient.
112. The method of embodiment 108, wherein the affected skin area is the upper extremities of the patient.
113. The method of embodiment 108, wherein the affected skin area is the feet of the patient.
114. The method of any one of embodiments 108-113, wherein the patient achieves a 25% or greater improvement in Vitiligo Area Scoring Index on the affected skin area.
115. The method of any one of embodiments 108-114, wherein the patient achieves a 50% or greater improvement in Vitiligo Area Scoring Index on the affected skin area.
116. The method of any one of embodiments 108-115, wherein the patient achieves a 75% or greater improvement in Vitiligo Area Scoring Index on the affected skin area.
117. The method of any one of embodiments 108-116, wherein the patient achieves a 50% or greater improvement in Vitiligo Area Scoring Index score on the hands of the patient at Week 4, Week 8, Week 18, Week 24, Week 32, Week 38, Week 42, Week 48, or Week 52.
118. The method of any one of embodiments 108-117, wherein the patient achieves a 50% or greater improvement in Vitiligo Area Scoring Index score on the upper extremities of the patient at Week 4, Week 8, Week 18, Week 24, Week 32, Week 38, Week 42, Week 48, or Week 52.
119. The method of any one of embodiments 108-118, wherein the patient achieves a 50% or greater improvement in Vitiligo Area Scoring Index score on the feet of the patient at Week 4, Week 8, Week 18, Week 24, Week 32, Week 38, Week 42, Week 48, or Week 52.
120. The method of any one of embodiments 108-119, wherein the patient achieves a 50% or greater improvement in Vitiligo Area Scoring Index score on the lower extremities of the patient at Week 4, Week 8, Week 18, Week 24, Week 32, Week 38, Week 42, Week 48, or Week 52.
121. The method of any one of embodiments 108-120, wherein the patient achieves a 50% or greater improvement in Vitiligo Area Scoring Index score on the trunk of the patient at Week 4, Week 8, Week 18, Week 24, Week 32, Week 38, Week 42, Week 48, or Week 52.
122. The method of embodiment 108, wherein:
the affected area is selected from lower extremities, trunk, hands, upper extremities, and feet;
the patient suffers from generalized vitiligo with depigmented area of: (i) 0.5% or greater body surface area (BSA) on the face, (ii) 3% or greater BSA on non-facial areas, and (iii) not exceeding 10% BSA on total body area;

the method does not comprise administering laser or any kind of phototherapy; and the patient achieves a 50% or greater improvement in Vitiligo Area Scoring Index score on the affected skin area.

123. The method of embodiment 108, wherein:

the affected area is selected from lower extremities, trunk, and feet;

the patient suffers from generalized vitiligo with depigmented area of: (i) 0.5% or greater body surface area (BSA) on the face, (ii) 3% or greater BSA on non-facial areas, and (iii) not exceeding 10% BSA on total body area;

the method does not comprise administering laser or any kind of phototherapy; and the patient achieves a 50% or greater improvement in Vitiligo Area Scoring Index score on the affected skin area.

124. A method of treating generalized vitiligo in a patient comprising topically administering to an affected skin area of the patient in need thereof a pharmaceutical composition containing about 1.5% w/w ruxolitinib, or a pharmaceutically acceptable salt thereof, on a free base basis, twice per day, wherein the patient has a vitiligo disease duration of at least 20 years and wherein the patient achieves a 50% or greater improvement in Face Vitiligo Scoring Index.

125. The method of embodiment 124, wherein the affected area is face.

126. The method of embodiment 124, wherein the affected area is head and neck 127. The method of embodiment 124, wherein the affected area is selected from lower extremities, trunk, hands, upper extremities, and feet.

128. A method of treating vitiligo in a patient, comprising topically administering to an affected skin area of the patient in need thereof a pharmaceutical composition containing about 1.5% w/w ruxolitinib, or a pharmaceutically acceptable salt thereof, on a free base basis, twice per day, wherein the patient does not receive phototherapy for vitiligo during the administration of the pharmaceutical composition.

129. The method of any one of embodiments 106-128, wherein the patient achieves a 25% or greater improvement in Face Vitiligo Area Scoring Index.

130. The method of any one of embodiments 106-129, wherein the patient achieves a 50% or greater improvement in Face Vitiligo Area Scoring Index.

131. The method of any one of embodiments 106-130, wherein the patient achieves a 75% or greater improvement in Face Vitiligo Area Scoring Index.

132. The method of any one of embodiments 106-131, wherein the patient achieves a 90% or greater improvement in Face Vitiligo Area Scoring Index.

133. The method of any one of embodiments 106-132, wherein the patient achieves a 25% or greater improvement in Total Body Vitiligo Area Scoring Index.

134. The method of any one of embodiments 106-133, wherein the patient achieves a 50% or greater improvement in Total Body Vitiligo Area Scoring Index.

135. The method of any one of embodiments 106-134, wherein the patient achieves a 75% or greater improvement in Total Body Vitiligo Area Scoring Index.

136. The method of any one of embodiments 106-135, wherein the administering is for up to 24 weeks.

137. The method of any one of embodiments 106-136, wherein the administering is for up to 52 weeks.

138. The method of any one of embodiments 106-137, wherein the patient has at least 1.5% facial body surface area affected by vitiligo (F-BSA).

139. The method of any one of embodiments 106-138, wherein the patient has at least 1.5% facial body surface area affected by vitiligo (F-BSA) and achieves a 50% or greater improvement in Face Vitiligo Area Scoring Index score at Week 24.

140. The method of any one of embodiments 106-139, wherein the patient has 1.5% facial body surface area affected by vitiligo (F-BSA) and achieves a 50% or greater improvement in Face Vitiligo Area Scoring Index score at Week 52.

141. The method of any one of embodiments 106-140, wherein the patient has 1.5% facial body surface area affected by vitiligo (F-BSA) and achieves a 75% or greater improvement in Face Vitiligo Area Scoring Index score at Week 24.

142. The method of any one of embodiments 106-141, wherein the patient has at least 1.5% facial body surface area affected by vitiligo (F-BSA) and achieves a 75% or greater improvement in Face Vitiligo Area Scoring Index score at Week 52.

143. The method of any one of embodiments 106-142, wherein the patient achieves a 25% or greater improvement in Total Body Vitiligo Area Scoring Index score at Week 24.

144. The method of any one of embodiments 106-143, wherein the patient achieves a 25% or greater improvement in Total Body Vitiligo Area Scoring Index score at Week 52.

145. The method of any one of embodiments 106-144, wherein the patient achieves a 50% or greater improvement in Total Body Vitiligo Area Scoring Index score at Week 24.

146. The method of any one of embodiments 106-145, wherein the patient achieves a 50% or greater improvement in Total Body Vitiligo Area Scoring Index score at Week 52.

147. The method of any one of embodiments 106-146, wherein the patient achieves a 75% or greater improvement in Total Body Vitiligo Area Scoring Index score at Week 24.

148. The method of any one of embodiments 106-147, wherein the patient achieves a 75% or greater improvement in Total Body Vitiligo Area Scoring Index score at Week 52.

149. The method of any one of embodiments 106-148, wherein the patients has no greater than 10% total body surface area affected by vitiligo (T-BSA).

150. The method of any one of embodiments 106-149, wherein the patient has been clinically diagnosed with vitiligo.

151. The method of any one of embodiments 106-150, wherein the patient is aged 12 years old and older.

152. The method of any one of embodiments 106-150, wherein the patient is aged 18 years old and older.

153. The method of any one of embodiments 106-150, wherein the patient is 18 years old to 75 years old.

154. The method of any one of embodiments 106-150, wherein the patient is aged 50 years old or less.

155. The method of any one of embodiments 106-154, wherein the patient has progressive vitiligo at baseline.

156. The method of any one of embodiments 106-155, wherein the patient has at least 0.5% facial body surface area affected by vitiligo.

157. The method of any one of embodiments 106-156, wherein the patient has at least 3% non-facial body surface area affected by vitiligo.

158. The method of any one of embodiments 106-157, wherein the patient has no greater than 10% total body surface area affected by vitiligo.

159. The method of any one of embodiments 106-158, wherein the patient has a disease duration at baseline of at least 10 years.

160. The method of any one of embodiments 106-159, wherein the patient does not administer any other agents for the treatment of vitiligo.

161. The method of any one of embodiments 106-160, wherein the patient previously received phototherapy.

162. The method of any one of embodiments 106-161, wherein the method does not comprise administering laser or any kind of phototherapy.

163. The method of any one of embodiments 106-162, wherein a hemoglobin level of the patient at Week 52 is similar to a hemoglobin level of the patient at baseline.

164. The method of any one of embodiments 106-163, wherein a platelet level of the patient at Week 52 is similar to a platelet level of the patient at baseline.

165. The method of any one of embodiments 106-164, wherein there is no substantial difference in response between patients having baseline total body surface area affected by vitiligo equal to or less than 20% and patients having baseline total body surface area affected by vitiligo greater than 20%.

166. The method of any one of embodiments 106-165, wherein the ruxolitinib, or the pharmaceutically acceptable salt thereof, is ruxolitinib phosphate.

167. The method of any one of embodiments 106-166, wherein the pharmaceutical composition is a cream.

168. The method of embodiment 167, wherein the cream is an oil-in-water emulsion.

169. The method of embodiment 168, wherein the cream contains 1.5% w/w ruxolitinib phosphate on a free base basis.

170. The method of embodiment 169, wherein the cream has a pH of about 2.8 to about 3.9.

171. The method of embodiment 106, wherein the vitiligo is segmental vitiligo.

172. A pharmaceutical composition for use in any of the methods of embodiments 106-171.

173. Use of a pharmaceutical composition for preparation of medicament for use in any of the methods of embodiments 106-171.

174. A method of treating vitiligo in a patient comprising topically administering to an affected skin area of the patient in need thereof a pharmaceutical composition containing about 1.5% w/w ruxolitinib, or a pharmaceutically acceptable salt thereof, on a free base basis, twice per day, wherein the affected area is selected from lower extremities, trunk, hands, upper extremities, and feet.

175. The method of embodiment 174, wherein the ruxolitinib, or the pharmaceutically acceptable salt thereof, is ruxolitinib phosphate.

176. The method of embodiment 174, wherein the method does not comprise administering laser or any kind of phototherapy.

177. The method of embodiment 174, wherein the affected skin area is the lower extremities of the patient.

178. The method of embodiment 174, wherein the affected skin area is the trunk of the patient.

179. The method of embodiment 174, wherein the affected skin area is the hands of the patient.

180. The method of embodiment 174, wherein the affected skin area is the upper extremities of the patient.

181. The method of embodiment 174, wherein the affected skin area is the feet of the patient. 182. The method of embodiment 174, wherein the patient achieves a 25% or greater improvement in Vitiligo Area Scoring Index on the affected skin area.

183. The method of embodiment 174, wherein the patient achieves a 50% or greater improvement in Vitiligo Area Scoring Index on the affected skin area.

184. The method of embodiment 174, wherein the patient achieves a 75% or greater improvement in Vitiligo Area Scoring Index on the affected skin area.

185. The method of embodiment 174, wherein the patient has at least 0.5% facial body surface area affected by vitiligo.

186. The method of embodiment 174, wherein the patient has at least 3% non-facial body surface area affected by vitiligo.

187. The method of embodiment 174, wherein the patient has at least 0.5% facial body surface area affected by vitiligo and at least 3% non-facial body surface area affected by vitiligo.

188. The method of embodiment 174, wherein the patient has been clinically diagnosed with vitiligo.

189. The method of embodiment 174, wherein the patient does not administer any other agents for the treatment of vitiligo.

190. The method of embodiment 174, wherein the patient is 18 years old to 75 years old.

191. The method of embodiment 174, wherein the patient achieves a 25% or greater improvement in Vitiligo Area Scoring Index score on the hands of the patient at Week 4, Week 8, Week 18, Week 24, Week 32, Week 38, Week 42, Week 48, or Week 52.

192. The method of embodiment 174, wherein the patient achieves a 25% or greater improvement in Vitiligo Area Scoring Index score on the upper extremities of the patient at Week 4, Week 8, Week 18, Week 24, Week 32, Week 38, Week 42, Week 48, or Week 52.

193. The method of embodiment 174, wherein the patient achieves a 25% or greater improvement in Vitiligo Area Scoring Index score on the feet of the patient at Week 4, Week 8, Week 18, Week 24, Week 32, Week 38, Week 42, Week 48, or Week 52.

194. The method of embodiment 174, wherein the patient achieves a 25% or greater improvement in Vitiligo Area Scoring Index score on the lower extremities of the patient at Week 4, Week 8, Week 18, Week 24, Week 32, Week 38, Week 42, Week 48, or Week 52.

195. The method of embodiment 174, wherein the patient achieves a 25% or greater improvement in Vitiligo Area Scoring Index score on the trunk of the patient at Week 4, Week 8, Week 18, Week 24, Week 32, Week 38, Week 42, Week 48, or Week 52.

196. The method of embodiment 174, wherein the patient achieves a 50% or greater improvement in Vitiligo Area Scoring Index score on the hands of the patient at Week 4, Week 8, Week 18, Week 24, Week 32, Week 38, Week 42, Week 48, or Week 52.

197. The method of embodiment 174, wherein the patient achieves a 50% or greater improvement in Vitiligo Area Scoring Index score on the upper extremities of the patient at Week 4, Week 8, Week 18, Week 24, Week 32, Week 38, Week 42, Week 48, or Week 52.
198. The method of embodiment 174, wherein the patient achieves a 50% or greater improvement in Vitiligo Area Scoring Index score on the feet of the patient at Week 4, Week 8, Week 18, Week 24, Week 32, Week 38, Week 42, Week 48, or Week 52.
199. The method of embodiment 174, wherein the patient achieves a 50% or greater improvement in Vitiligo Area Scoring Index score on the lower extremities of the patient at Week 4, Week 8, Week 18, Week 24, Week 32, Week 38, Week 42, Week 48, or Week 52.
200. The method of embodiment 174, wherein the patient achieves a 50% or greater improvement in Vitiligo Area Scoring Index score on the trunk of the patient at Week 4, Week 8, Week 18, Week 24, Week 32, Week 38, Week 42, Week 48, or Week 52.
201. The method of embodiment 174, wherein the patient achieves a 75% or greater improvement in Vitiligo Area Scoring Index score on the lower extremities, upper extremities, feet, hands, or trunk of the patient at Week 4, Week 8, Week 18, Week 24, Week 32, Week 38, Week 42, Week 48, or Week 52.
202. The method of embodiment 174, wherein the pharmaceutical composition is a cream.
203. The method of embodiment 202, wherein the cream is an oil-in-water emulsion.
204. The method of embodiment 203, wherein the cream contains 1.5% w/w ruxolitinib phosphate on a free base basis.
205. The method of embodiment 204, wherein the cream has a pH of about 2.8 to about 3.9.
206. The method of embodiment 174, wherein there is no substantial difference in response between patients having baseline total body surface area affected by vitiligo (T-BSA) equal to or less than 20% and patients having baseline T-BSA greater than 20%.
207. A method of treating generalized vitiligo in a patient comprising topically administering to an affected skin area of the patient in need thereof a cream comprising 1.5% w/w ruxolitinib phosphate on a free base basis, twice per day, wherein:
the affected area is selected from lower extremities, trunk, hands, upper extremities, and feet;
the patient is aged 18 or older;
the patient suffers from generalized vitiligo with depigmented area of: (i) 0.5% or greater body surface area (BSA) on the face, (ii) 3% or greater BSA on non-facial areas, and (iii) not exceeding 10% BSA on total body area;
the method does not comprise administering laser or any kind of phototherapy; and
the patient achieves a 50% or greater improvement in Vitiligo Area Scoring Index score on the affected skin area.
208. A method of treating generalized vitiligo in a patient comprising topically administering to an affected skin area of the patient in need thereof a cream comprising 1.5% w/w ruxolitinib phosphate on a free base basis, twice per day, wherein:
the affected area is selected from lower extremities, trunk, and feet;
the patient is aged 18 or older;
the patient suffers from generalized vitiligo with depigmented area of: (i) 0.5% or greater body surface area (BSA) on the face, (ii) 3% or greater BSA on non-facial areas, and (iii) not exceeding 10% BSA on total body area;
the method does not comprise administering laser or any kind of phototherapy; and
the patient achieves a 50% or greater improvement in Vitiligo Area Scoring Index score on the affected skin area.
209. A method of treating generalized vitiligo in a patient comprising topically administering to an affected skin area of the patient in need thereof a pharmaceutical composition containing about 1.5% w/w ruxolitinib, or a pharmaceutically acceptable salt thereof, on a free base basis, twice per day, wherein the patient has a vitiligo disease duration of at least 20 years and wherein the patient achieves a 50% or greater improvement in Face Vitiligo Scoring Index.
210. The method of embodiment 209, wherein the ruxolitinib, or the pharmaceutically acceptable salt thereof, is ruxolitinib phosphate.
211. The method of embodiment 209, wherein the pharmaceutical composition is a cream.
212. The method of embodiment 211, wherein the cream is an oil-in-water emulsion.
213. The method of embodiment 212, wherein the cream contains 1.5% w/w ruxolitinib phosphate on a free base basis.
214. The method of embodiment 213 wherein the cream has a pH of about 2.8 to about 3.9.
215. The method of embodiment 209, wherein the patient has at least 0.5% facial body surface area affected by vitiligo.
216. The method of embodiment 209, wherein the patient has at least 3% non-facial body surface area affected by vitiligo.
217. The method of embodiment 209, wherein the patient suffers from generalized vitiligo with depigmented area of: (i) at least 0.5% facial body surface area affected by vitiligo and (ii) at least 3% non-facial body surface area affected by vitiligo.
218. The method of embodiment 209, wherein the patient has no greater than 10% total body surface area affected by vitiligo.
219. The method of embodiment 209, wherein the patient achieves a 75% or greater improvement in Face Vitiligo Area Scoring Index.
220. The method of embodiment 209, wherein the patient achieves a 90% or greater improvement in Face Vitiligo Area Scoring Index.
221. The method of embodiment 209, wherein the patient achieves a 25% or greater improvement in Total Body Vitiligo Area Scoring Index.
222. The method of embodiment 209, wherein the patient achieves a 50% or greater improvement in Total Body Vitiligo Area Scoring Index.
223. The method of embodiment 209, wherein the patient achieves a 75% or greater improvement in Total Body Vitiligo Area Scoring Index.
224. The method of embodiment 209, wherein the patient has at least 1.5% facial body surface area affected by vitiligo.
225. The method of embodiment 209, wherein the patient has at least 1.5% facial body surface area affected by vitiligo and achieves a 50% or greater improvement in Face Vitiligo Area Scoring Index score at Week 24.

226. The method of embodiment 209, wherein the patient has at least 1.5% facial body surface area affected by vitiligo and achieves a 50% or greater improvement in Face Vitiligo Area Scoring Index score at Week 52.
227. The method of embodiment 209, wherein the patient has at least 1.5% facial body surface area affected by vitiligo and achieves a 75% or greater improvement in Face Vitiligo Area Scoring Index score at Week 24.
228. The method of embodiment 209, wherein the patient has at least 1.5% facial body surface area affected by vitiligo and achieves a 75% or greater improvement in Face Vitiligo Area Scoring Index score at Week 52.
229. The method of embodiment 209, wherein the patient achieves a 25% or greater improvement in Total Body Vitiligo Area Scoring Index score at Week 24.
230. The method of embodiment 209, wherein the patient achieves a 25% or greater improvement in Total Body Vitiligo Area Scoring Index score at Week 52.
231. The method of embodiment 209, wherein the patient achieves a 50% or greater improvement in Total Body Vitiligo Area Scoring Index score at Week 24.
232. The method of embodiment 209, wherein the patient achieves a 50% or greater improvement in Total Body Vitiligo Area Scoring Index score at Week 52.
233. The method of embodiment 209, wherein the patient achieves a 75% or greater improvement in Total Body Vitiligo Area Scoring Index score at Week 24.
234. The method of embodiment 209, wherein the patient achieves a 75% or greater improvement in Total Body Vitiligo Area Scoring Index score at Week 52.
235. The method of embodiment 209, wherein the patient has been clinically diagnosed with vitiligo.
236. The method of embodiment 209, wherein the patient does not administer any other agents for the treatment of vitiligo.
237. The method of embodiment 209, wherein the patient is 18 years old to 75 years old.
238. The method of embodiment 209, wherein the patient is aged 50 years old or less.
239. The method of embodiment 209, wherein the patient previously received phototherapy.
240. The method of embodiment 209, wherein the method does not comprise administering laser or any kind of phototherapy.
241. The method of embodiment 209, wherein a hemoglobin level of the patient at Week 52 is similar to a hemoglobin level of the patient observed at baseline.
242. The method of embodiment 209, wherein a platelet level of the patient at Week 52 is similar to a platelet level of the patient observed at baseline.
243. The method of embodiment 209, wherein there is no substantial difference in response between patients having baseline total body surface area equal to or less than 20% and patients having baseline total body surface area greater than 20%.
244. The method of embodiment 209, wherein the affected area is face.
245. The method of embodiment 209, wherein the affected area is head and neck.
246. The method of embodiment 209, wherein the affected area is selected from lower extremities, trunk, hands, upper extremities, and feet.
247. The method of embodiment 209, wherein the patient does not receive phototherapy for vitiligo during the administration of the pharmaceutical composition.
248. The method of embodiment 209, wherein the patient has progressive vitiligo at baseline.
249. A method of treating generalized vitiligo in a patient, comprising topically administering to an affected skin area of the patient in need thereof a pharmaceutical composition containing about 1.5% w/w ruxolitinib, or a pharmaceutically acceptable salt thereof, on a free base basis, twice per day.
250. A method of treating vitiligo in a patient, comprising topically administering to an affected skin area of the patient in need thereof a pharmaceutical composition containing about 1.5% w/w ruxolitinib, or a pharmaceutically acceptable salt thereof, on a free base basis, twice per day, wherein the patient does not receive phototherapy for vitiligo during the administration of the pharmaceutical composition.
251. The method of embodiment 249 or 250, wherein the ruxolitinib, or the pharmaceutically acceptable salt thereof, is ruxolitinib phosphate.
252. The method of embodiment 249 or 250, wherein the patient achieves a 25% or greater improvement in Face Vitiligo Area Scoring Index.
253. The method of embodiment 249 or 250, wherein the patient achieves a 50% or greater improvement in Face Vitiligo Area Scoring Index.
254. The method of embodiment 249 or 250, wherein the patient achieves a 75% or greater improvement in Face Vitiligo Area Scoring Index.
255. The method of embodiment 249 or 250, wherein the patient achieves a 90% or greater improvement in Face Vitiligo Area Scoring Index.
256. The method of embodiment 249 or 250, wherein the patient achieves a 25% or greater improvement in Total Body Vitiligo Area Scoring Index.
257. The method of embodiment 249 or 250, wherein the patient achieves a 50% or greater improvement in Total Body Vitiligo Area Scoring Index.
258. The method of embodiment 249 or 250, wherein the patient achieves a 75% or greater improvement in Total Body Vitiligo Area Scoring Index.
259. The method of embodiment 249 or 250, wherein the administering is for up to 24 weeks.
260. The method of embodiment 249 or 250, wherein the administering is for up to 52 weeks.
261. The method of embodiment 249 or 250, wherein the patient has at least 1.5% facial body surface area affected by vitiligo.
262. The method of embodiment 249 or 250, wherein the patient has at least 1.5% facial body surface area affected by vitiligo and achieves a 50% or greater improvement in Face Vitiligo Area Scoring Index score at Week 24.
263. The method of embodiment 249 or 250, wherein the patient has 1.5% facial body surface area affected by vitiligo and achieves a 50% or greater improvement in Face Vitiligo Area Scoring Index score at Week 52.
264. The method of embodiment 249 or 250, wherein the patient has 1.5% facial body surface area affected by vitiligo and achieves a 75% or greater improvement in Face Vitiligo Area Scoring Index score at Week 24.
265. The method of embodiment 249 or 250, wherein the patient has at least 1.5% facial body surface area affected by vitiligo and achieves a 75% or greater improvement in Face Vitiligo Area Scoring Index score at Week 52.
266. The method of embodiment 249 or 250, wherein the patient achieves a 25% or greater improvement in Total Body Vitiligo Area Scoring Index score at Week 24.

267. The method of embodiment 249 or 250, wherein the patient achieves a 25% or greater improvement in Total Body Vitiligo Area Scoring Index score at Week 52.
268. The method of embodiment 249 or 250, wherein the patient achieves a 50% or greater improvement in Total Body Vitiligo Area Scoring Index score at Week 24.
269. The method of embodiment 249 or 250, wherein the patient achieves a 50% or greater improvement in Total Body Vitiligo Area Scoring Index score at Week 52.
270. The method of embodiment 249 or 250, wherein the patient achieves a 75% or greater improvement in Total Body Vitiligo Area Scoring Index score at Week 24.
271. The method of embodiment 249 or 250, wherein the patient achieves a 75% or greater improvement in Total Body Vitiligo Area Scoring Index score at Week 52.
272. The method of embodiment 249 or 250, wherein the patients has no greater than 10% total body surface area affected by vitiligo.
273. The method of embodiment 249 or 250, wherein the pharmaceutical composition is a cream.
274. The method of embodiment 273, wherein the cream is an oil-in-water emulsion.
275. The method of embodiment 274, wherein the cream contains 1.5% w/w ruxolitinib phosphate on a free base basis.
276. The method of embodiment 275, wherein the cream has a pH of about 2.8 to about 3.9.
277. The method of embodiment 249 or 250, wherein the patient is aged 50 years old or less.
278. The method of embodiment 249 or 250, wherein the patient has progressive vitiligo at baseline.
279. The method of embodiment 249 or 250, wherein the patient previously received phototherapy.
280. The method of embodiment 249 or 250, wherein a hemoglobin level of the patient at Week 52 is similar to a hemoglobin level of the patient at baseline.
281. The method of embodiment 249 or 250, wherein a platelet level of the patient at Week 52 is similar to a platelet level of the patient at baseline.
282. The method of embodiment 249 or 250, wherein there is no substantial difference in response between patients having baseline total body surface area score equal to or less than 20% and patients having baseline total body surface area score greater than 20%.
283. The method of embodiment 249 or 250, wherein the vitiligo is segmental vitiligo. 284. The method of embodiment 249 or 250, wherein the patient has a vitiligo disease duration of at last 20 years.
285. The method of embodiment 249 or 250, wherein the patient has a disease duration at baseline of at least 10 years.
286. The method of embodiment 249 or 250, wherein the affected skin area is the face. 287. The method of embodiment 249 or 250, wherein the affected skin area is the head and neck.
288. The method of embodiment 249 or 250, wherein the affected skin area is selected from lower extremities, trunk, hands, upper extremities, and feet.
289. The method of embodiment 249 or 250, wherein the affected skin area is selected from non-acral lower extremities and non-acral upper extremities.
290. The method of embodiment 249 or 250, wherein the patient has at least 0.5% facial body surface area affected by vitiligo.
291. The method of embodiment 249 or 250, wherein the patient has at least 3% non-facial body surface area affected by vitiligo.
292. The method of embodiment 249 or 250, wherein the patient has at least 0.5% facial body surface area affected by vitiligo and at least 3% non-facial body surface area affected by vitiligo.
293. The method of embodiment 249 or 250, wherein the patient has been clinically diagnosed with vitiligo.
294. The method of embodiment 249 or 250, wherein the patient does not administer any other agents for the treatment of vitiligo.
295. The method of embodiment 249 or 250, wherein the patient is 18 years old to 75 years old.

The following are examples of the practice of the invention. They are not to be construed as limiting the scope of the invention in any way.

EXAMPLES

Example 1—Phase II Study Regarding Treatment of Vitiligo with Ruxolitinib

INCB 18424-211 was a Phase II, randomized, double-blind, vehicle-controlled, 3-parts study in adults with vitiligo who had depigmented areas including at least 0.5% BSA on the face and at least 3% BSA on nonfacial areas. A total of 157 participants were equally randomized to receive ruxolitinib cream 1.5% BID, 1.5% QD, 0.5% QD, 0.15% QD, or vehicle BID for 24 weeks. The ruxolitinib in the cream formulation was present as ruxolitinib phosphate with the percentages as % w/w on a free base basis. The 0.5% and 1.5% cream formulations were oil-in-water cream formulations as described in Tables 3 and 5 of U.S. Patent Publ. No. 2015/0250790, which is incorporated herein by reference in its entirety.

The mean (SD) age was 48.3 (12.9) years, 46.5% of patients were men, and 84.1% were white. The distribution of baseline disease characteristics was similar across treatment groups. See Table 1 for patient demographics and baseline disease characteristics. Most patients (93.0%) had nonsegmental vitiligo and skin types II-III (63.7%). Median (range) disease duration was 14.0 (0.3-67.9) years. The mean (SD) percentages of T-BSA and F-BSA involvement at baseline were 22.1% (18.4%) and 1.48% (0.86%), respectively, and baseline mean (SD) T-VASI and F-VASI scores were 18.0 (15.5) and 1.26 (0.82), respectively. Discontinuation rates were low through Week 52. By Week 24, 18 patients (11.5%) had discontinued study treatment. Primary reasons were withdrawal by patient (6.4%), AEs (1.9%), patient lost to follow-up (1.3%), protocol deviation (1.3%), and noncompliance with study drug (0.6%).

In the second part of the study, all participants initially randomized to vehicle BID and participants initially randomized to 0.15% QD who did not achieve≥25% improvement from baseline in F-VASI were rerandomized to 1 of the 3 higher dosing groups for an additional 28 weeks. All other participants maintained the same treatment until Week 52. After Week 52, participants could receive open-label 1.5% BID for an additional 52 weeks. The primary endpoint was the proportion of participants who achieved a ≥50% improvement from baseline in F-VASI50 at Week 24. The secondary endpoints include achieving scores of clear or almost clear (F-PhGVA is 0 or 1) in the Physician's Global Vitiligo Assessment (F-PhGVA) at Week 24; percentage of participants achieve T-VASI50 at Week 52; and safety and tolerability assessed by monitoring the frequency, duration, and severity of adverse events (AEs) at least 30 days after the last dose, up to 120 weeks. Subjects who were receiving any kind of phototherapy, including tanning beds, were excluded from the study. Also excluded are subjects with other dermatologic disease besides vitiligo whose presence or treatments could complicate the assessment of repigmentation; subjects who have used skin bleaching treatments for past treatment of vitiligo or other pigmented areas; subjects who have received any of the following treatments within the minimum specified timeframes such as the use of any biologic, investigational, or experimental therapy or procedure for vitiligo within 12 weeks or 5 half-lives (whichever is longer) of screening, the use of laser or light-based vitiligo treatments, including tanning beds, within 8 weeks of screening, and the use of immunomodulating oral or systemic medications (eg, corticosteroids, methotrexate, cyclosporine) or topical treatments that may affect vitiligo (eg, corticosteroids, tacrolimus/pimecrolimus, retinoids) within 4 weeks of screening; subjects who use any prior and concomitant therapy not listed above that may interfere with the objective of the study as per discretion of the investigator, including drugs that cause photosensitivity or skin pigmentation (eg, antibiotics such as tetracyclines, antifungals) within 8 weeks of screening; subjects with a clinically significant abnormal thyroid-stimulating hormone or free T4 at screening; subjects with protocol-defined cytopenias at screening; subjects with severely impaired liver function; subjects with impaired renal function; subjects taking potent systemic cytochrome P450 3A4 inhibitors or fluconazole within 2 weeks or 5 half-lives, whichever is longer, before the baseline visit, and subjects who have previously received JAK inhibitor therapy, systemic or topical. In this study, the area of the face analyzed for F-VASI included the area on the forehead to the hairline, on the cheek to the jawline vertically to the jawline and laterally from the corner of the mouth to the tragus. The area of the face analyzed did not include surface area of the lips, scalp, eyelids, ears, or neck but did include the nose.

TABLE 1

Patient Demographics and Baseline Disease Characteristics

| | Vehicle BID (n = 32) | Ruxolitinib Cream | | | | |
|---|---|---|---|---|---|---|
| | | 0.15% QD (n = 31) | 0.5% QD (n = 31) | 1.5% QD (n = 30) | 1.5% BID (n = 33) | Total (n = 157) |
| Age, mean (SD), y | 46.3 (13.1) | 45.1 (11.5) | 53.8 (14.3) | 46.7 (11.7) | 49.5 (12.3) | 48.3 (12.9) |
| Age group, n (%), y | | | | | | |
| ≤50 | 20 (62.5) | 21 (67.7) | 10 (32.3) | 18 (60.0) | 17 (51.5) | 86 (54.8) |
| >50 | 12 (37.5) | 10 (32.3) | 21 (67.7) | 12 (40.0) | 16 (48.5) | 71 (45.2) |
| Sex, n (%) | | | | | | |
| Male | 12 (37.5) | 13 (41.9) | 19 (61.3) | 11 (36.7) | 18 (54.5) | 73 (46.5) |
| Female | 20 (62.5) | 18 (58.1) | 12 (38.7) | 19 (63.3) | 15 (45.5) | 84 (53.5) |
| Race, n (%) | | | | | | |
| Caucasian | 26 (81.3) | 29 (93.5) | 25 (80.6) | 23 (76.7) | 29 (87.9) | 132 (84.1) |
| Non-Caucasian | 6 (18.8) | 2 (6.5) | 6 (19.4) | 7 (23.3) | 4 (12.1) | 25 (15.9) |
| Skin type, n (%) | | | | | | |
| I-II | 8 (25.0) | 12 (38.7) | 13 (41.9) | 10 (33.3) | 13 (39.4) | 56 (35.7) |
| III-VI | 24 (75.0) | 19 (61.3) | 18 (58.1) | 20 (66.7) | 20 (60.6) | 101 (64.3) |
| F-BSA[a], mean (SD), % | 1.44 (0.84) | 1.35 (0.86) | 1.40 (0.76) | 1.67 (0.95) | 1.55 (0.89) | 1.48 (0.86) |
| ≤1.5, n (%) | 20 (62.5) | 21 (67.7) | 20 (64.5) | 17 (56.7) | 19 (57.6) | 97 (61.8) |
| >1.5, n (%) | 12 (37.5) | 10 (32.3) | 11 (35.5) | 13 (43.3) | 14 (42.4) | 60 (38.2) |
| T-BSA, mean (SD), % | 23.5 (21.0) | 17.6 (10.9) | 23.0 (21.5) | 24.8 (20.1) | 21.5 (16.8) | 22.1 (18.4) |
| ≤20, n (%) | 19 (59.4) | 22 (71.0) | 20 (64.5) | 19 (63.3) | 20 (60.6) | 100 (63.7) |
| >20, n (%) | 13 (40.6) | 9 (29.0) | 11 (35.5) | 11 (36.7) | 13 (39.4) | 57 (36.3) |
| Baseline F-VASI, mean (SD) | 1.21 (0.85) | 1.19 (0.75) | 1.22 (0.71) | 1.45 (0.98) | 1.26 (0.81) | 1.26 (0.82) |
| Disease duration[b], median (range), y | 15.4 (1.5-37.6) | 13.7 (0.3-67.9) | 10.8 (1.7-59.0) | 14.7 (0.3-56.0) | 13.5 (0.8-47.8) | 14.0 (0.3-67.9) |
| <10, n (%) | 10 (31.3) | 11 (35.5) | 14 (45.2) | 7 (23.3) | 11 (33.3) | 53 (33.8) |
| 10-20, n (%) | 10 (31.3) | 8 (25.8) | 7 (22.6) | 13 (43.3) | 11 (33.3) | 49 (31.2) |
| >20, n (%) | 12 (37.5) | 12 (38.7) | 10 (32.3) | 10 (33.3) | 10 (30.3) | 54 (34.4) |
| Disease status[c], n (%) | | | | | | |
| Stable | 11 (34.4) | 11 (35.5) | 19 (61.3) | 14 (46.7) | 13 (39.4) | 68 (43.3) |
| Progressive | 21 (65.6) | 20 (64.5) | 12 (38.7) | 16 (53.3) | 20 (60.6) | 89 (56.7) |
| Previous therapy, n (%) | | | | | | |
| TCS | 16 (50.0) | 16 (51.6) | 12 (38.7) | 14 (46.7) | 14 (42.4) | 72 (45.9) |
| TCI | 18 (56.3) | 14 (45.2) | 13 (41.9) | 11 (36.7) | 14 (42.4) | 70 (44.6) |
| Phototherapy[d] | 14 (43.8) | 5 (16.1) | 13 (41.9) | 11 (36.7) | 12 (36.4) | 55 (35.0) |

BID, twice daily; F-BSA, facial body surface area; F-VASI, facial Vitiligo Area Scoring Index; QD, once daily; T-BSA, total body surface area; TCI, topical calcineurin inhibitors; TCS, topical corticosteroids; T-VASI, total Vitiligo Area Scoring Index.
[a]Percentage of T-BSA.
[b]Data missing from 1 patient in the 1.5% BID group.
[c]Determination of disease stability was based on investigator judgment.
[d]Phototherapy includes narrowband ultraviolet B phototherapy, psoralen ultraviolet A photochemotherapy, and excimer laser.

Week 24

All ruxolitinib treatment arms demonstrated clinically meaningful efficacy and superiority over vehicle. The proportion of participants who achieved an F-VASI50 at Week 24 was statistically significantly greater for ruxolitinib cream versus vehicle with response rates of 32.3%, 25.8%, 50.0%, 45.5%, and 3.2% for ruxolitinib cream 0.15% QD, 0.5% QD, 1.5% QD, 1.5% BID, and vehicle, respectively.

All ruxolitinib treatment arms were generally safe and well-tolerated with no significant TEAEs or application site events and no clinically relevant hematological changes. Discontinuations from treatment through 24 weeks was low (11.5% overall). Key endpoints from the Week 24 analysis are summarized in Table 2.

responders who had stable vs progressive disease. This indicates that ruxolitinib cream was effective for the treatment of vitiligo a in patients with longstanding and extensive disease with high inflammatory burden (as indicated by the extent of skin surface depigmentation). A larger proportion of patients who had received previous phototherapy (n=12 [66.7%]) as opposed to corticosteroids (n=14 [50.0%]) or calcineurin inhibitors (n=14 [42.9%]) were F-VASI50 responders.

After completion of the Week 24 assessments, subjects randomized to vehicle were randomized to 1 of the 3 higher active treatment groups in a 1:1:1 ratio while maintaining the blind. Subjects in the ruxolitinib (INCB018424) 0.15% QD dose group who did not achieve a ≥25% improvement

TABLE 2

Summary of INCB 18424-211 Efficacy Endpoints at Week 24

| Week 24 | % Achieving F-VASI50 | % Achieving F-VASI75 | % Change in F-VASI | % Change in F-BSA | % Achieving F-PhGVA 0/1 | % Achieving F-PaGVA Response |
|---|---|---|---|---|---|---|
| Face Only | | | | | | |
| Vehicle BID | 3.2 | 0 | 6 | 6.5 | 0 | 6.3 |
| 0.15% QD | 32.3 | 9.7 | −32.1 | −19.8 | 3.2 | 12.9 |
| 0.5% QD | 25.8 | 16.1 | −29.5 | −17.6 | 9.7 | 6.5 |
| 1.5% QD | 50.0 | 16.7 | −41.0 | −19.5 | 13.3 | 13.3 |
| 1.5% BID | 45.5 | 30.3 | −37.8 | −27.8 | 9.1 | 18.2 |

| Week 24 | % Achieving T-VASI25 | % Achieving T-VASI50 | % Change in T-VASI | % Change in T-BSA | % Achieving T-PhGVA 0/1 | % Achieving PaGICV 1/2 |
|---|---|---|---|---|---|---|
| Total Body | | | | | | |
| Vehicle BID | 0 | 0 | 1.26 | 3.4 | 0 | 7.4 |
| 0.15% QD | 32.3 | 16.1 | −21.9 | −14.0 | 0 | 23.1 |
| 0.5% QD | 29.0 | 6.5 | −16.0 | −10.8 | 3.3 | 20.0 |
| 1.5% QD | 46.7 | 23.3 | −28.1 | −17.2 | 0 | 30.8 |
| 1.5% BID | 36.4 | 12.1 | −22.9 | −13.6 | 3.2 | 29.0 |

F-PaGVA = Facial Patient's Global Vitiligo Assessment (response is 0 (no white patches) or 1 (mild) and at least a 1 point reduction from baseline); F-PhGVA = Facial Physician's Global Vitiligo Assessment (0 = Clear; 1 = Almost clear); PaGICV = Patient global impression of change for vitiligo (1 = very much improved; 2 = Much improved); T-PhGVA = Total Physician's Global Vitiligo Assessment (0 = Clear; 1 = Almost clear).

Results from the Week 24 analysis are presented in FIGS. 1 to 4.

Figure 62:
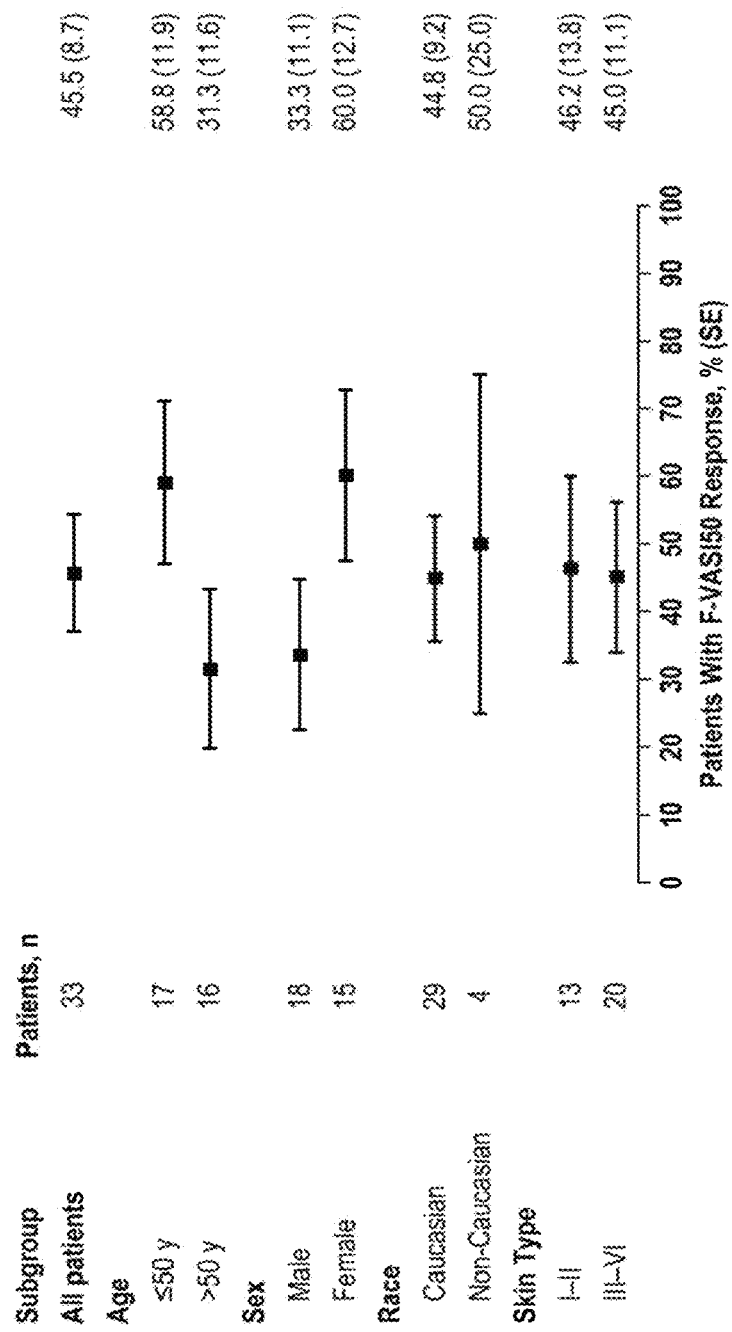
FIG. 62 is a chart showing F-VASI50 response to ruxolitinib cream 1.5% BID at week 24 by patient demographics and skin type.

FIG. 62 shows F-VASI50 response to ruxolitinib cream 1.5% BID at week 24 by patient demographics and skin type. Among 33 patients who received ruxolitinib cream 1.5% BID, a larger proportion of patients who were younger (≤50 years; n=17 [58.8%]) and female (n=15 [60.0%]) were F-VASI50 responders at 24 weeks. No substantial differences were seen for Caucasian vs non-Caucasian responders or those with skin types I-II vs III-VI.

Figure 63:
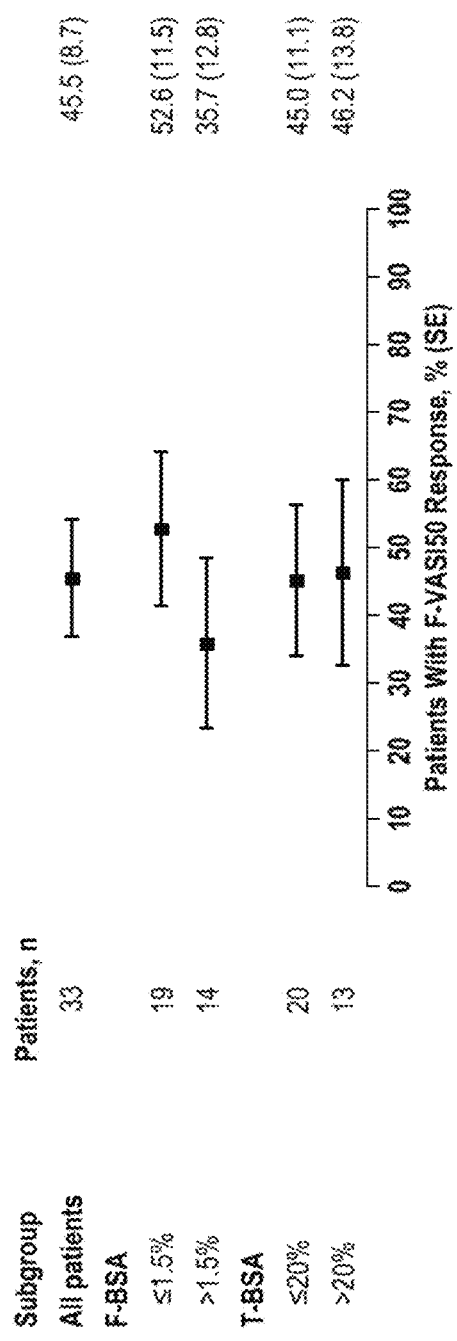
FIG. 63 is a chart showing F-VASI50 response to ruxolitinib cream 1.5% BID at Week 24 by baseline vitiligo lesion characteristics.

FIG. 63 shows F-VASI50 response to ruxolitinib cream 1.5% BID at Week 24 by baseline vitiligo lesion characteristics. Among the patients who received ruxolitinib cream 1.5% BID, a larger proportion of patients with ≤1.5% affected baseline F-BSA (n=19 [52.6%]) were F-VASI50 responders at Week 24. There were no substantial differences between responders with baseline T-BSA≤20% vs >20%, indicating that ruxolitinib cream was effective even in patients 10) with high disease burden.

Figure 64:
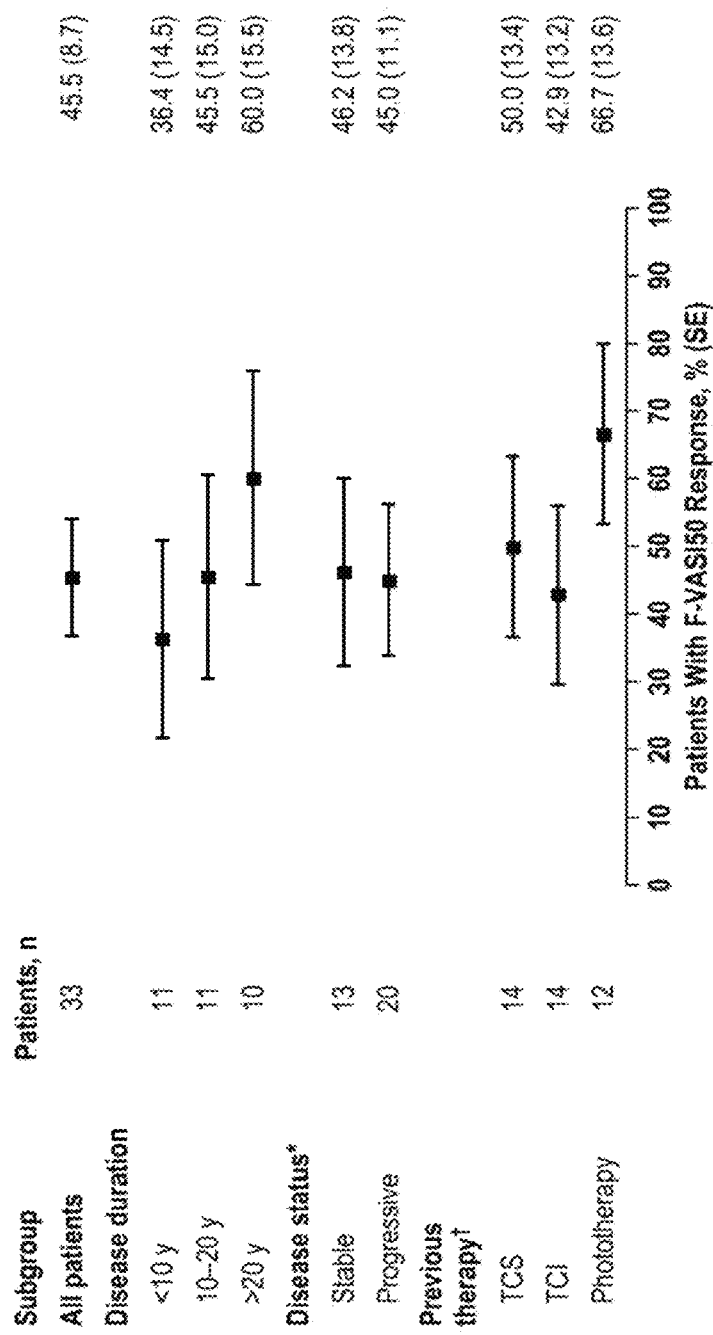
FIG. 64 is a chart showing F-VASI50 response to ruxolitinib cream 1.5% BID at Week 24 by disease characteristics and previous treatment.

FIG. 64 shows F-VASI50 response to ruxolitinib cream 1.5% BID at Week 24 by disease characteristics and previous treatment. Among patients treated with ruxolitinib cream 1.5% BID, a larger proportion of patients with longer disease duration (>20 years; n=10 [60.0%]) were F-VASI50 responders. No substantial differences were seen between from baseline on F-VASI (nonresponders of F-VASI25) were re-randomized to 1 of the 3 higher active treatment groups while maintaining the blind. Subjects randomized to ruxolitinib 0.15% QD who achieved a ≥25% improvement from baseline on F-VASI remained on the same dose until Week 52. Subjects randomized to ruxolitinib 1.5% BID, 1.5% QD, and 0.5% QD remained on the same dose until Week 52.

Figure 3:
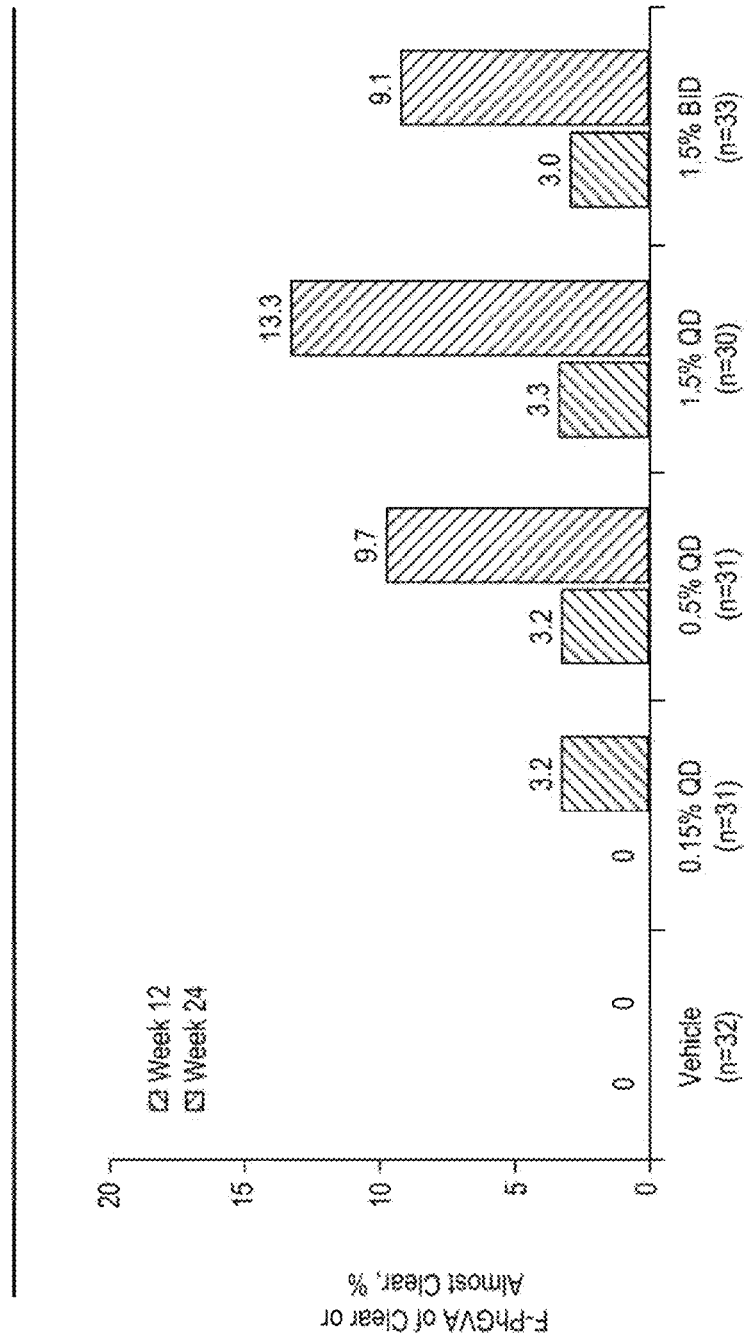
FIG. 3 is a graph of F-PhGVA of clear or almost clear (%) at Week 12 (first bar) and Week 24 (second bar) for vehicle, 0.15% QD ruxolitinib cream, 0.5% QD ruxolitinib cream, 1.5% QD ruxolitinib cream, and 1.5% BID ruxolitinib cream.
Figure 4:
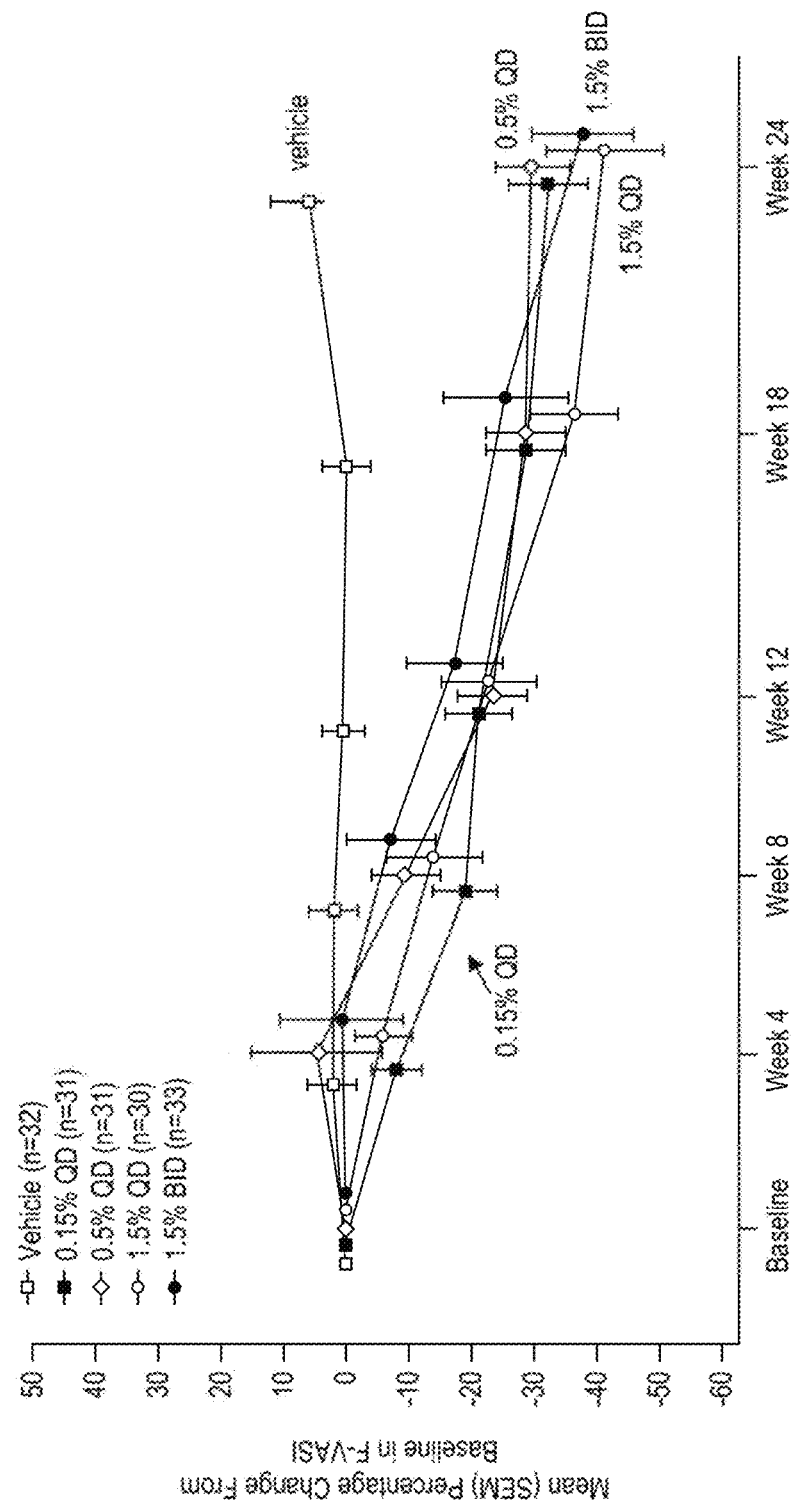
FIG. 4 is a graph of mean (SEM) percentage change from baseline in F-VASI at baseline, Week 4, Week 8, Week 12, Week 18, and Week 24 for vehicle, 0.15% QD ruxolitinib cream, 0.5% QD ruxolitinib cream, 1.5% QD ruxolitinib cream, and 1.5% BID ruxolitinib cream.
Figure 5:
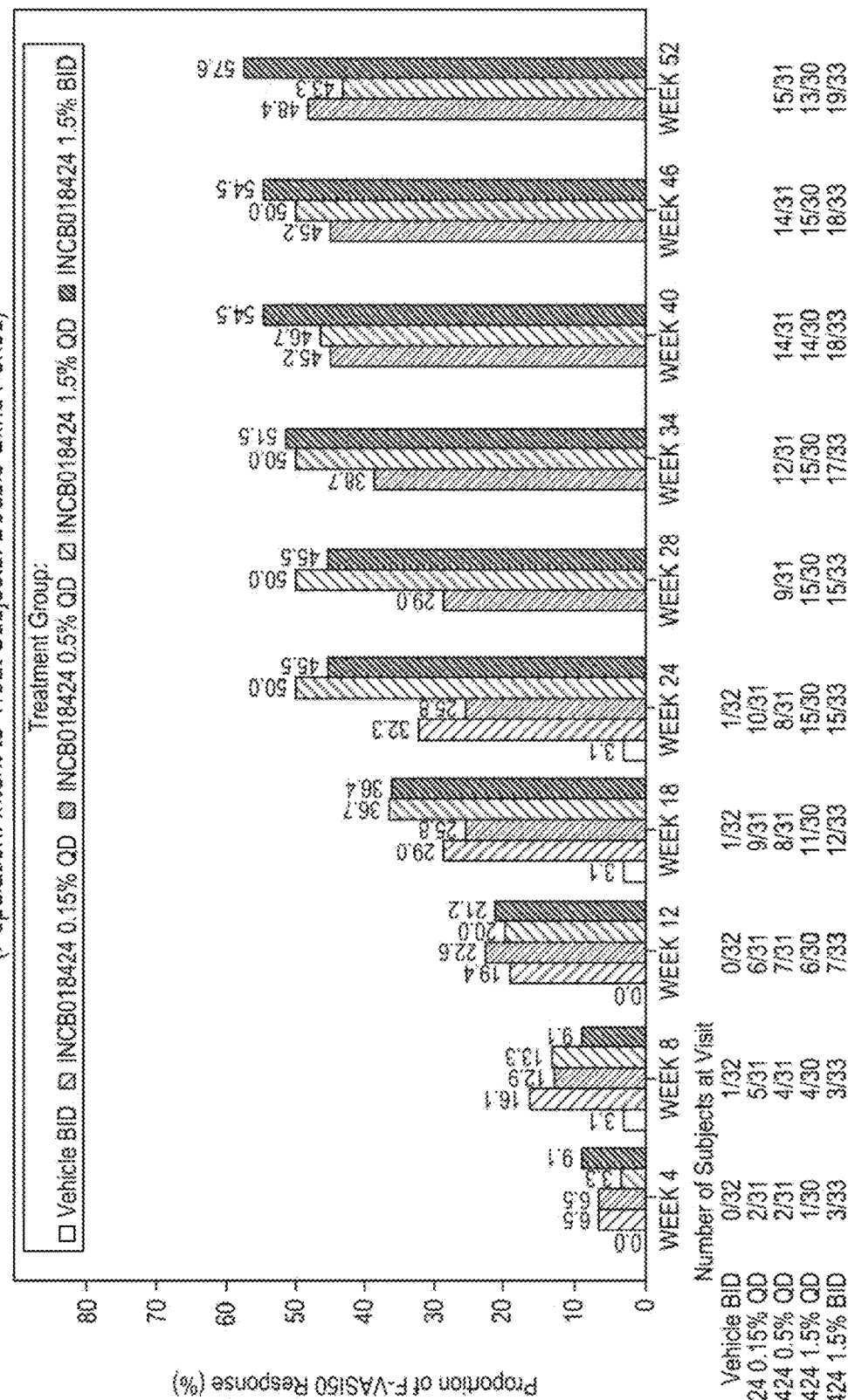
FIG. 5 is a graph depicting the proportion of subjects achieving F-VASI50 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 6:
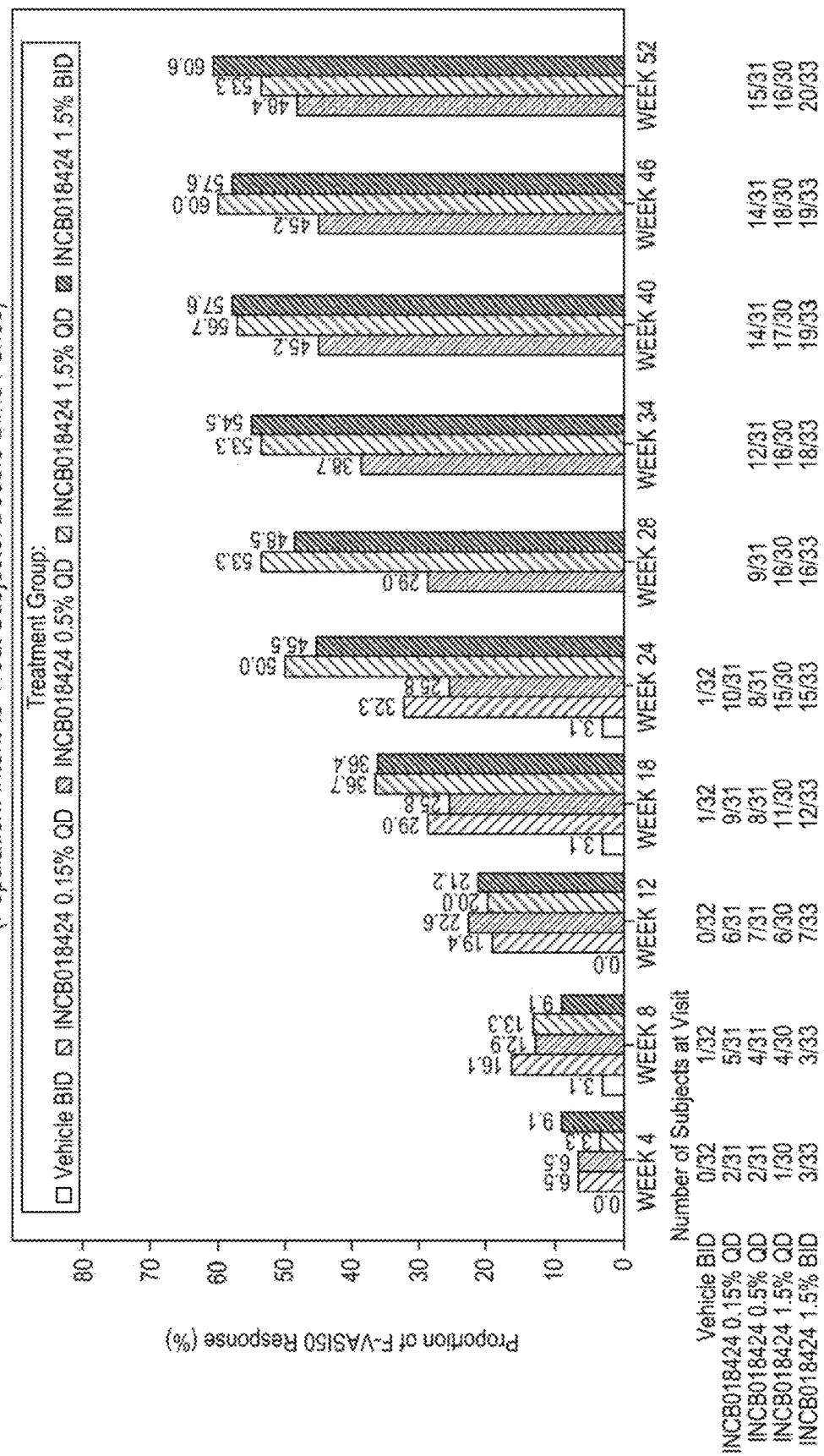
FIG. 6 is a graph depicting the proportion of subjects achieving F-VASI50 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period by a Last Observation Carried Forward (LOCF) imputation method.
Figure 7:
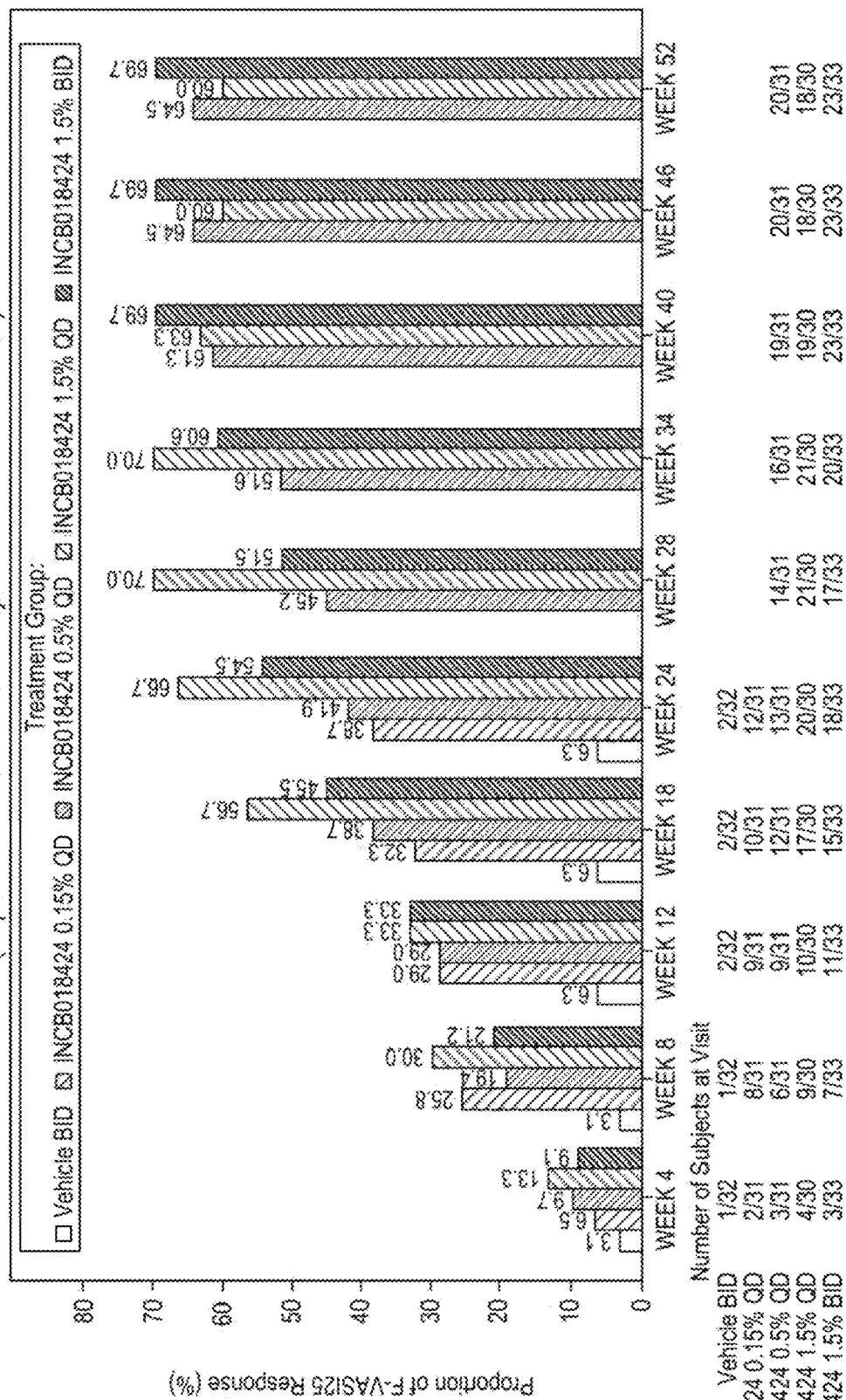
FIG. 7 is a graph depicting the proportion of subjects achieving F-VASI25 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 8:
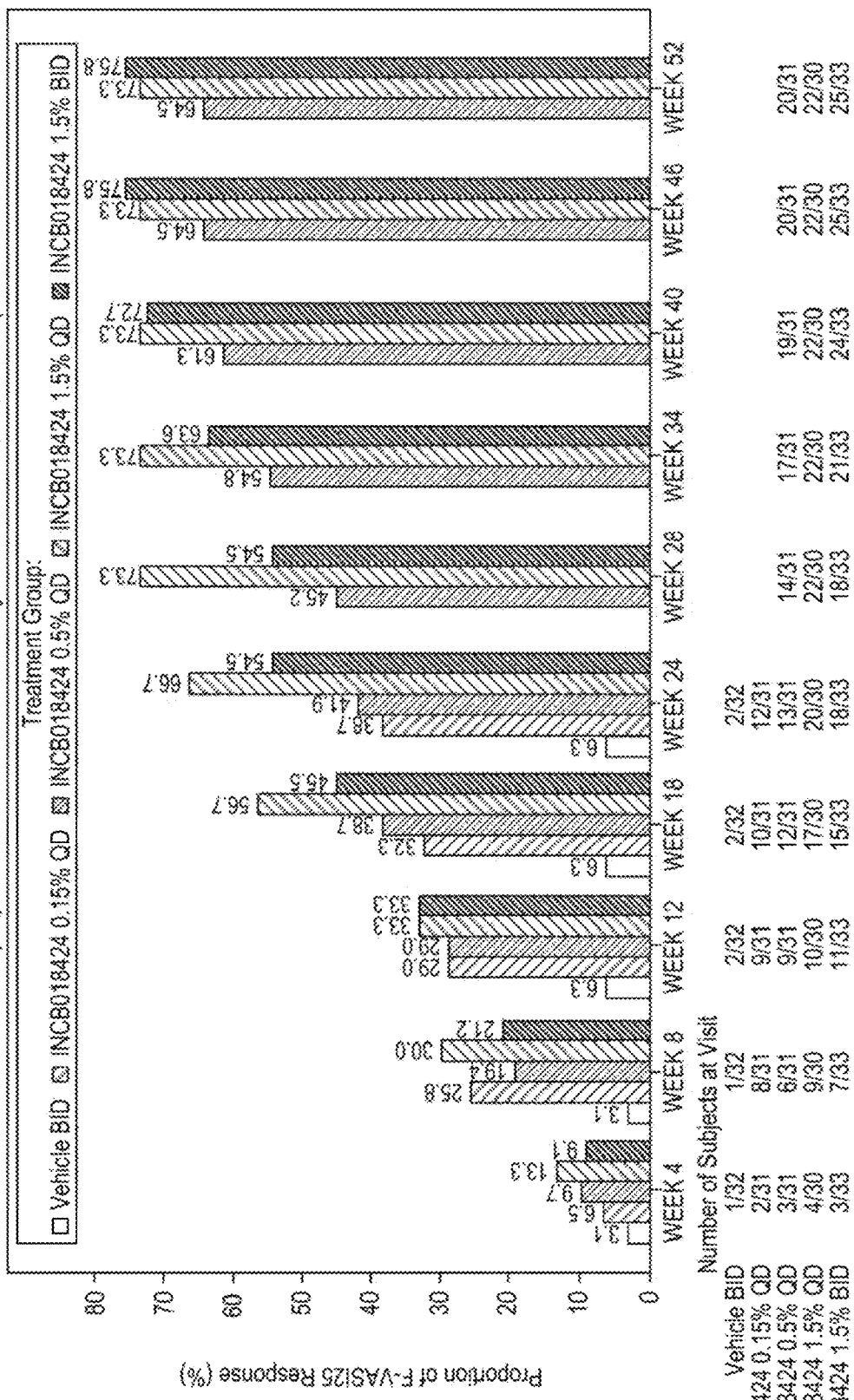
FIG. 8 is a graph depicting the proportion of subjects achieving F-VASI25 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order for the intent-to-treat subjects population in the double blind period by LOCF imputation method.

The primary endpoint, Week 24 F-VASI50, was achieved by significantly more patients treated with any dose of ruxolitinib cream (1.5% BID, 45.5% [P<0.001]; 1.5% QD, 50.0% [P<0.001]; 0.5% QD, 25.8% [P<0.05]; 0.15% QD, 32.3% [P<0.01]) than vehicle (3.1%; FIG. 5). The additional key secondary endpoint of achieving scores of clear or almost clear in the F-PhGVA at Week 24 was attained only by patients treated with ruxolitinib cream (3.2%-13.3% across doses; FIG. 3).

Subgroup analysis investigated response by patient demographics and baseline characteristics; results were generally similar across treatment groups at Week 24. Among patients who received ruxolitinib cream 1.5% BID (n=33; F-VASI50 responders, 45.5%), a larger proportion of patients in the following subgroups were F-VASI50 responders: patients≤50 years old (58.8%); female patients (60.0%); patients with skin type I-III (50.0%), ≤1.5% affected baseline facial BSA (52.6%), baseline F-VASI scores of 0.75 to <1.5 (75.0%), and disease duration >20 years (60.0%); and previous recipients of topical corticosteroids (50.0%). There were no substantial differences between responders who were white (44.8%) vs nonwhite (50.0%), who had stable (46.2%) vs progressive disease (45.0%), or those with total BSA≤20% (45.0%) vs >20% (46.2%). Ruxolitinib cream was effective for the treatment of vitiligo across demographics and clinical characteristics, including in patients with longstanding and extensive disease.

Week 52

Results from the Week 52 analysis are presented in FIGS. 5 to 22 and in Table 3. Sub-analysis was also conducted on T-VASI scores for head and neck, hands, upper extremities, trunk, lower extremities, and feet. Results from this sub-analysis are presented in FIGS. 23 to 53. Additional results are shown in FIGS. 54 to 61.

TABLE 3

|  | VEHICLE BID (N = 32) | RUXOLITINIB CREAM | | | |
|---|---|---|---|---|---|
|  |  | 0.15% QD (N = 31) | 0.5% QD (N = 31) | 1.5% QD (N = 30) | 1.5% BID (N = 33) |
| WEEK 24 F-VASI, N (%) | | | | | |
| F-VASI25 | 2 (6.3) | 12 (38.7) | 31 (41.9) | 20 (66.7) | 18 (54.5) |
| F-VASI50 | 1 (3.1) | 10 (32.3) | 8 (25.8) | 15 (50.0) | 15 (45.5) |
| F-VASI75 | 0 | 3 (9.7) | 5 (16.1) | 5 (16.7) | 10 (30.3) |
| F-VASI90 | 0 | 1 (3.2) | 3 (9.7) | 4 (13.3) | 4 (12.1) |
| T-VASI, N (%) | | | | | |
| T-VASI25 | 0 | 8 (36.4) | 6 (30.0) | 10 (52.6) | 8 (40.0) |
| T-VASI50 | 0 | 4 (18.2) | 2 (10.0) | 6 (31.6) | 4 (20.0) |
| T-VASI75 | 0 | 2 (9.1) | 1 (5.0) | 0 | 1 (5.0) |
| T-VASI90 | 0 | 1 (4.5) | 0 | 0 | 0 |
| WEEK 52 F-VASI, N (%) | | | | | |
| F-VASI25 | NA | NA | 20 (64.5) | 18 (60.0) | 23 (69.7) |
| F-VASI50 | NA | NA | 15 (48.4) | 13 (43.3) | 19 (57.6) |
| F-VASI75 | NA | NA | 9 (29.0) | 9 (30.0) | 17 (51.5) |
| F-VASI90 | NA | NA | 6 (19.4) | 4 (13.3) | 11 (33.3) |
| T-VASI, N (%) | | | | | |
| T-VASI25 | NA | NA | 7 (35.0) | 9 (47.4) | 15 (75.0) |
| T-VASI50 | NA | NA | 5 (25.0) | 7 (36.8) | 9 (45.0) |
| T-VASI75 | NA | NA | 2 (10.0) | 2 (10.5) | 3 (15.0) |
| T-VASI90 | NA | NA | 0 | 0 | 1 (5.0) |

Figure 9:
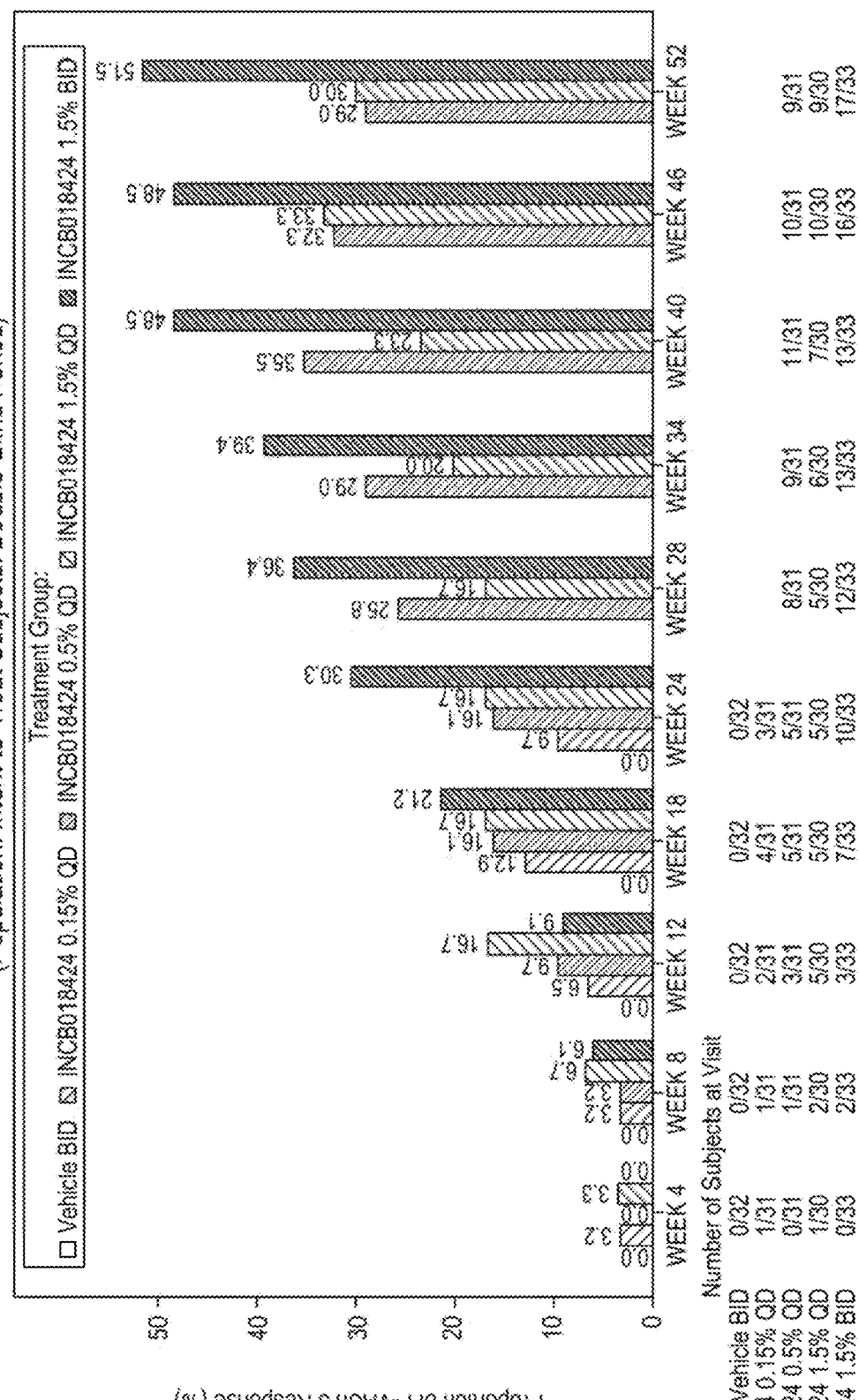
FIG. 9 is a graph depicting the proportion of subjects achieving F-VASI75 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 10:
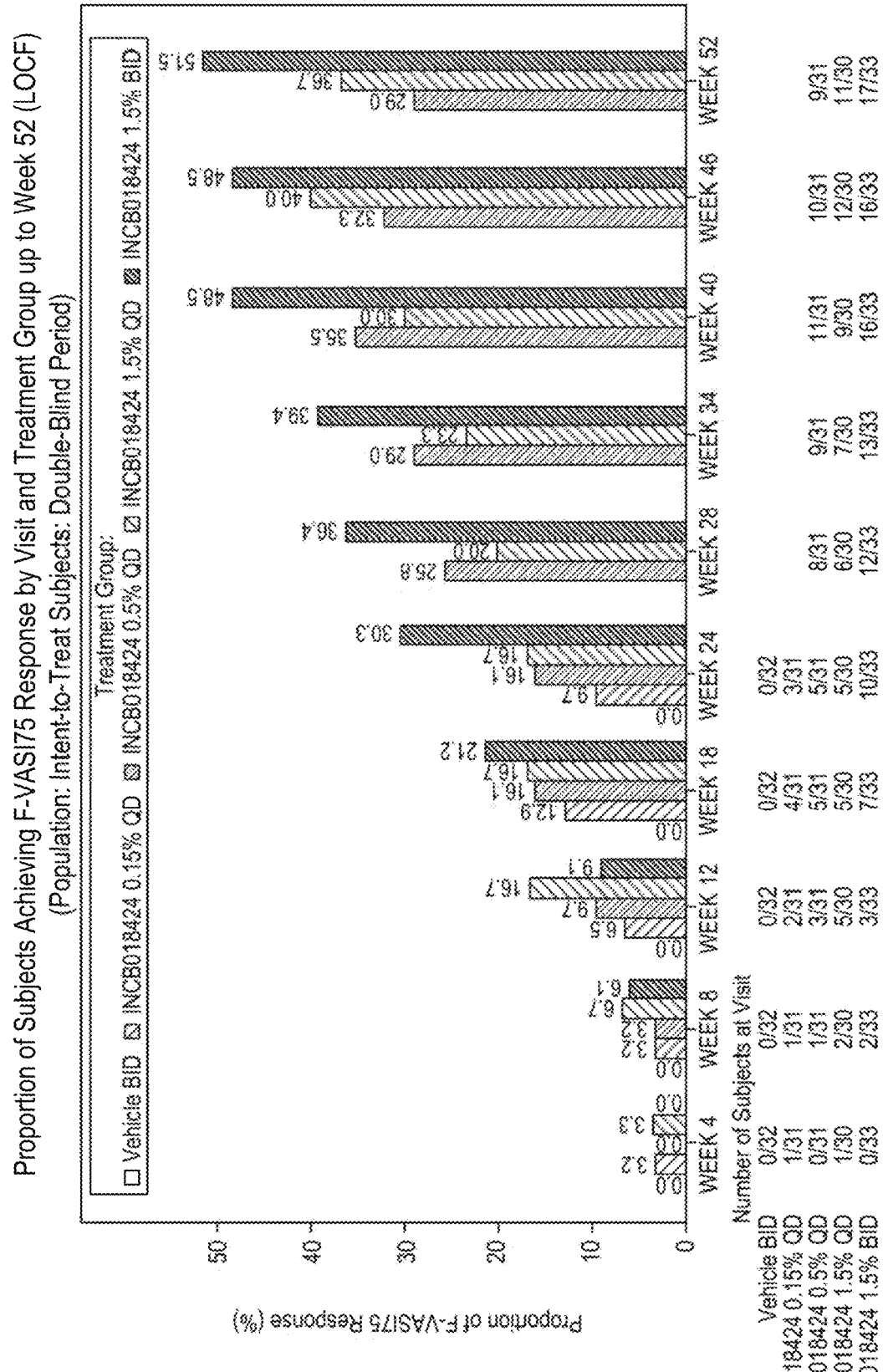
FIG. 10 is a graph depicting the proportion of subjects achieving F-VASI75 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period by a LOCF imputation method.
Figure 11:
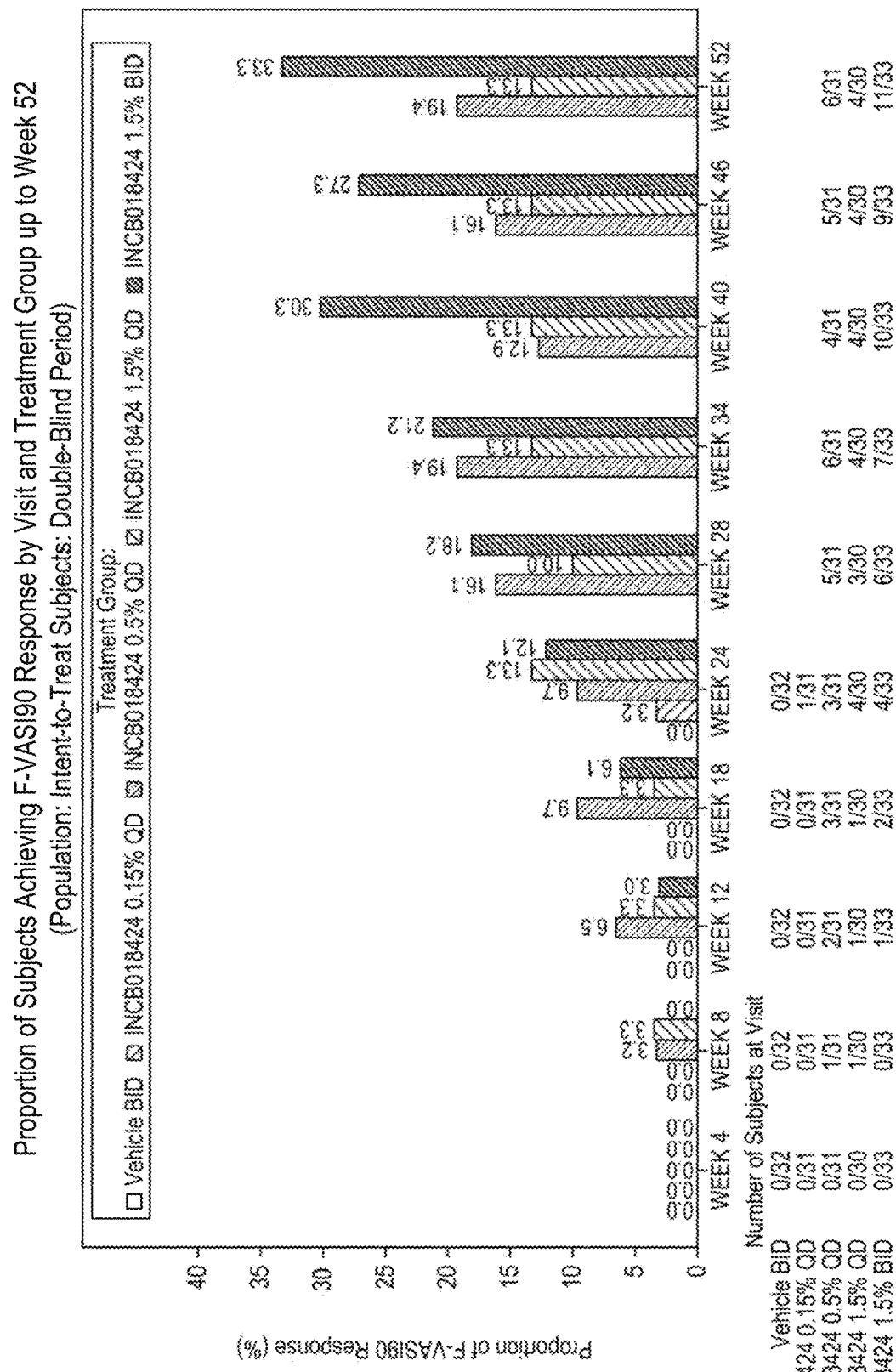
FIG. 11 is a graph depicting the proportion of subjects achieving F-VASI90 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 12:
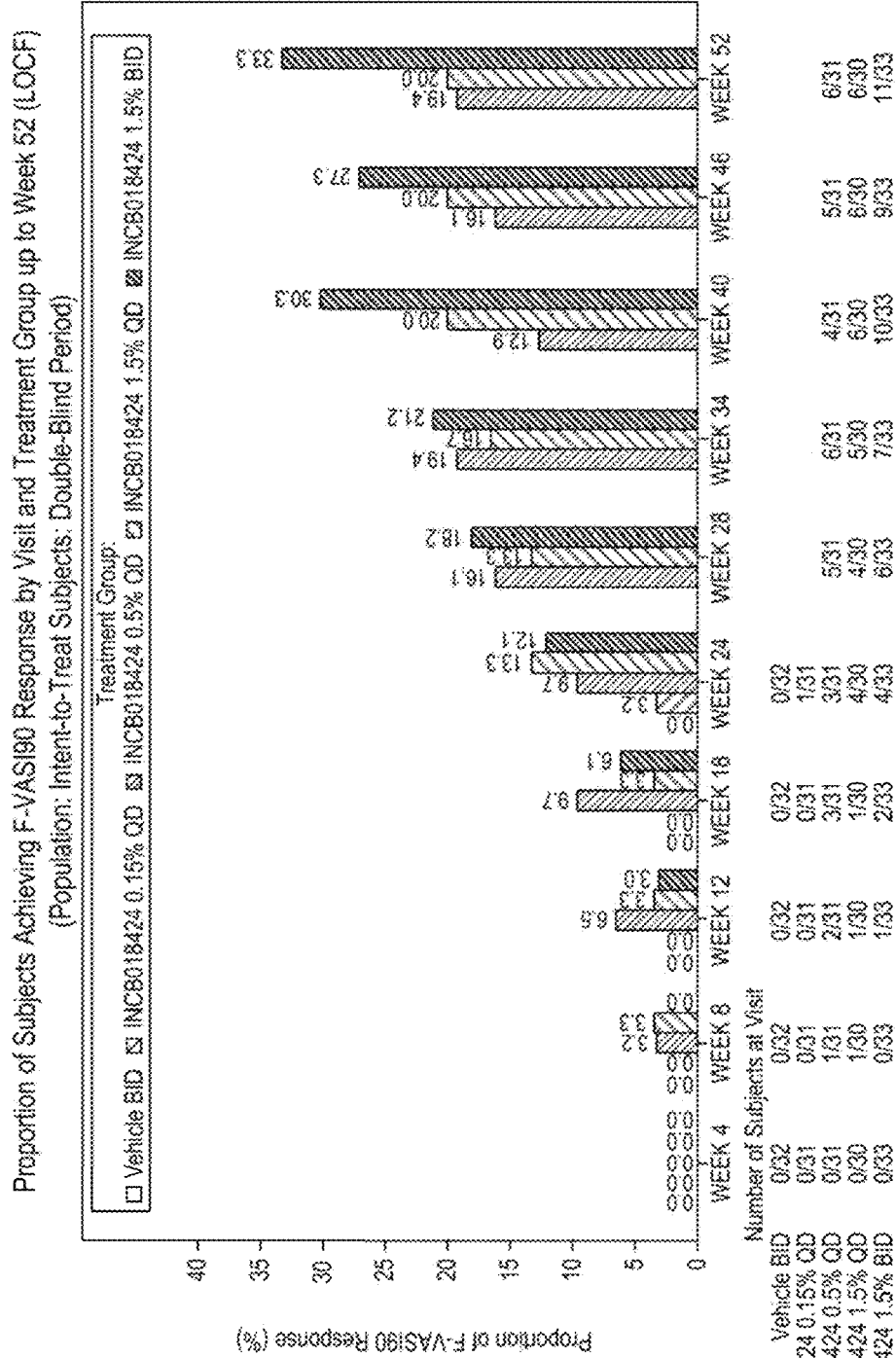
FIG. 12 is a graph depicting the proportion of subjects achieving F-VASI90 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period by a LOCF imputation method.
Figure 13:
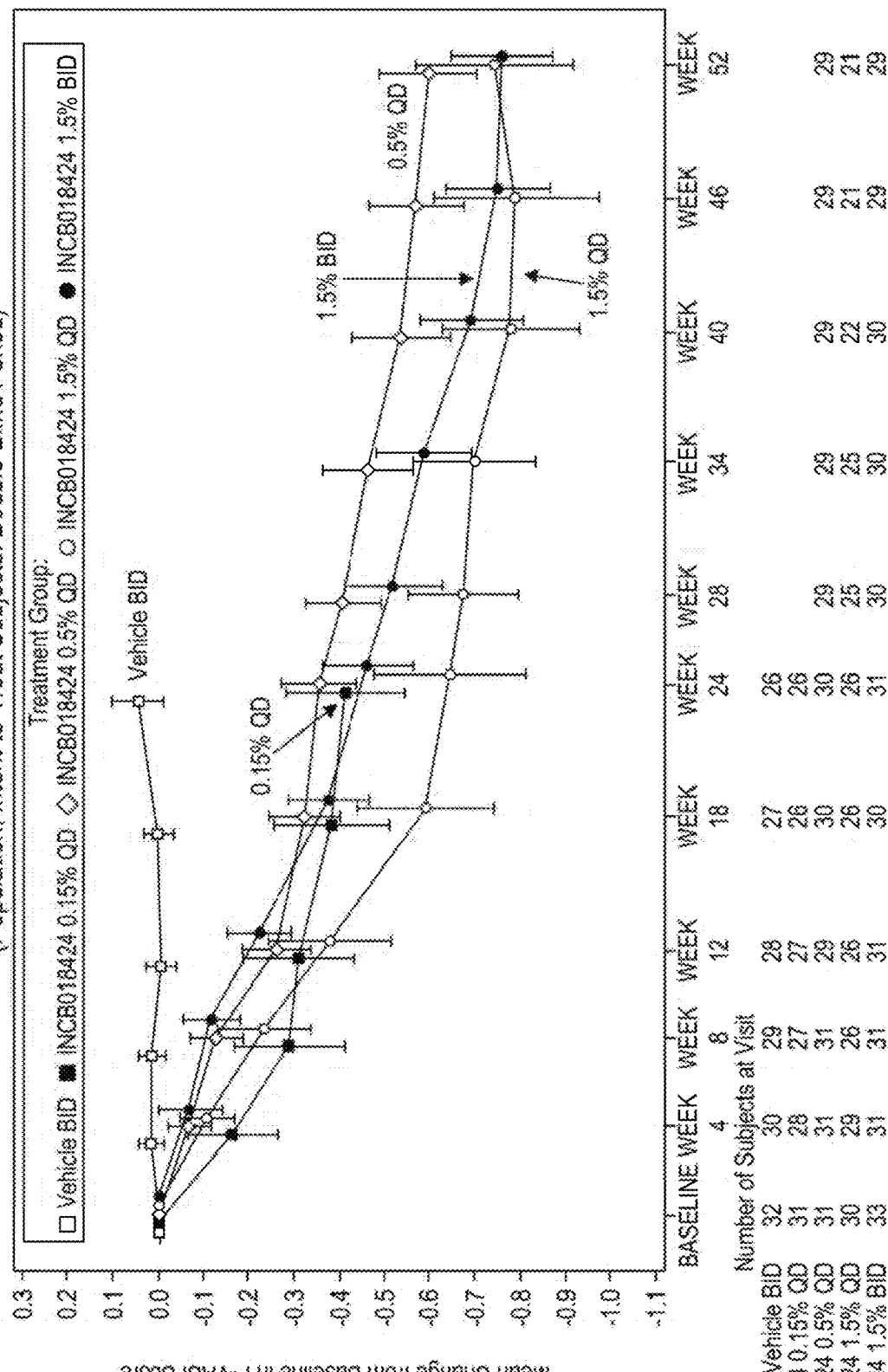
FIG. 13 is a graph depicting mean change from baseline in F-VASI score by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 14:
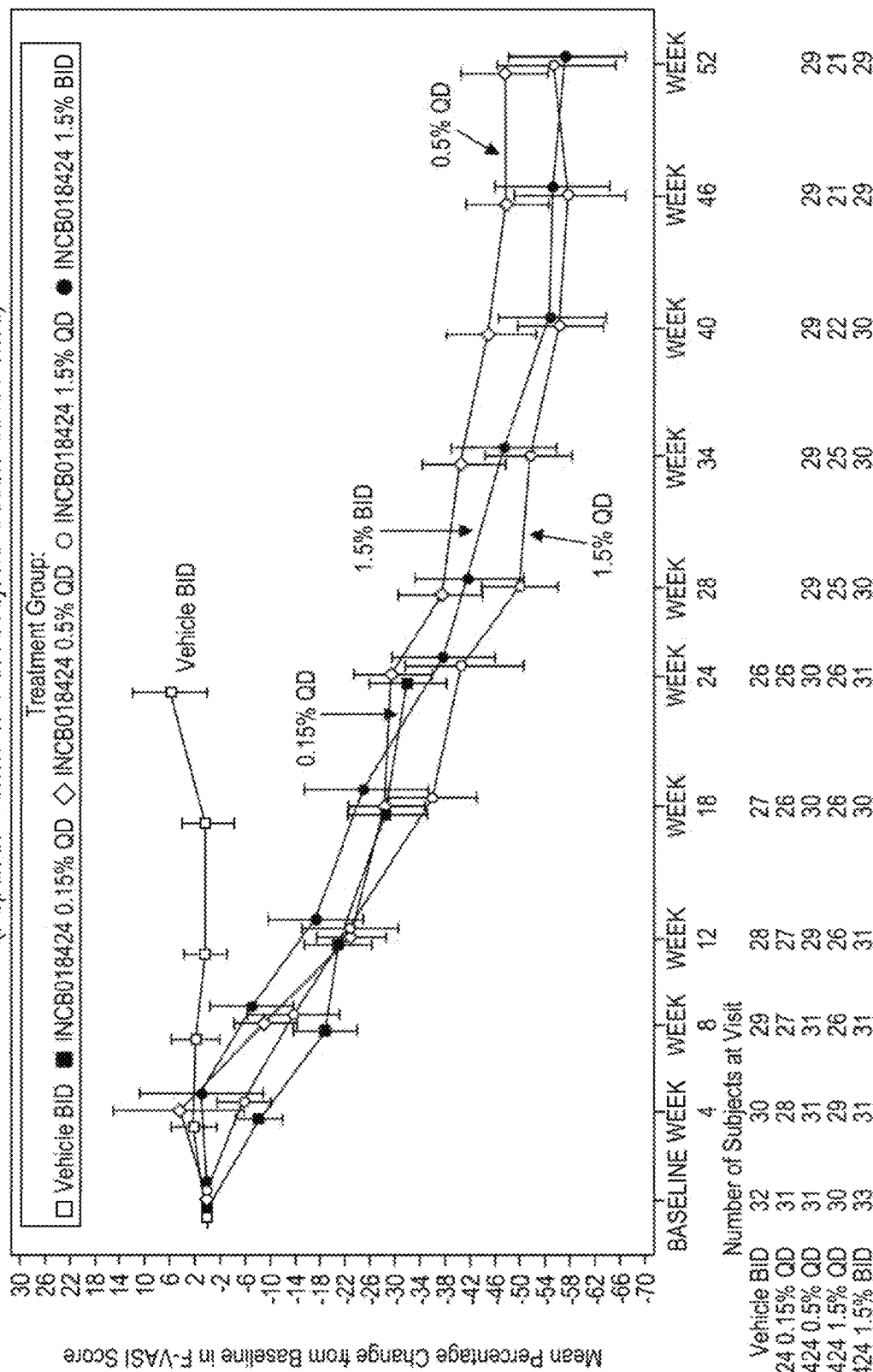
FIG. 14 is a graph depicting mean percentage change from baseline in F-VASI score by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 15:
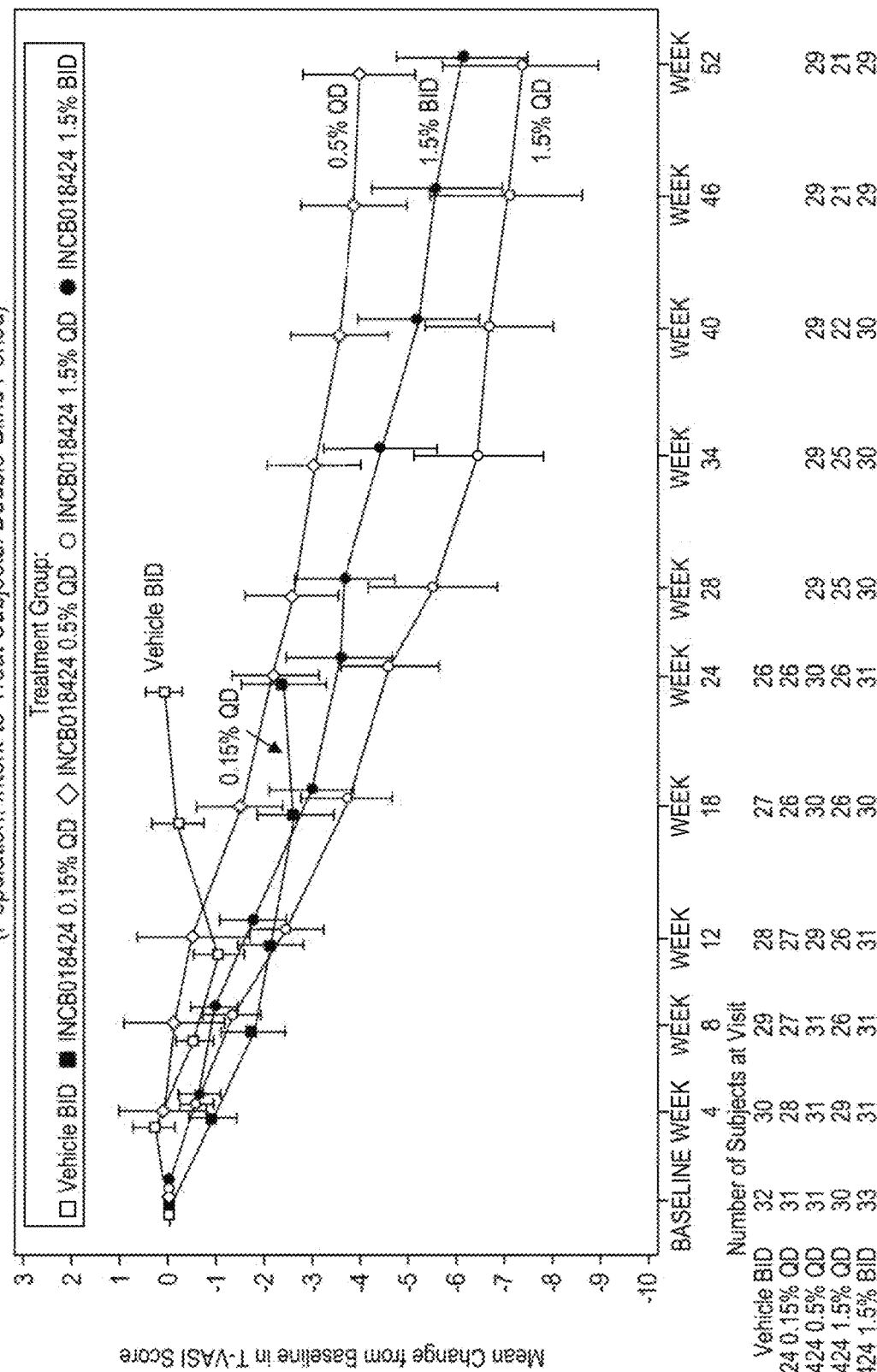
FIG. 15 is a graph depicting mean change from baseline in T-VASI score by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 16:
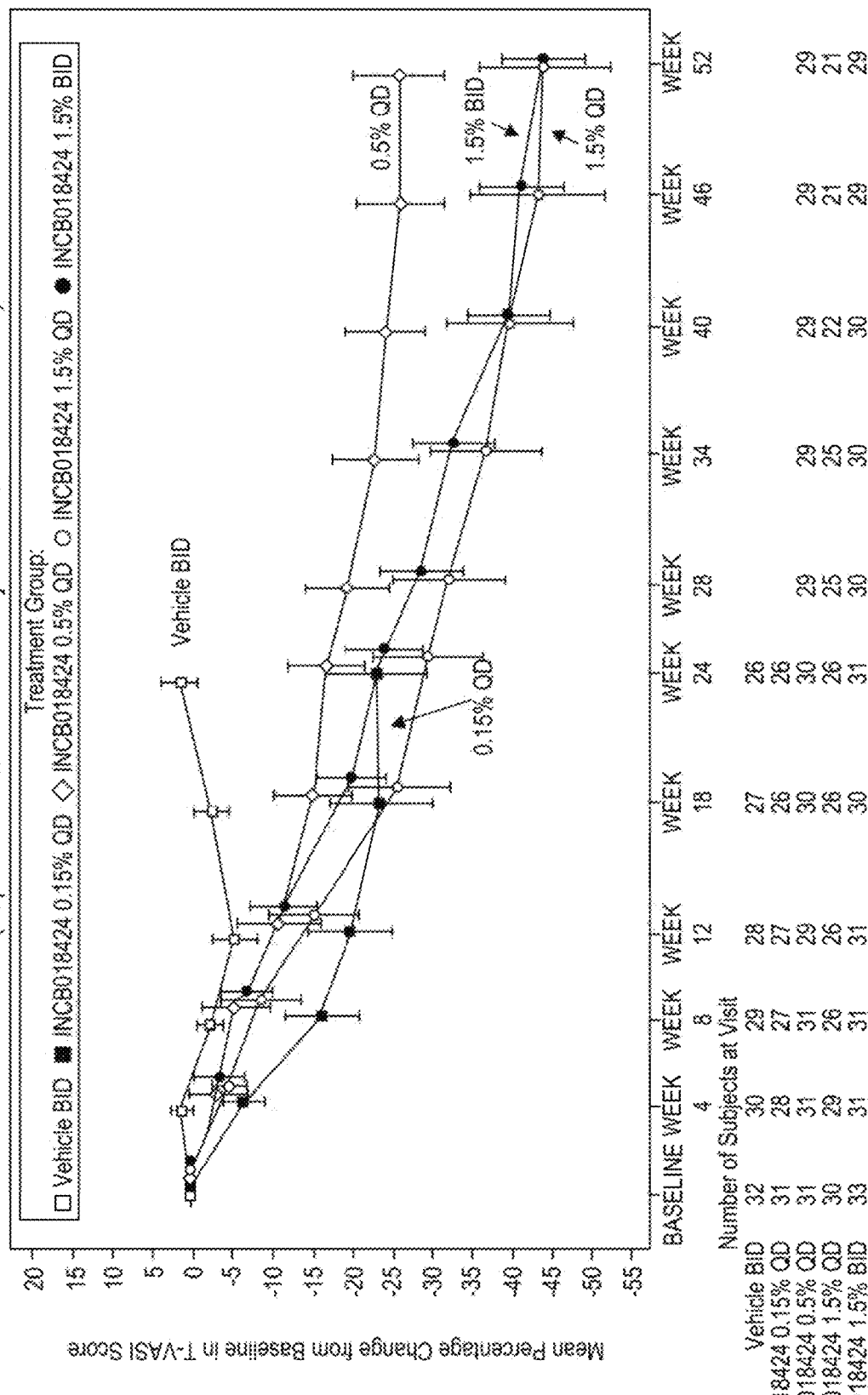
FIG. 16 is a graph depicting mean percentage change from baseline in T-VASI score by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 17:
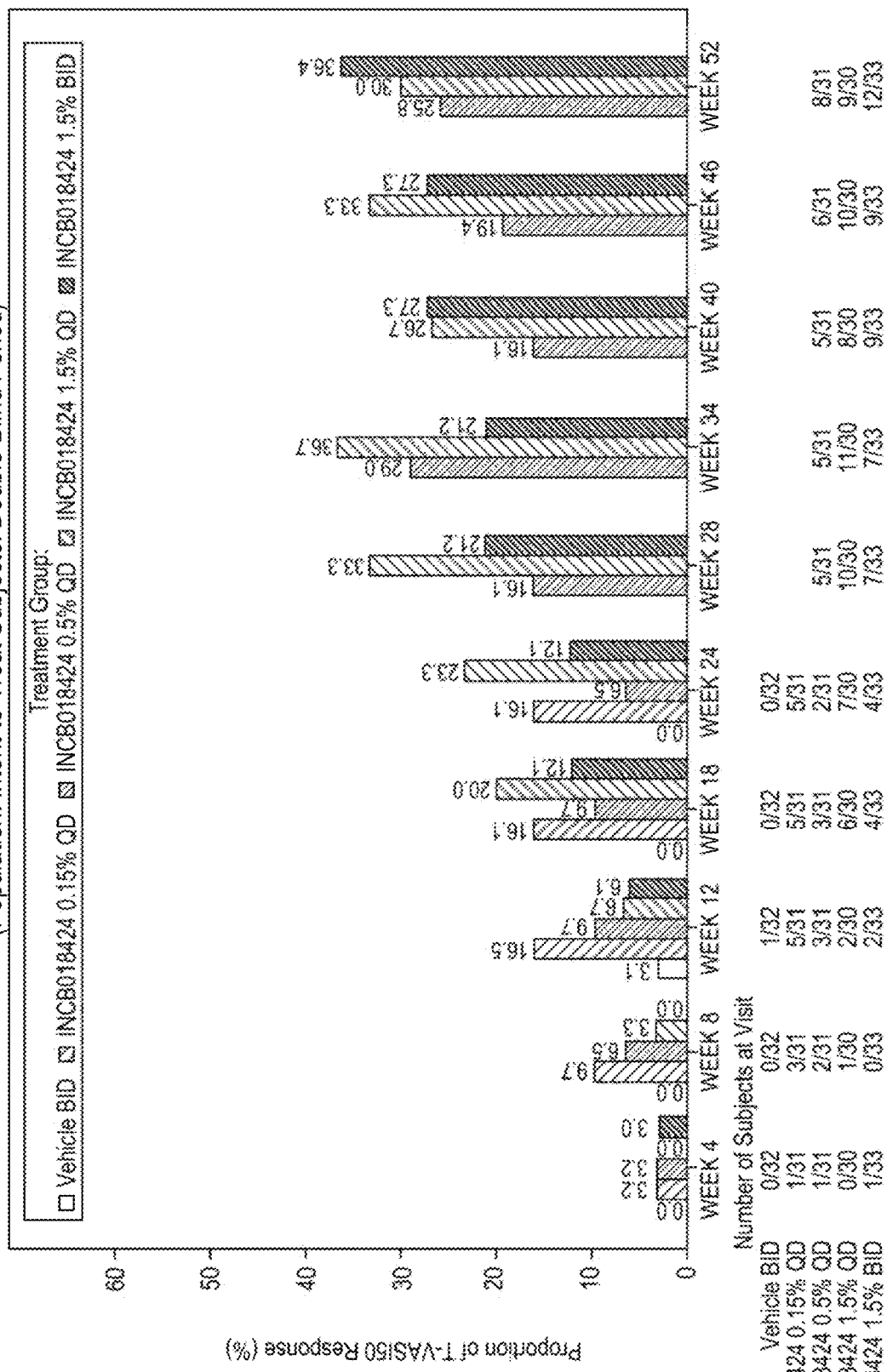
FIG. 17 is a graph depicting the proportion of subjects achieving T-VASI50 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 18:
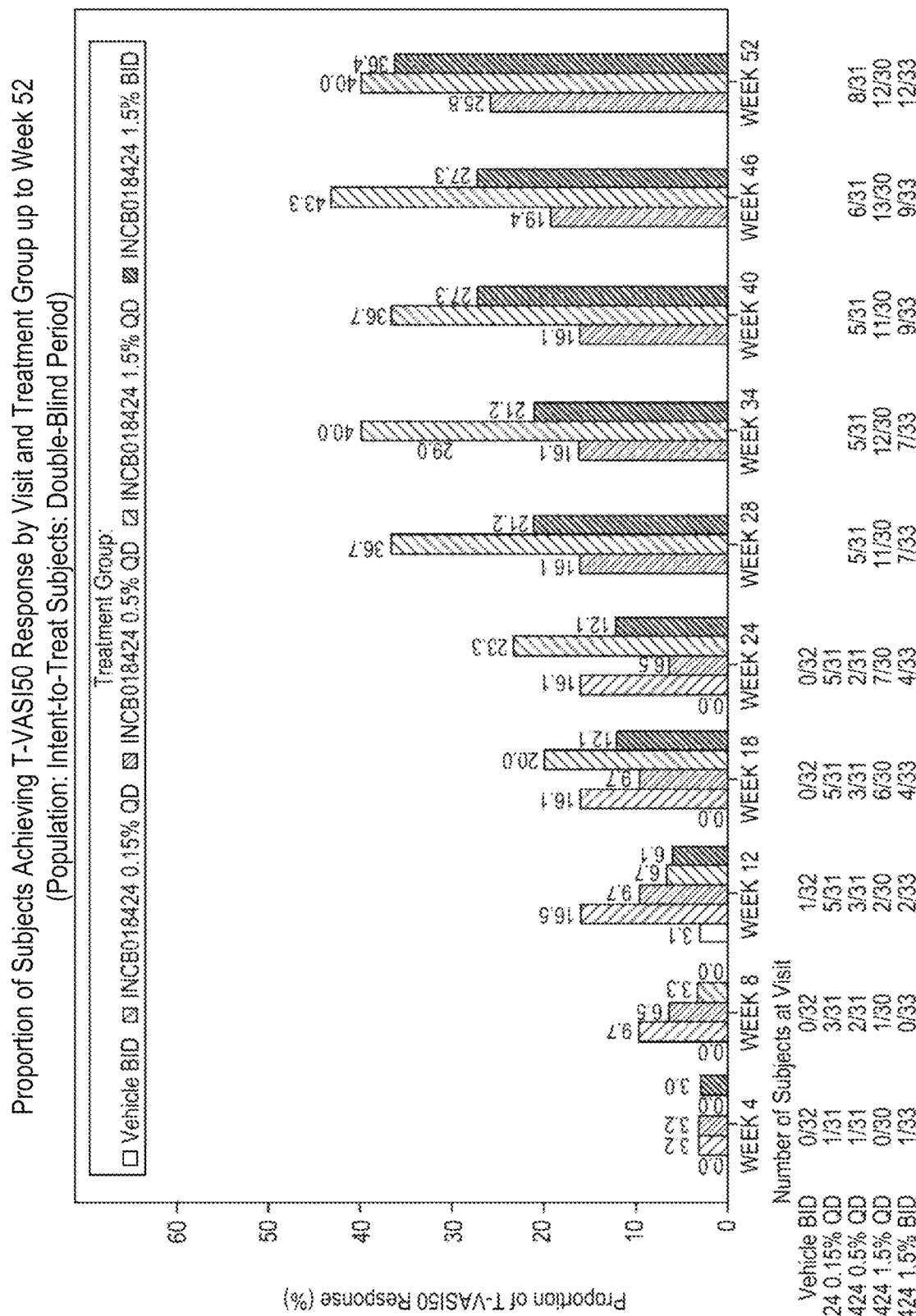
FIG. 18 is a graph depicting the proportion of subjects achieving T-VASI50 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period by a LOCF imputation method.
Figure 19:
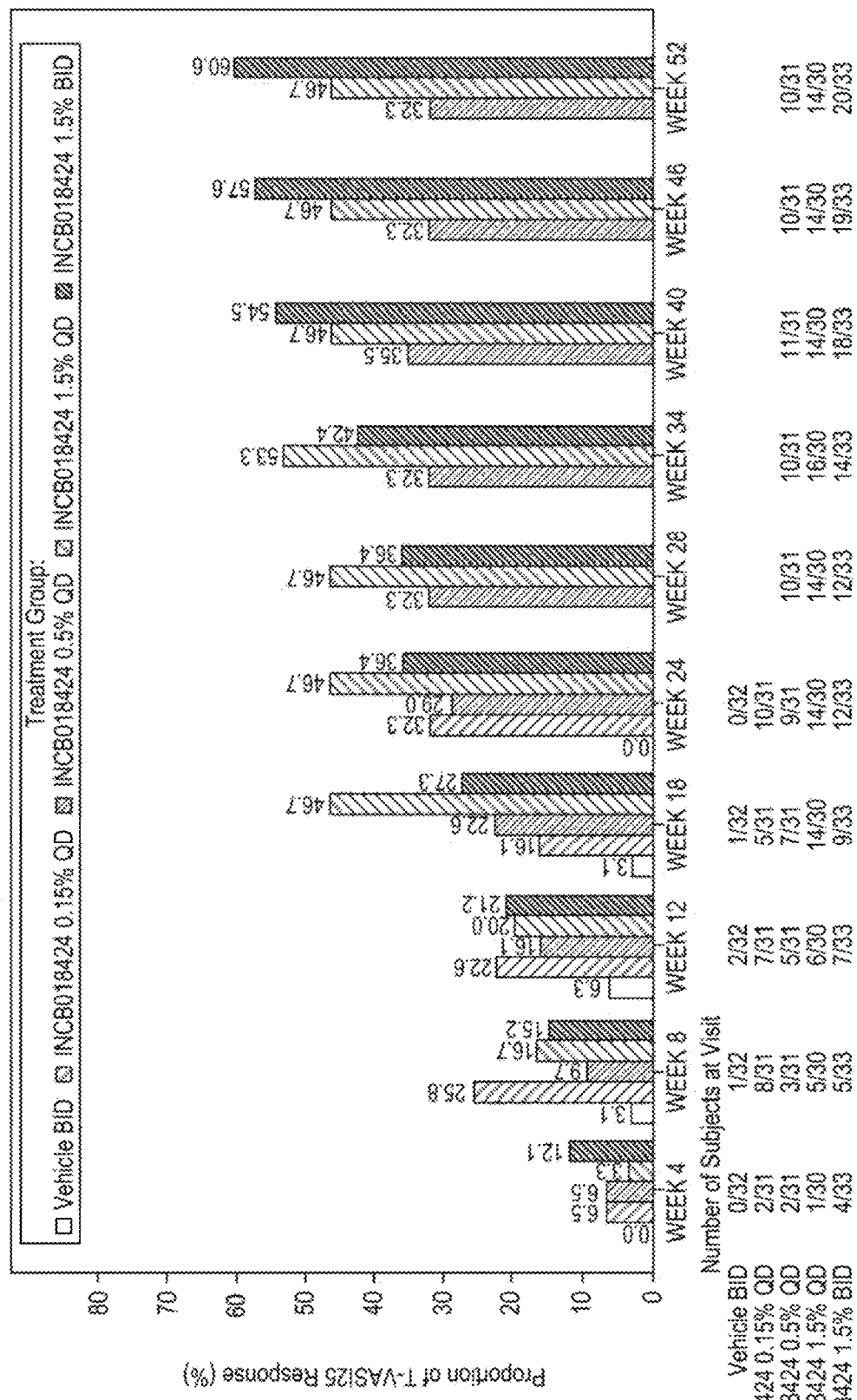
FIG. 19 is a graph depicting the proportion of subjects achieving T-VASI25 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 20:
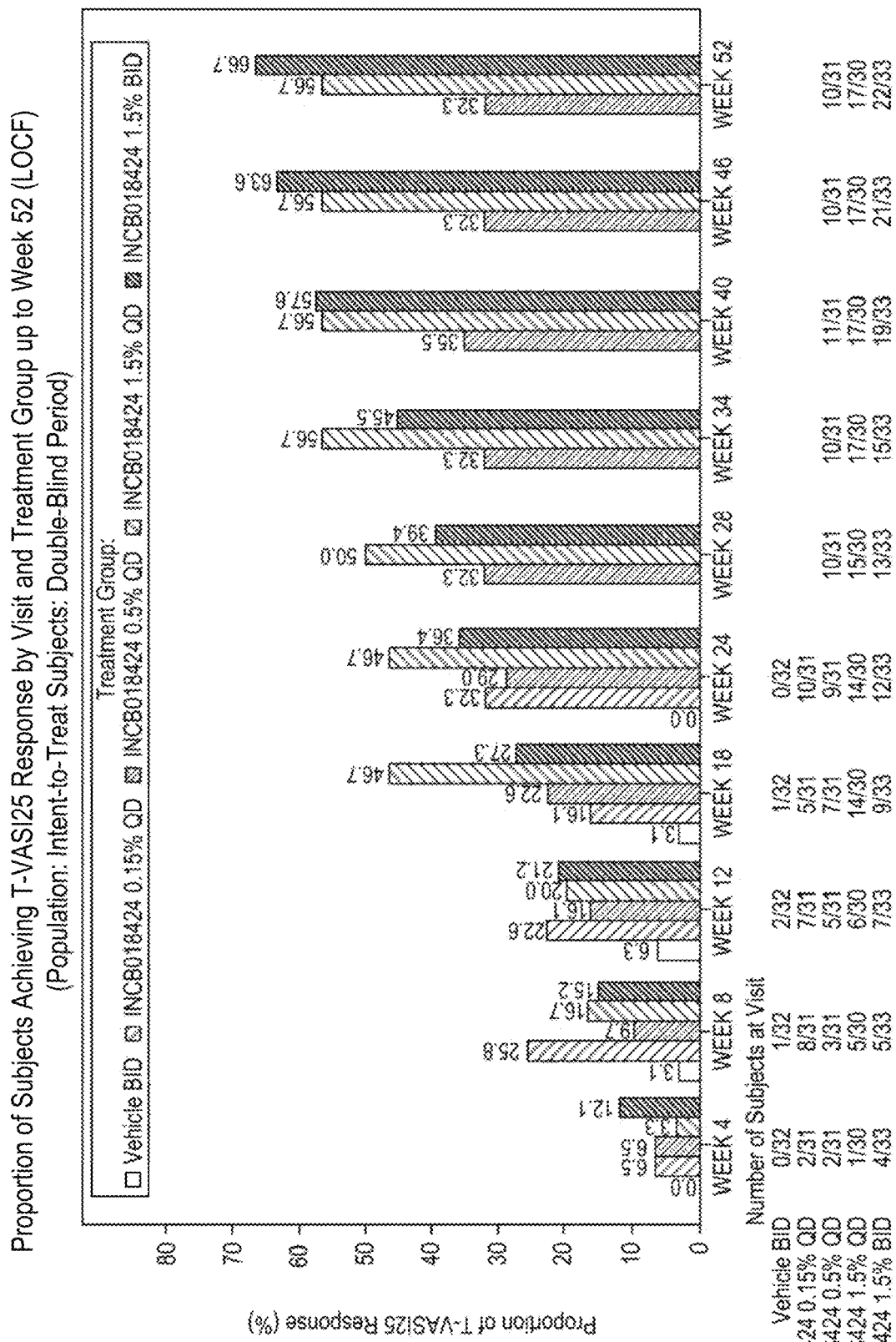
FIG. 20 is a graph depicting the proportion of subjects achieving T-VASI25 response by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period by a LOCF imputation method.
Figure 21:
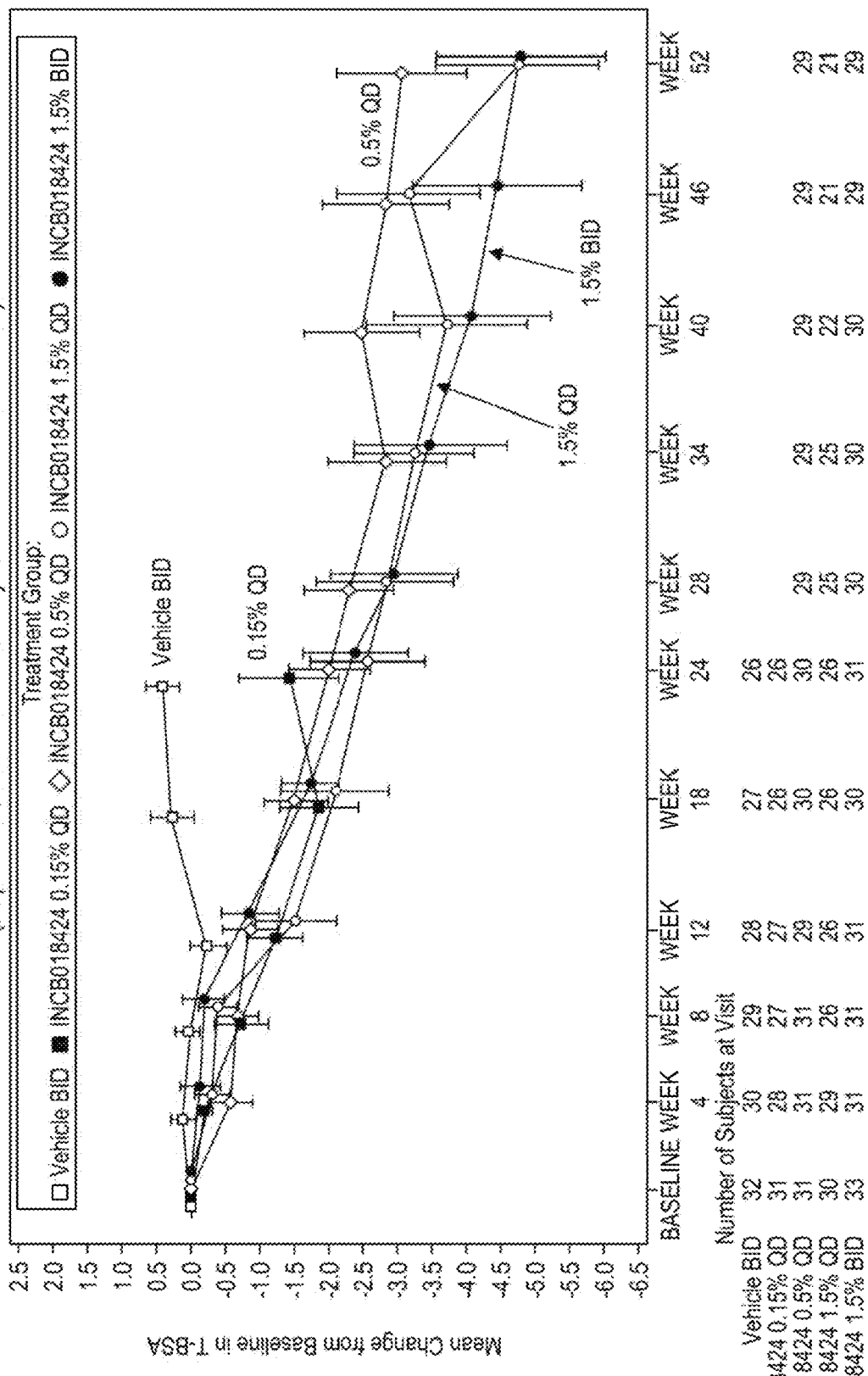
FIG. 21 is a graph depicting mean change from baseline in T-BSA score by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 22:
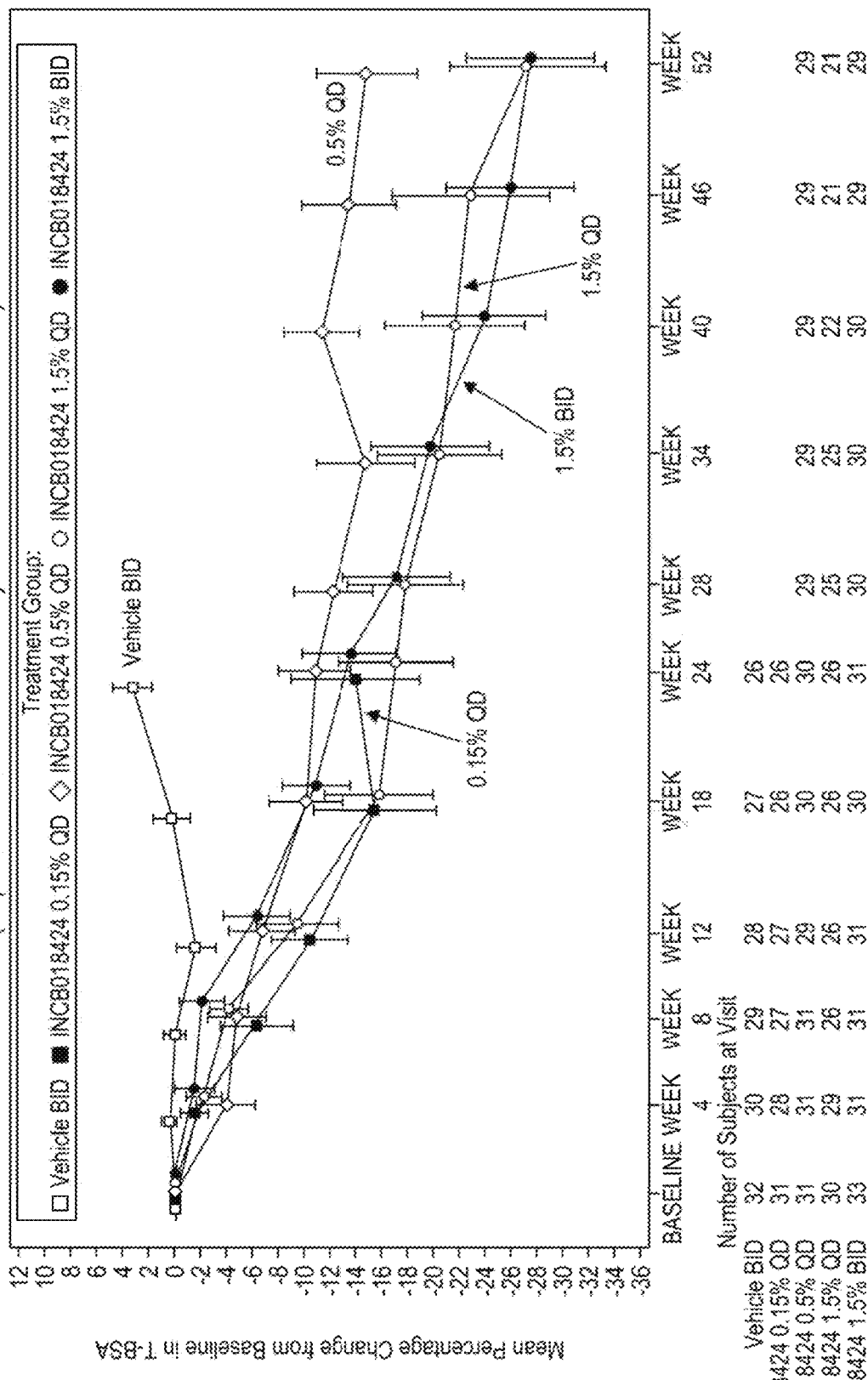
FIG. 22 is a graph depicting mean percentage change from baseline in T-BSA score by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 23:
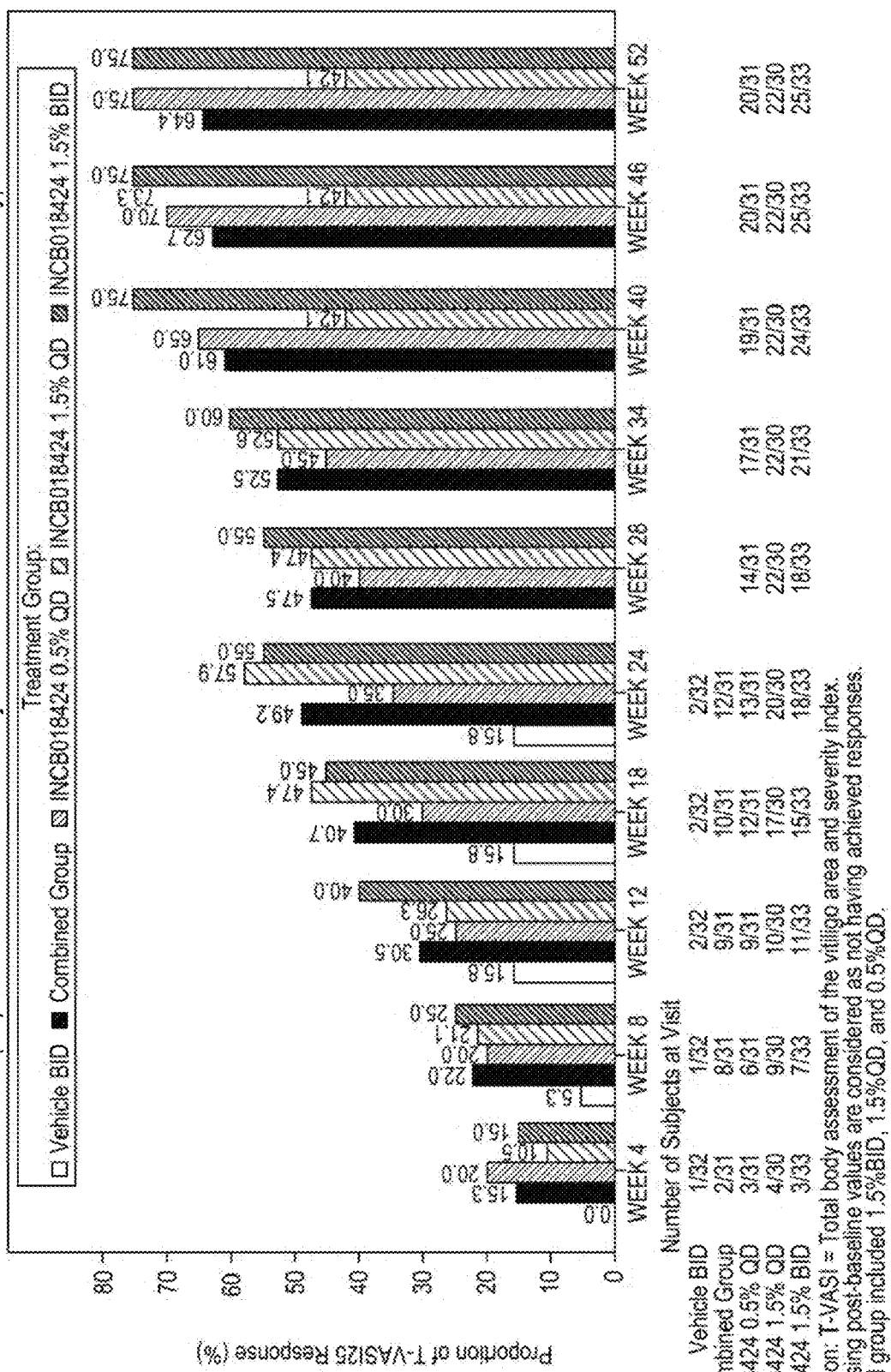
FIG. 23 is a graph depicting the proportion of subjects achieving T-VASI25 response (head and neck only) by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 24:
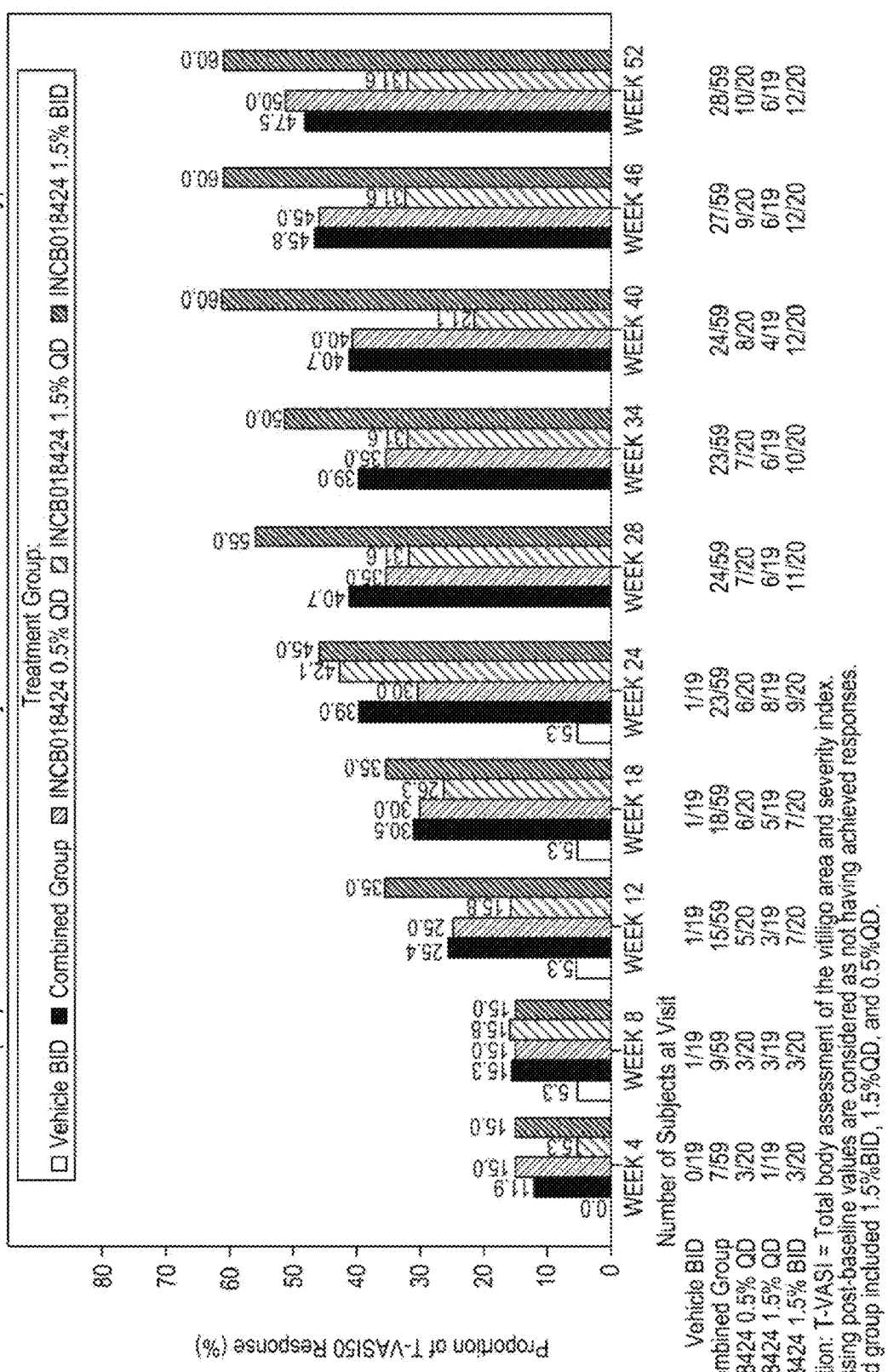
FIG. 24 is a graph depicting the proportion of subjects achieving T-VASI50 response (head and neck only) by visit and treatment group at Week 4, Week 8, Week 12, Week 18, Week 24. Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 25:
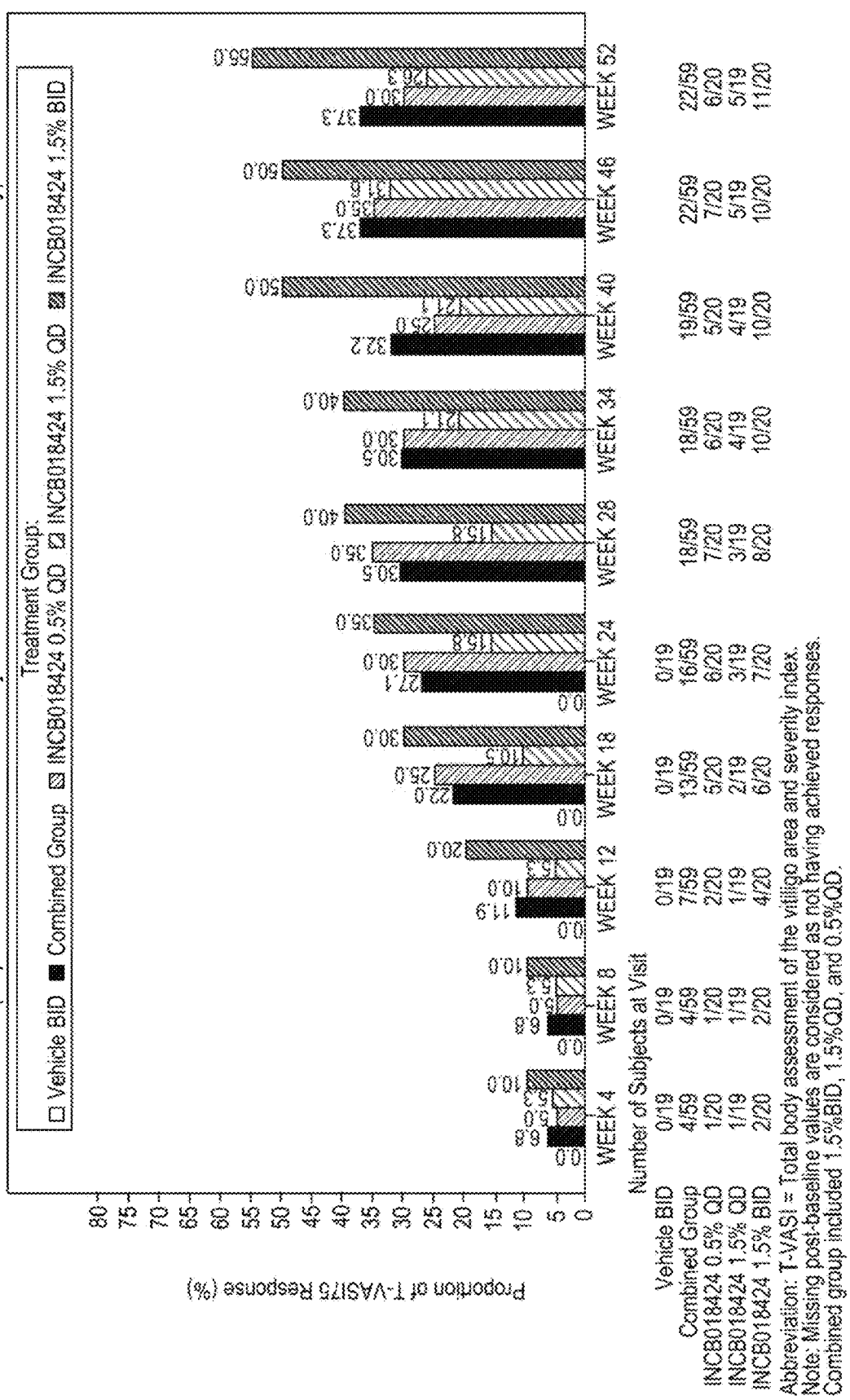
FIG. 25 is a graph depicting the proportion of subjects achieving T-VASI75 response (head and neck only) by visit and treatment group at Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 26:
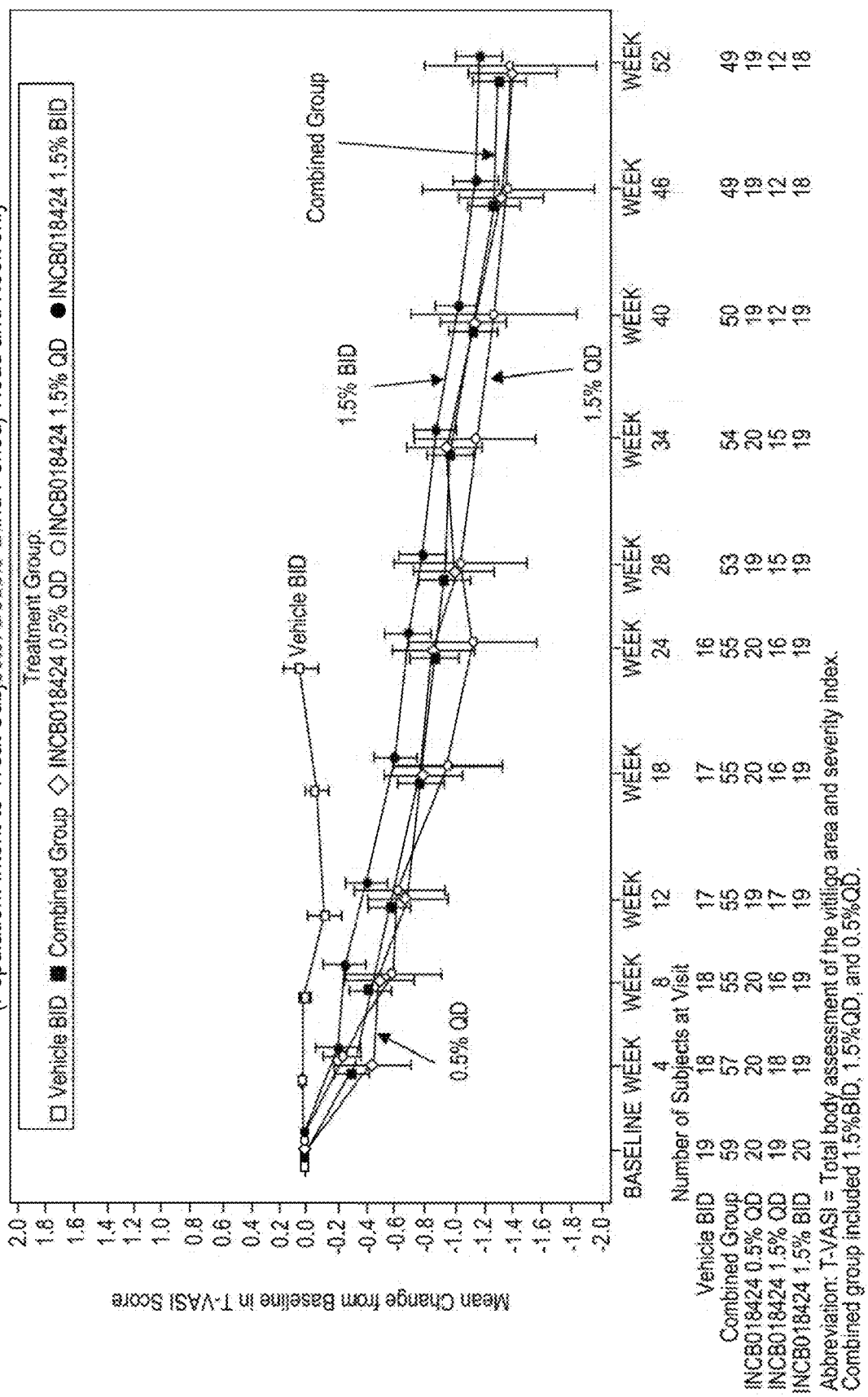
FIG. 26 is a graph depicting mean change from baseline in T-VASI score (head and neck only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 27:
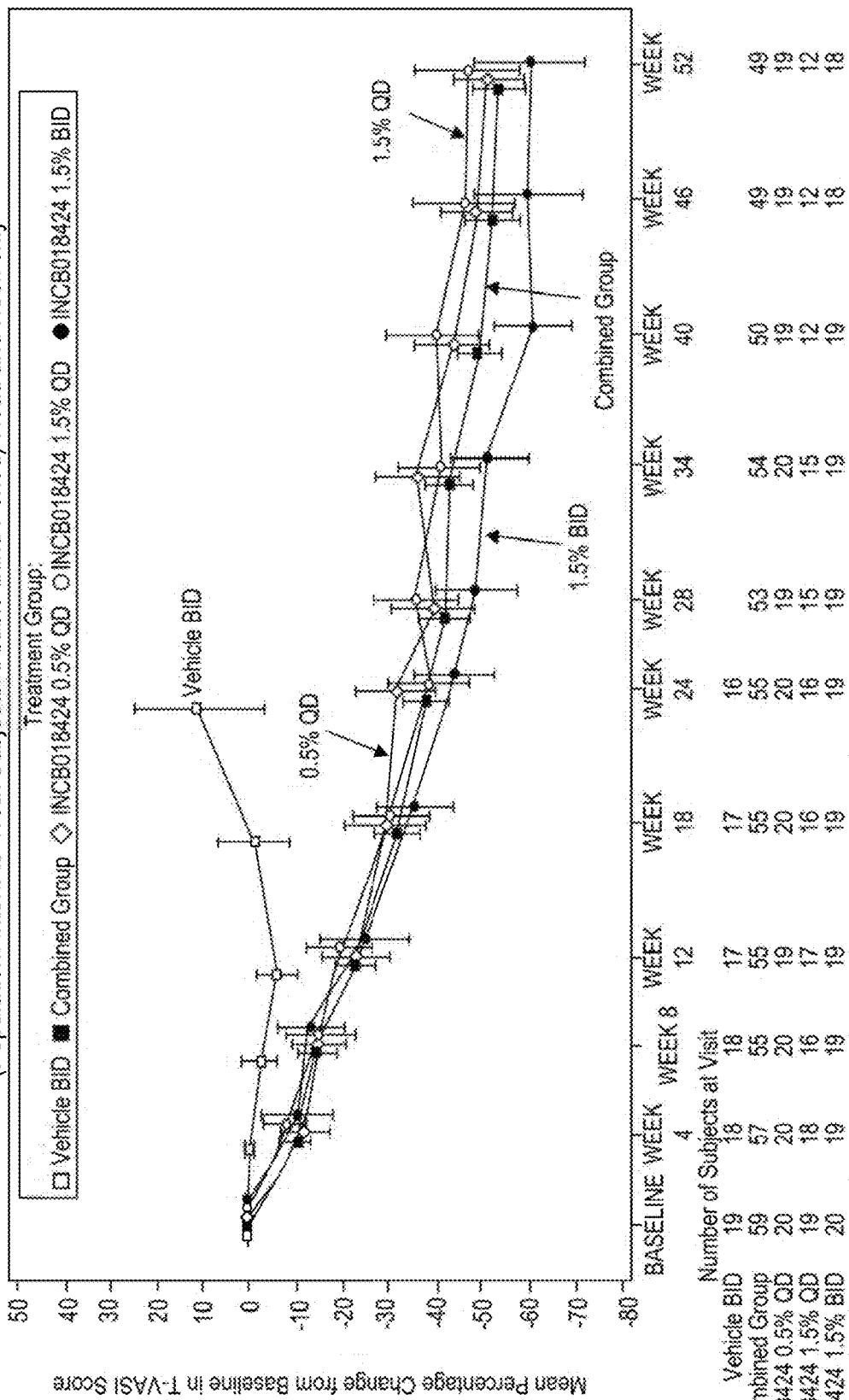
FIG. 27 is a graph depicting mean percentage change from baseline in T-VASI score (head and neck only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 28:
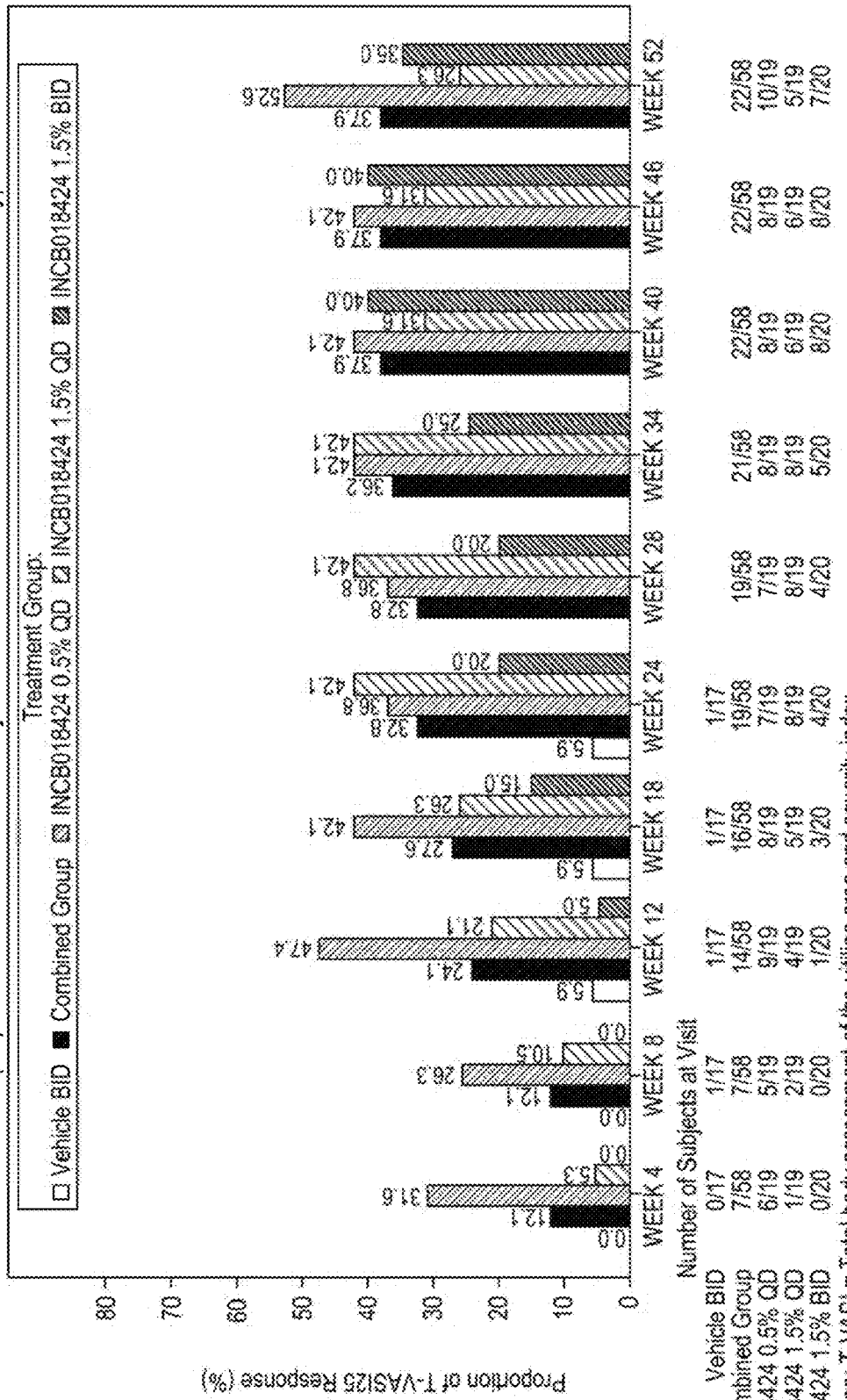
FIG. 28 is a graph depicting proportion of T-VASI25 response (hands only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 29:
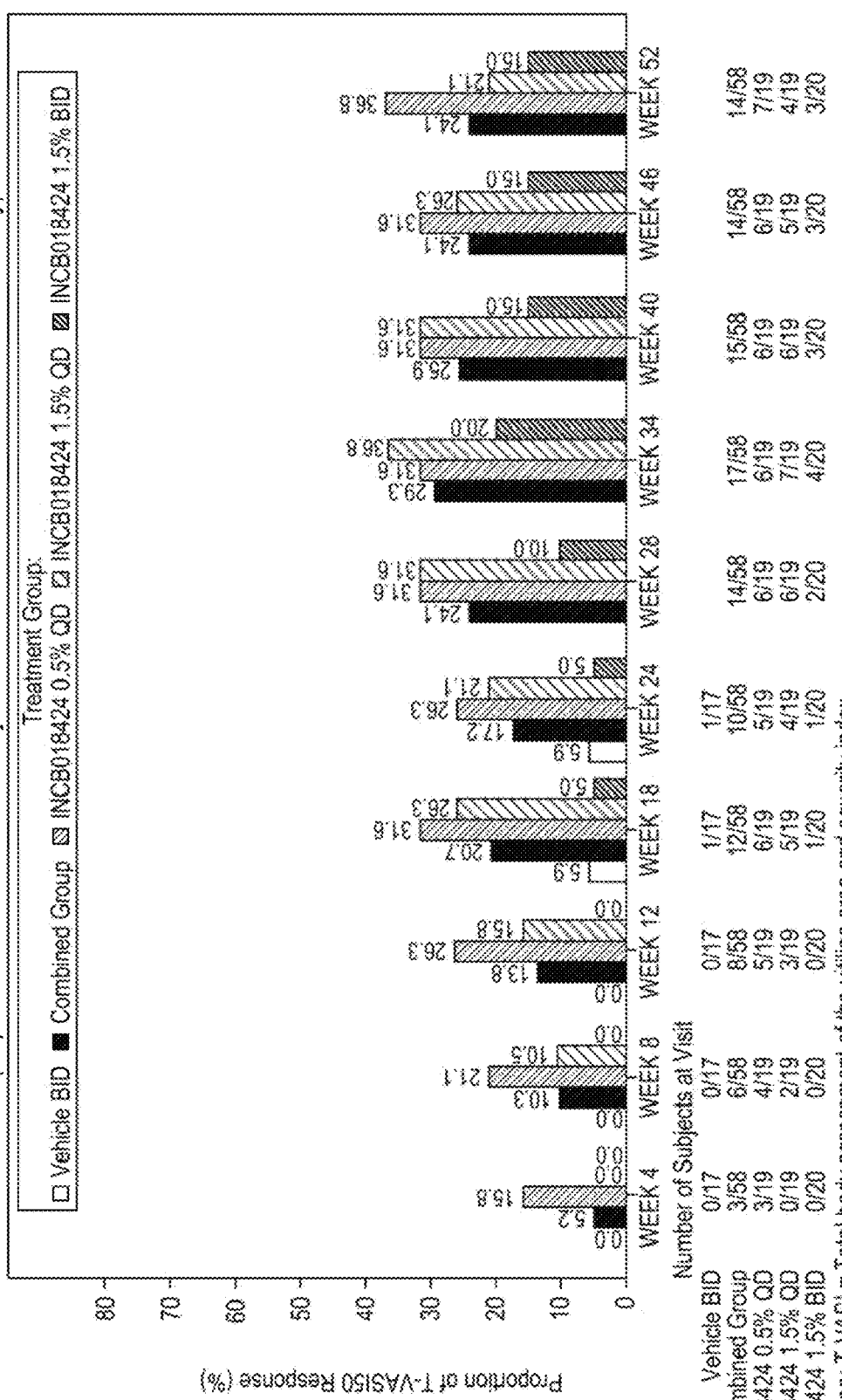
FIG. 29 is a graph depicting proportion of T-VASI50 response (hands only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 30:
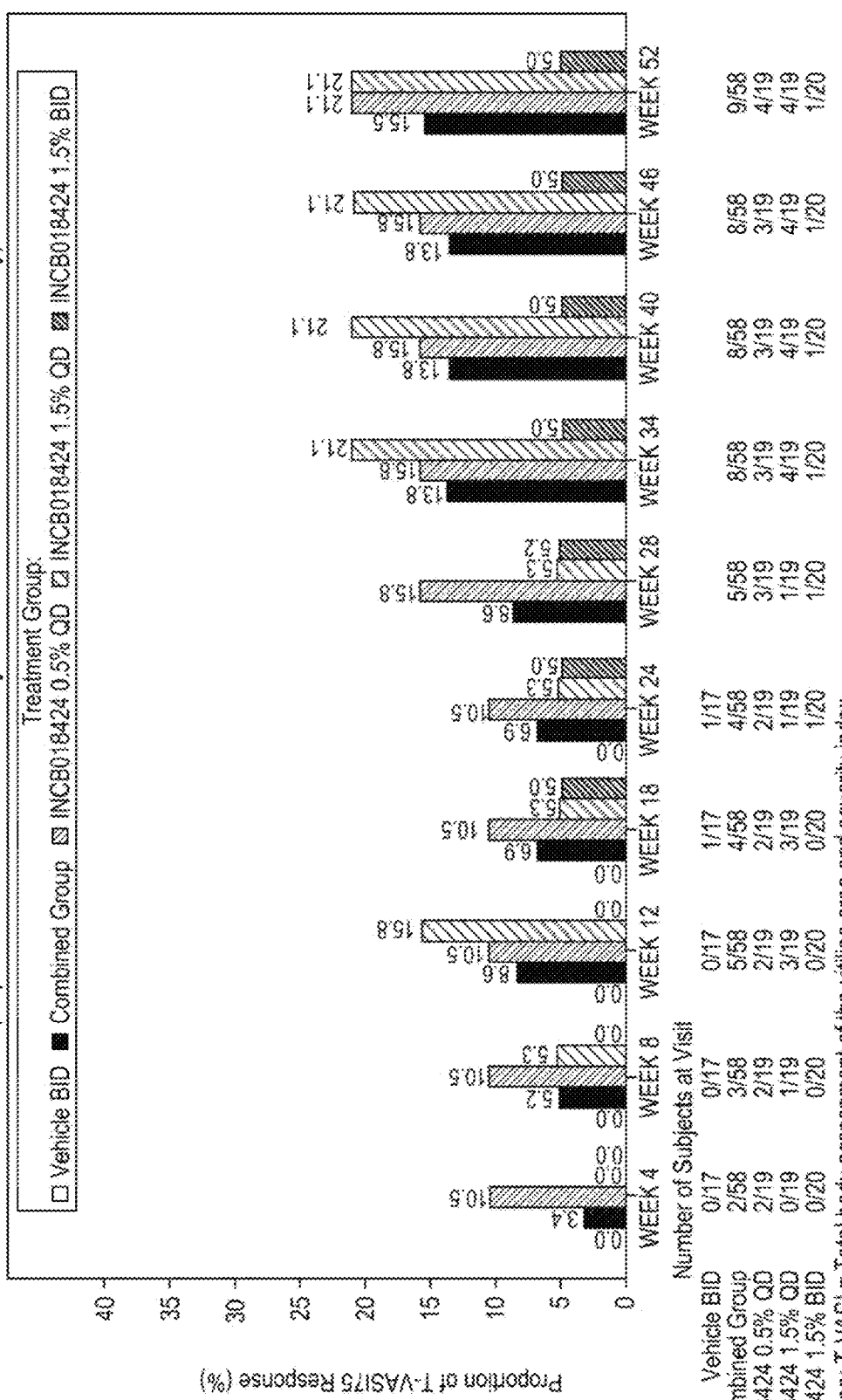
FIG. 30 is a graph depicting proportion of T-VASI75 response (hands only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 31:
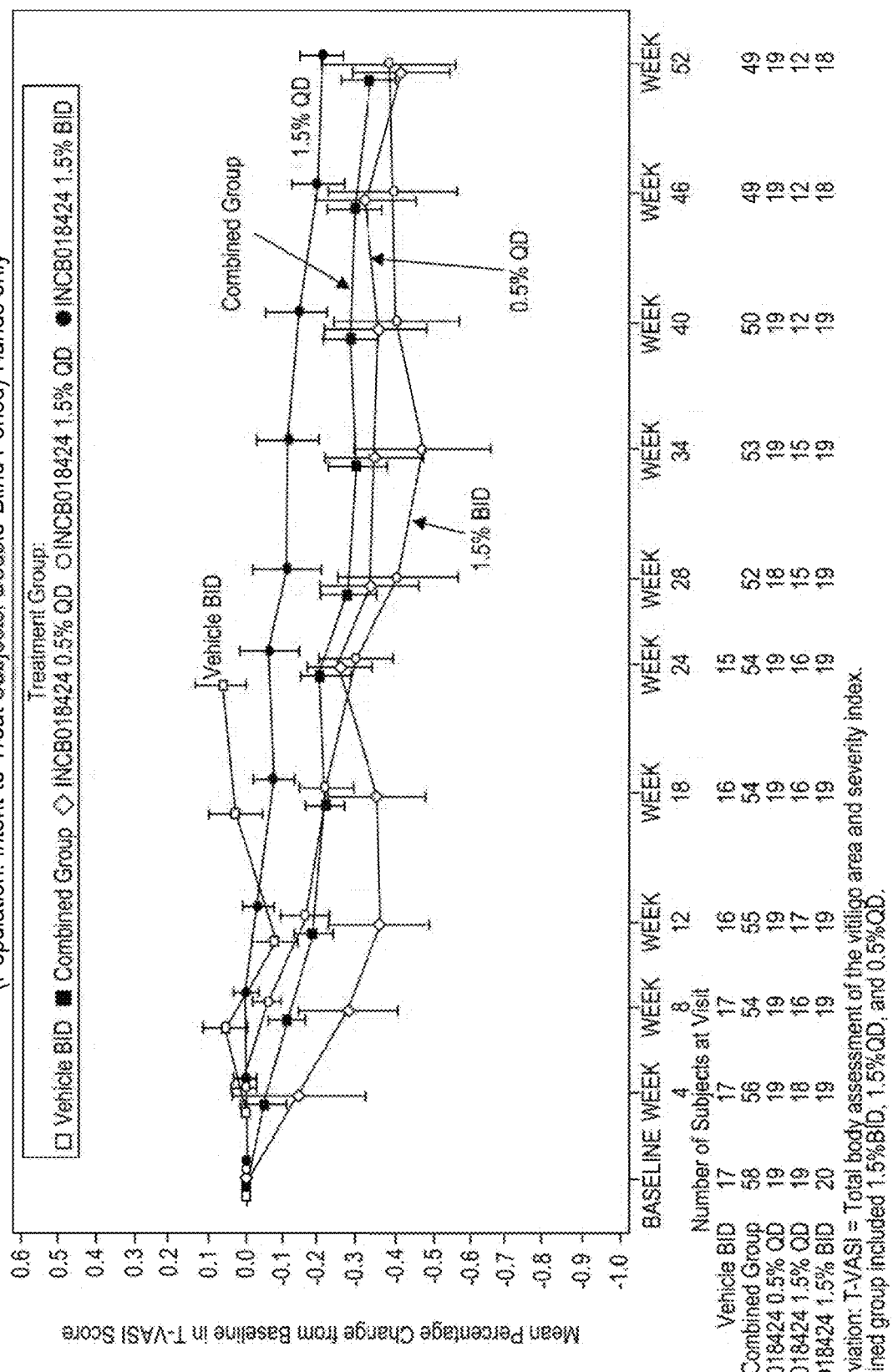
FIG. 31 is a graph depicting mean change from baseline in T-VASI score (hands only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 32:
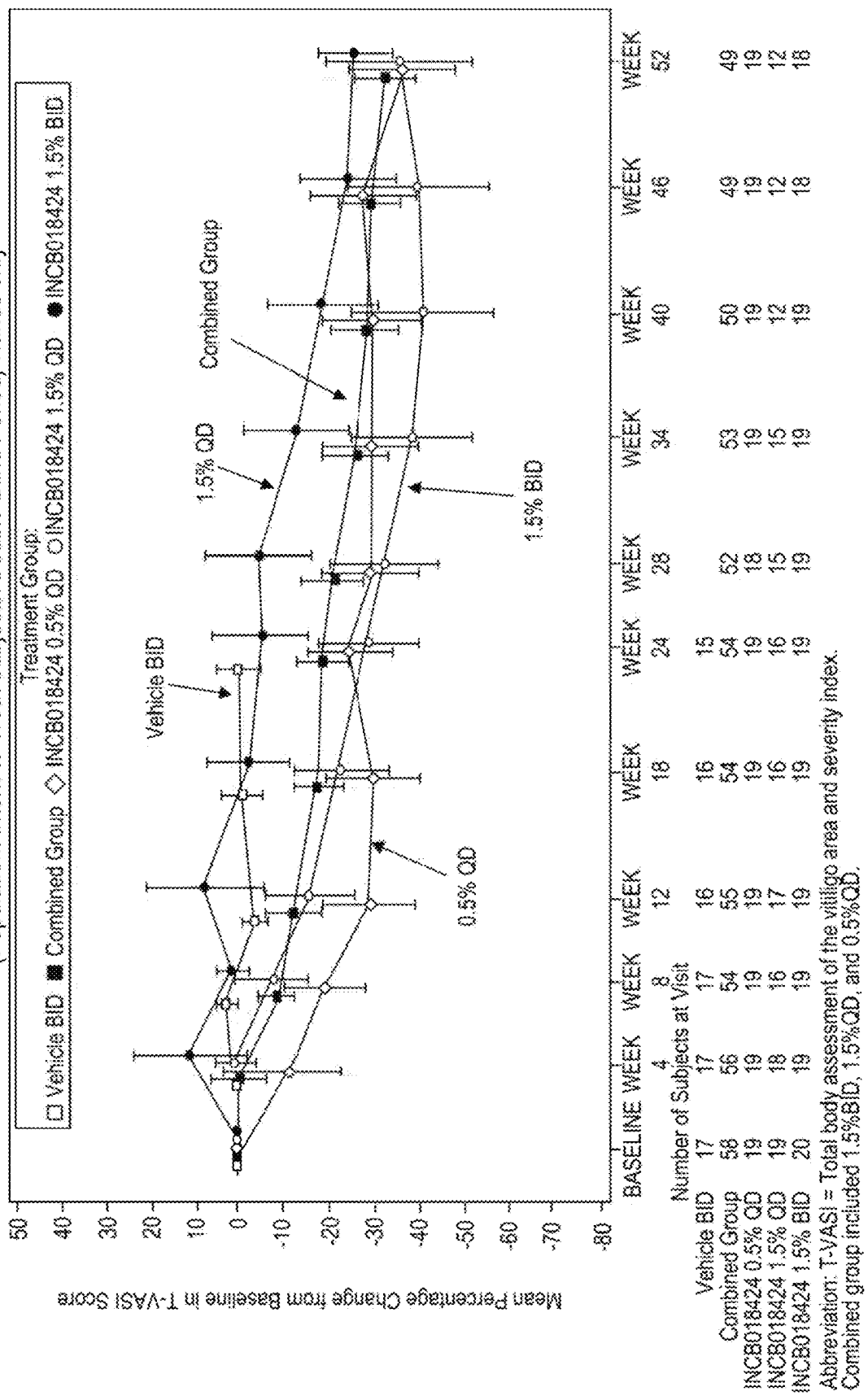
FIG. 32 is a graph depicting mean percentage change from baseline in T-VASI score (hands only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 33:
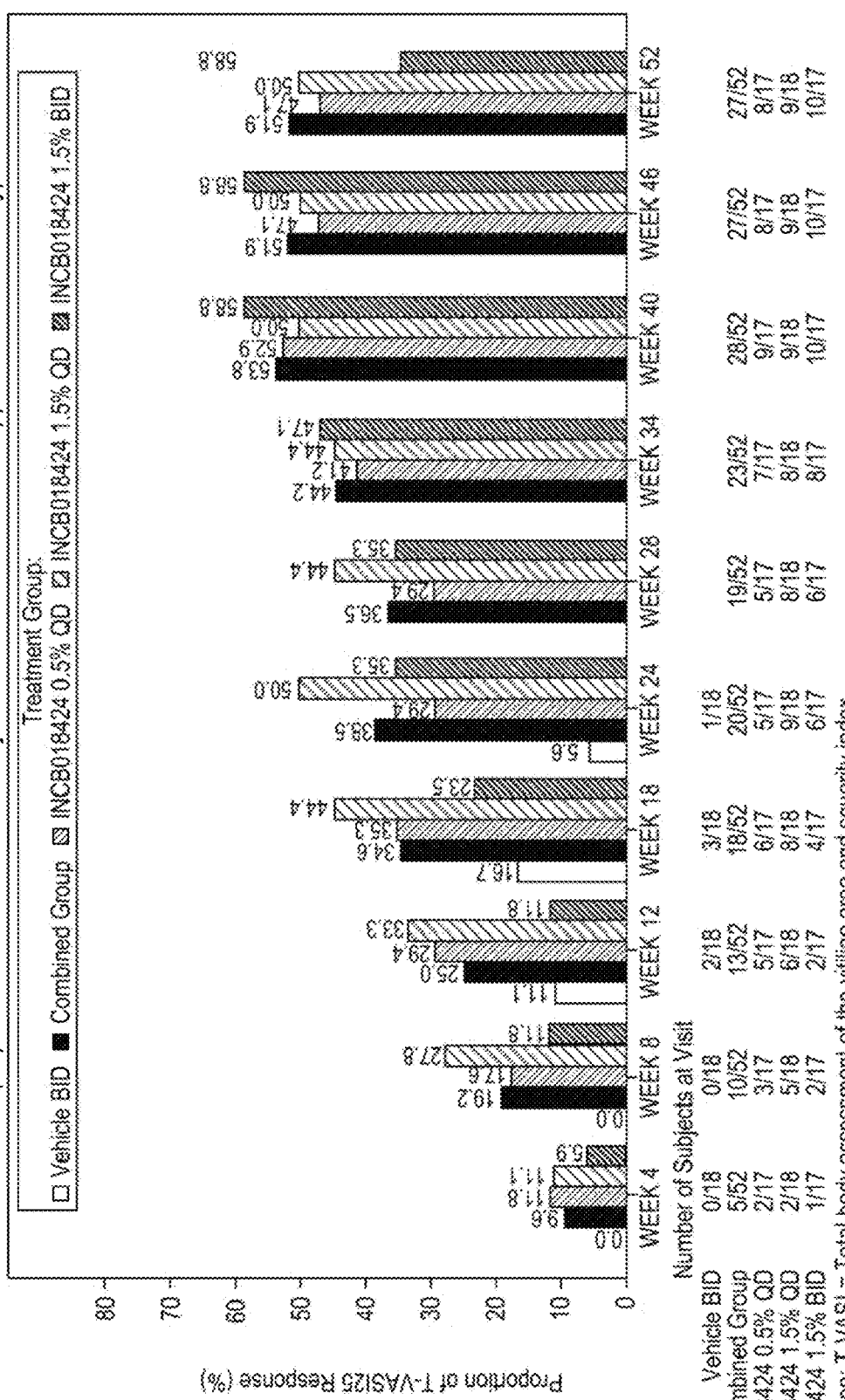
FIG. 33 is a graph depicting proportion of T-VASI25 response (upper extremities only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 34:
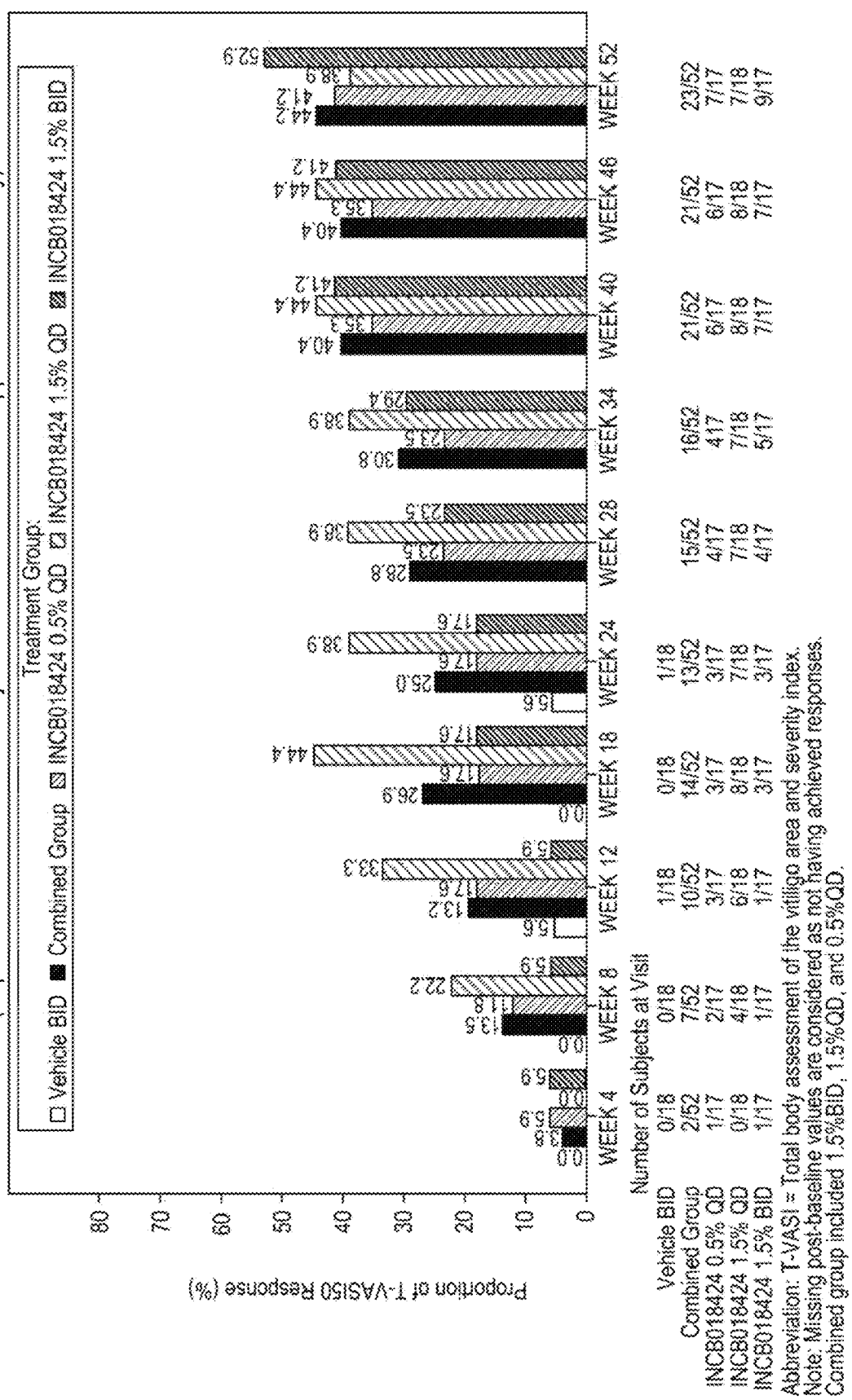
FIG. 34 is a graph depicting proportion of T-VASI50 response (upper extremities only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 35:
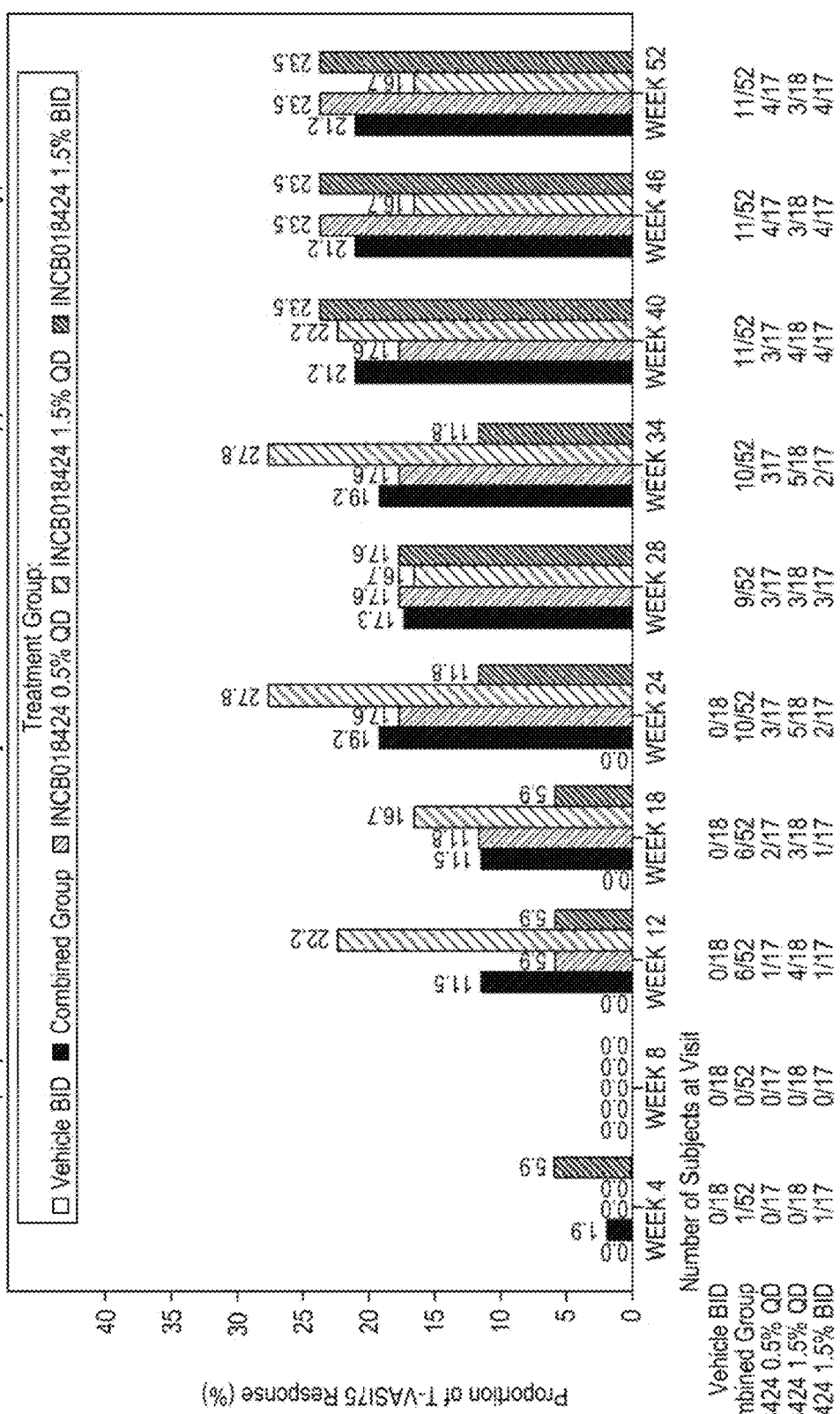
FIG. 35 is a graph depicting proportion of T-VASI75 response (upper extremities only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 36:
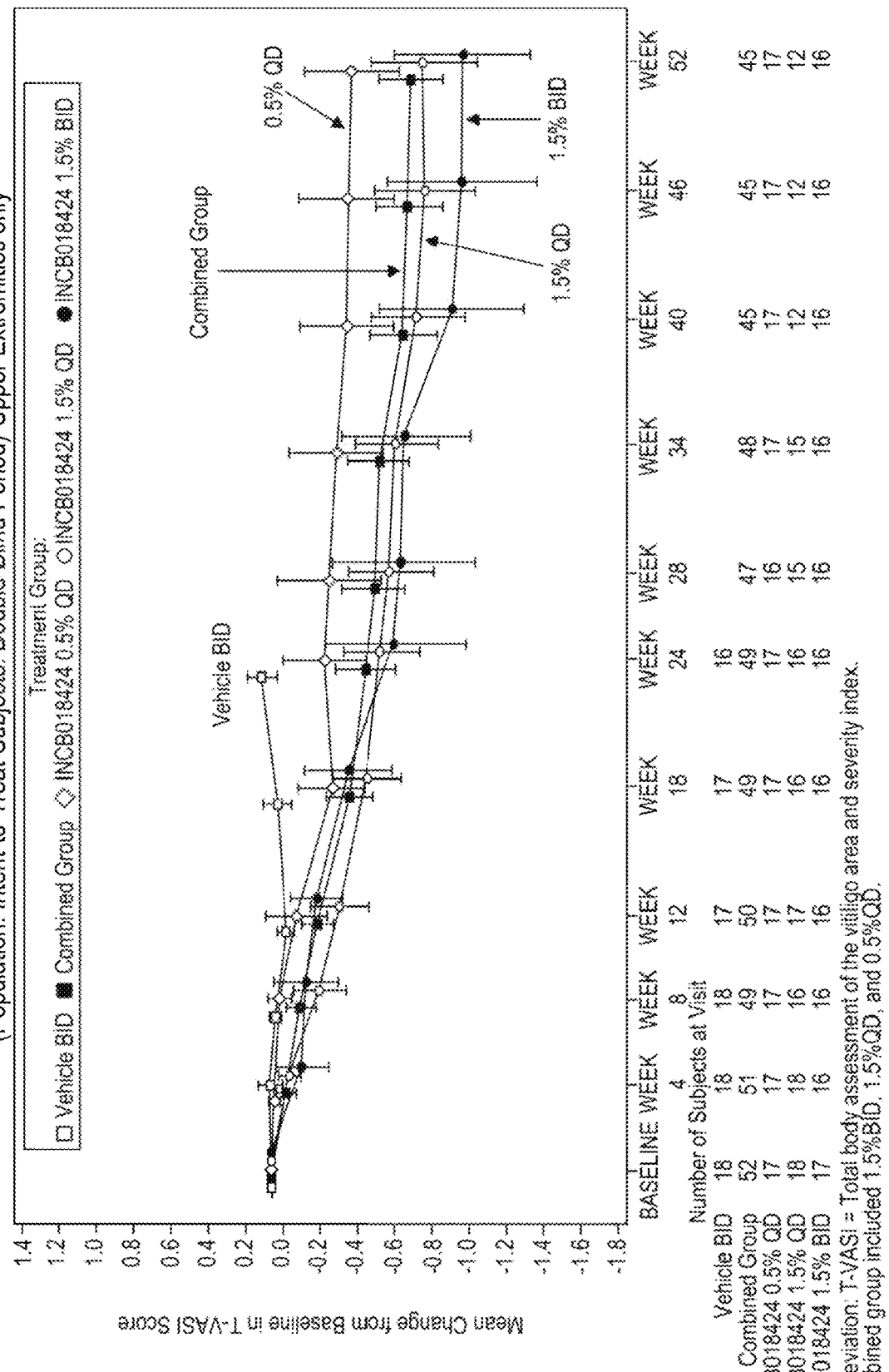
FIG. 36 is a graph depicting mean change from baseline in T-VASI score (upper extremities only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 37:
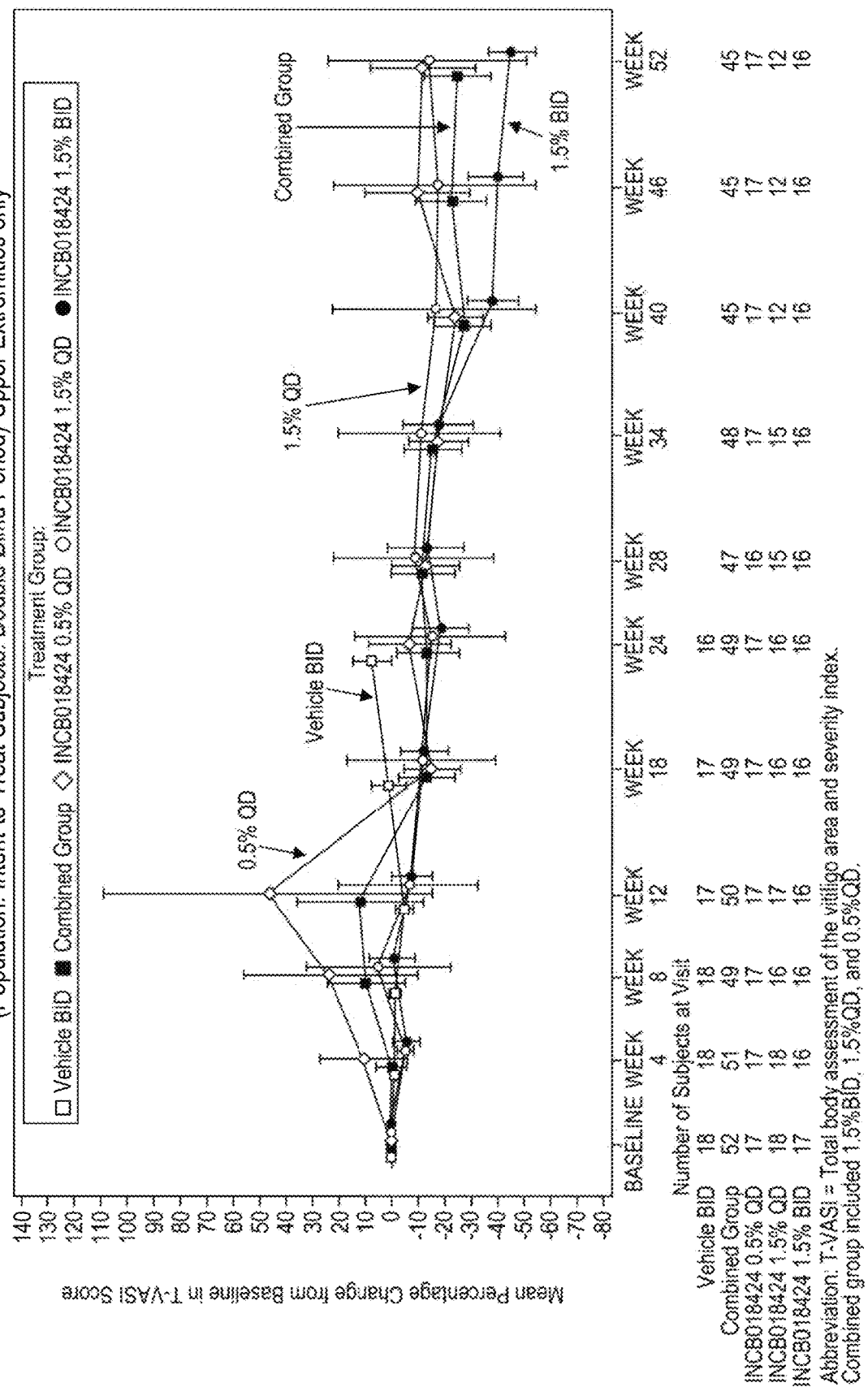
FIG. 37 is a graph depicting mean percentage change from baseline in T-VASI score (upper extremities only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 38:
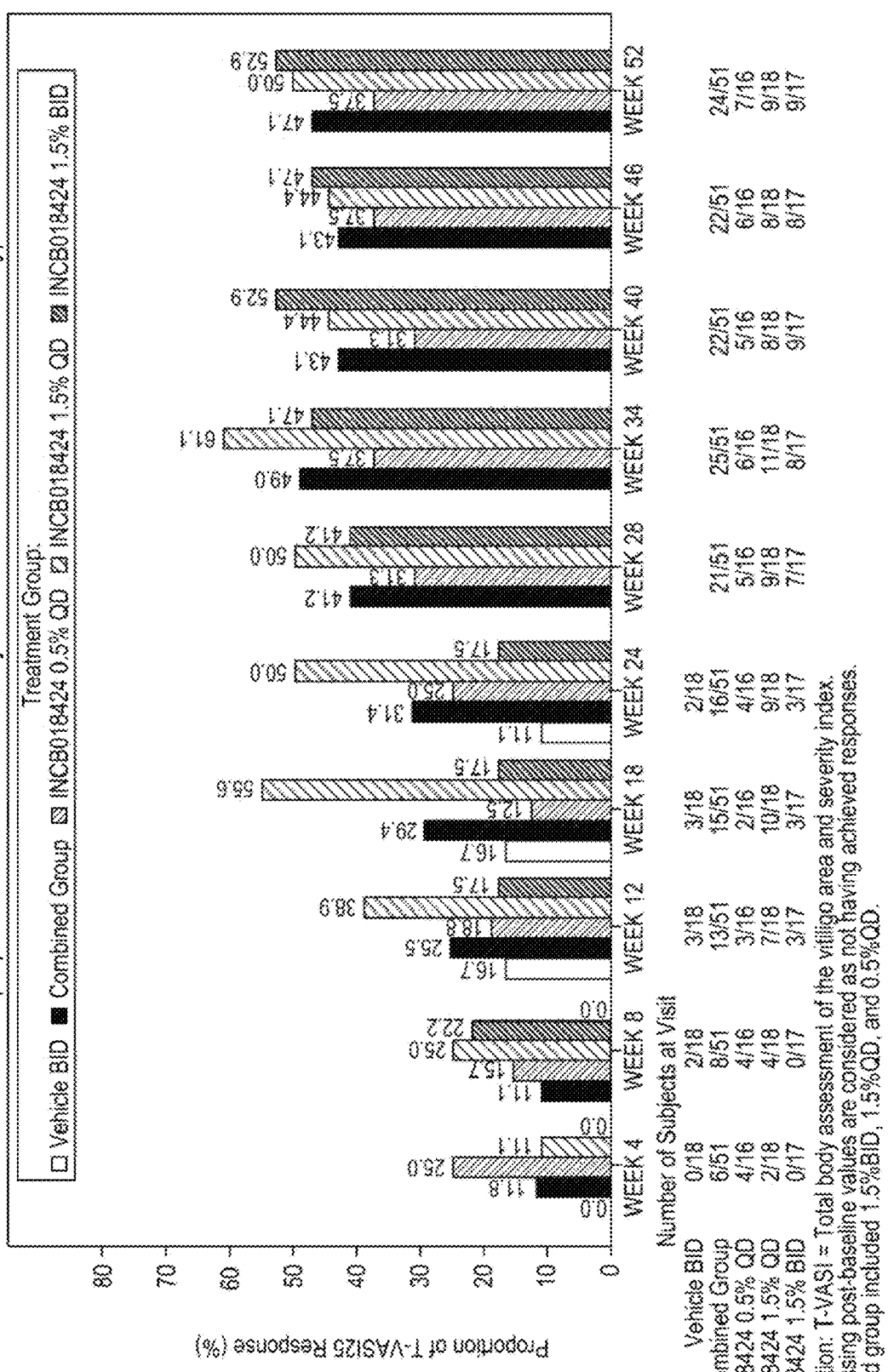
FIG. 38 is a graph depicting proportion of T-VASI25 response (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 39:
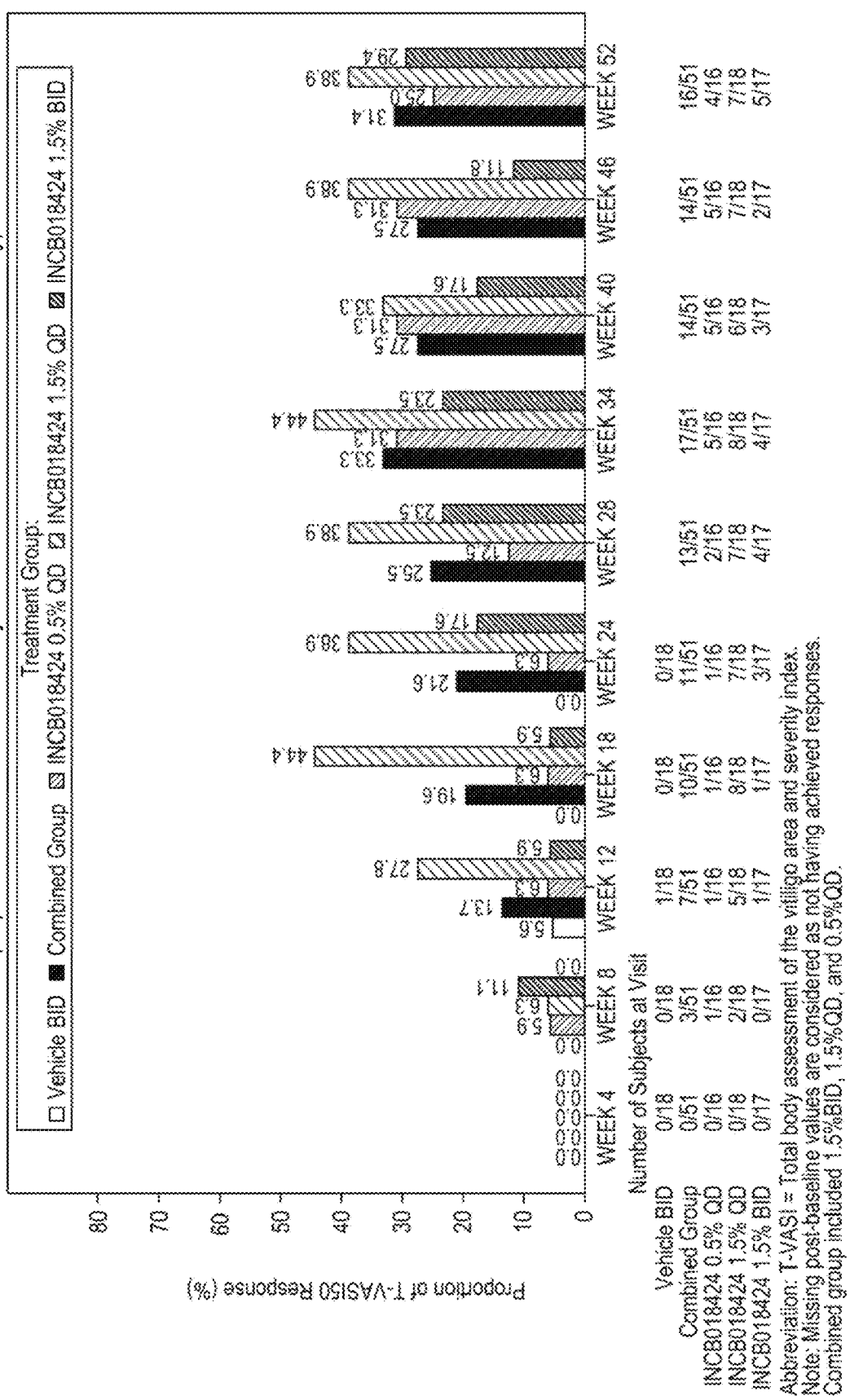
FIG. 39 is a graph depicting proportion of T-VASI50 response (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 40:
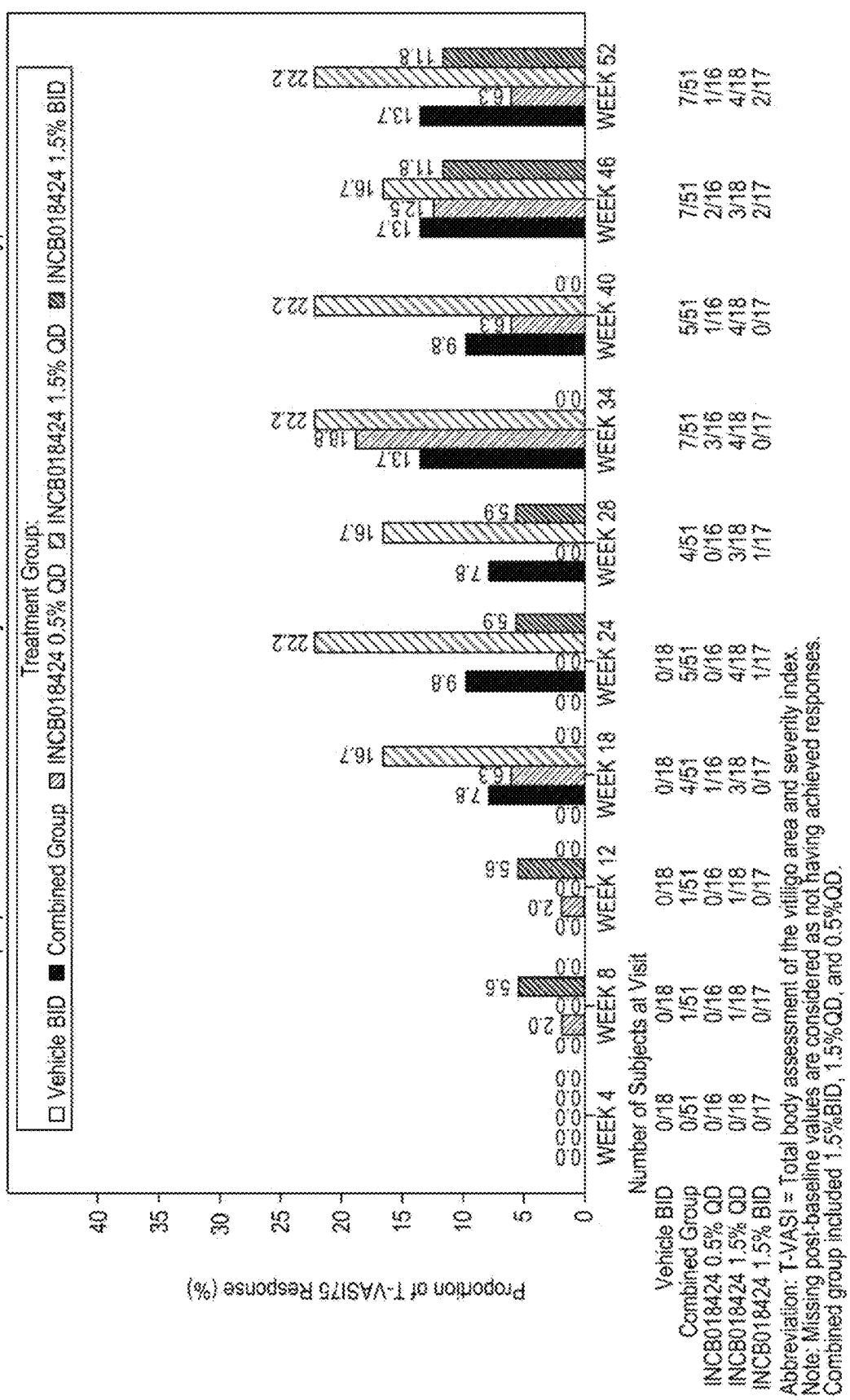
FIG. 40 is a graph depicting proportion of T-VASI75 response (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 41:
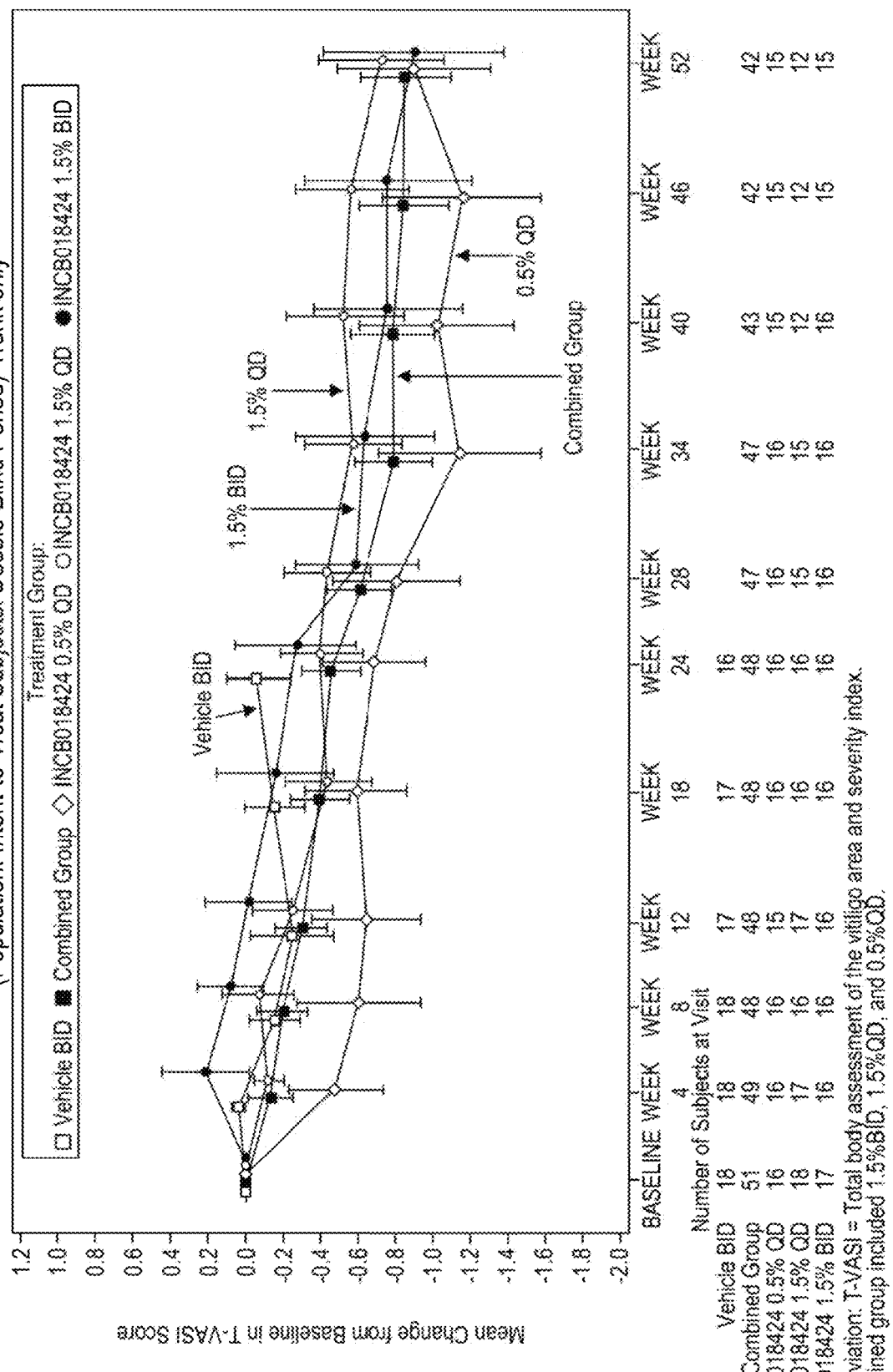
FIG. 41 is a graph depicting mean change from baseline in T-VASI score (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 42:
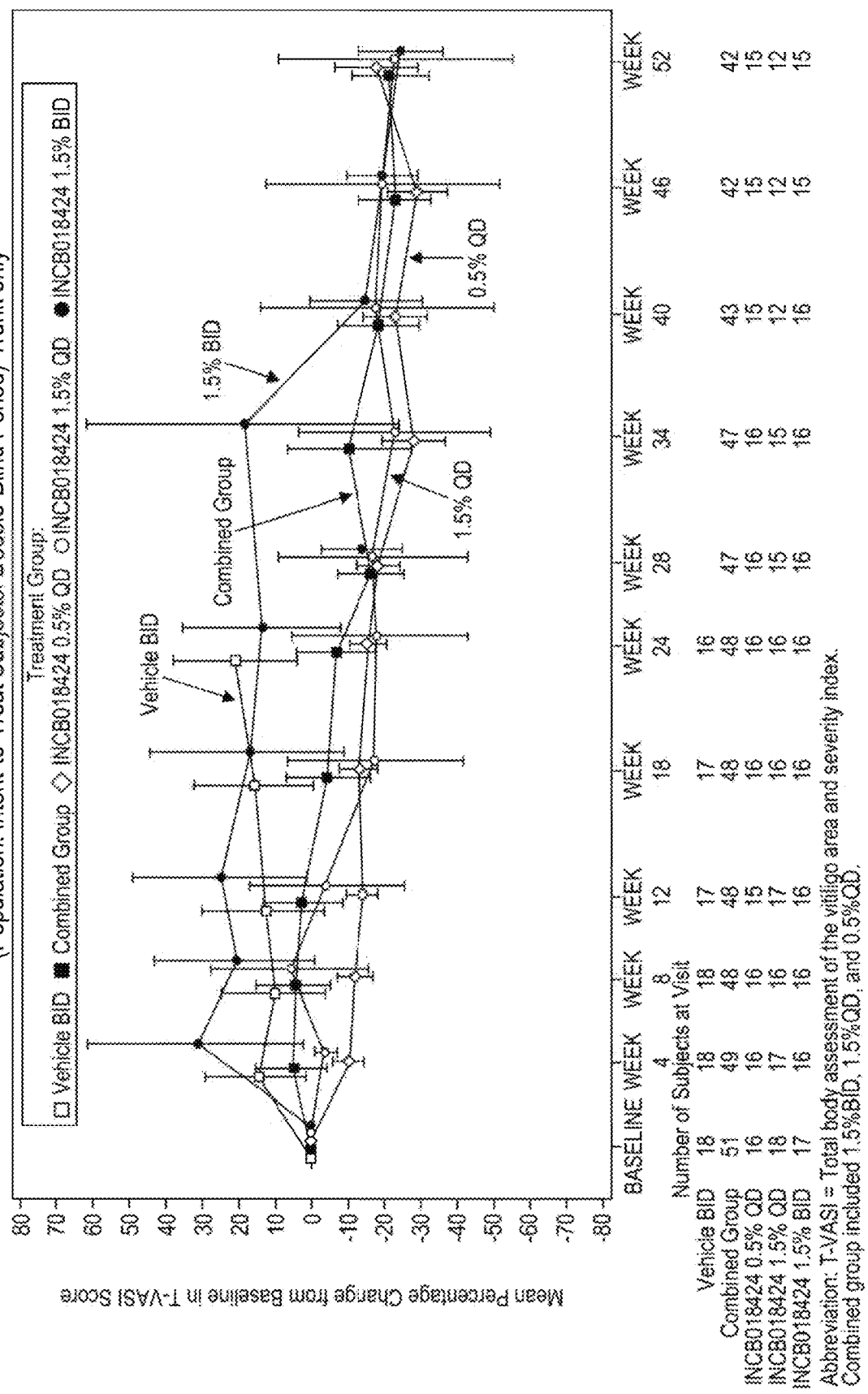
FIG. 42 is a graph depicting mean percentage change from baseline in T-VASI score trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 43:
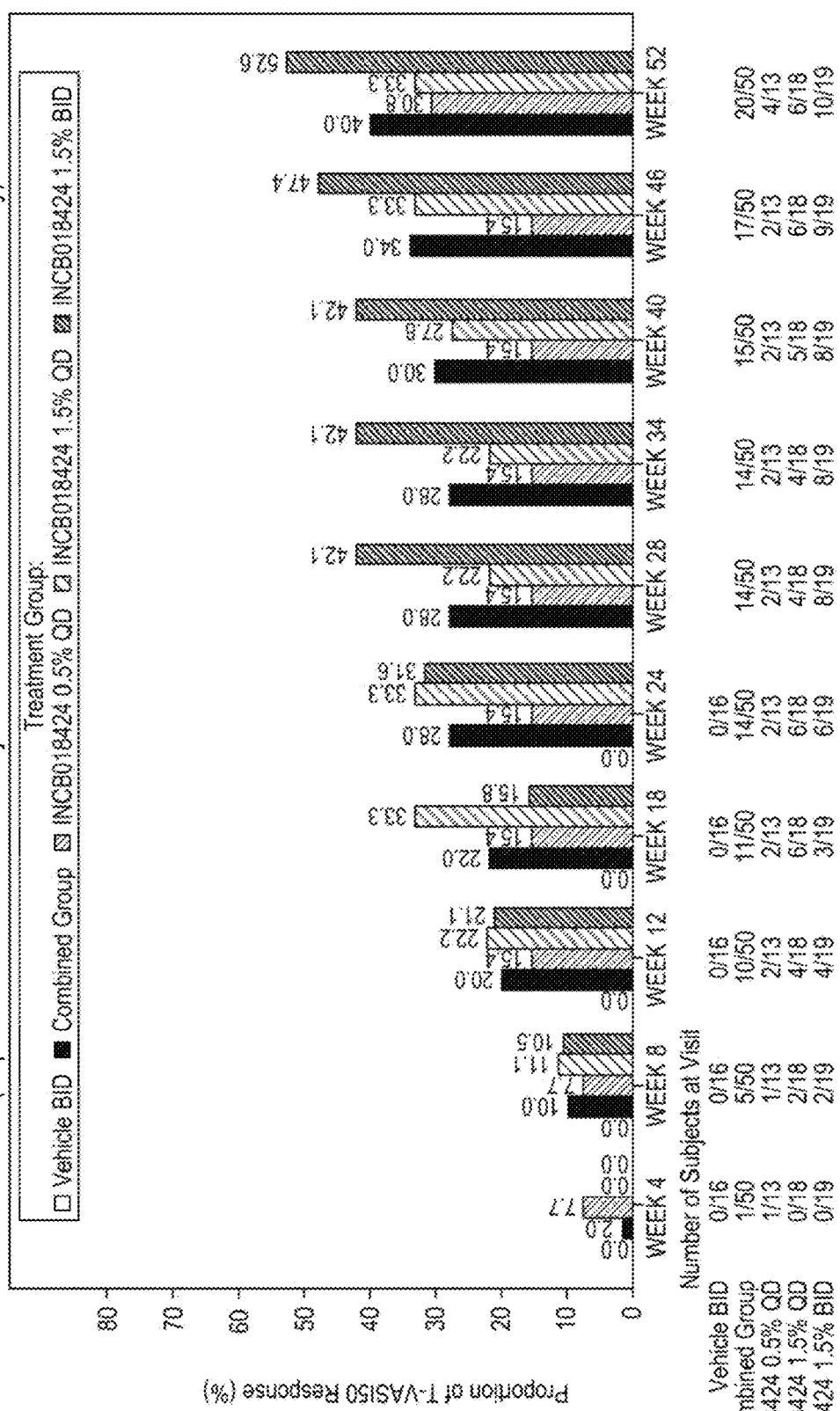
FIG. 43 is a graph depicting proportion of T-VASI50 response (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 44:
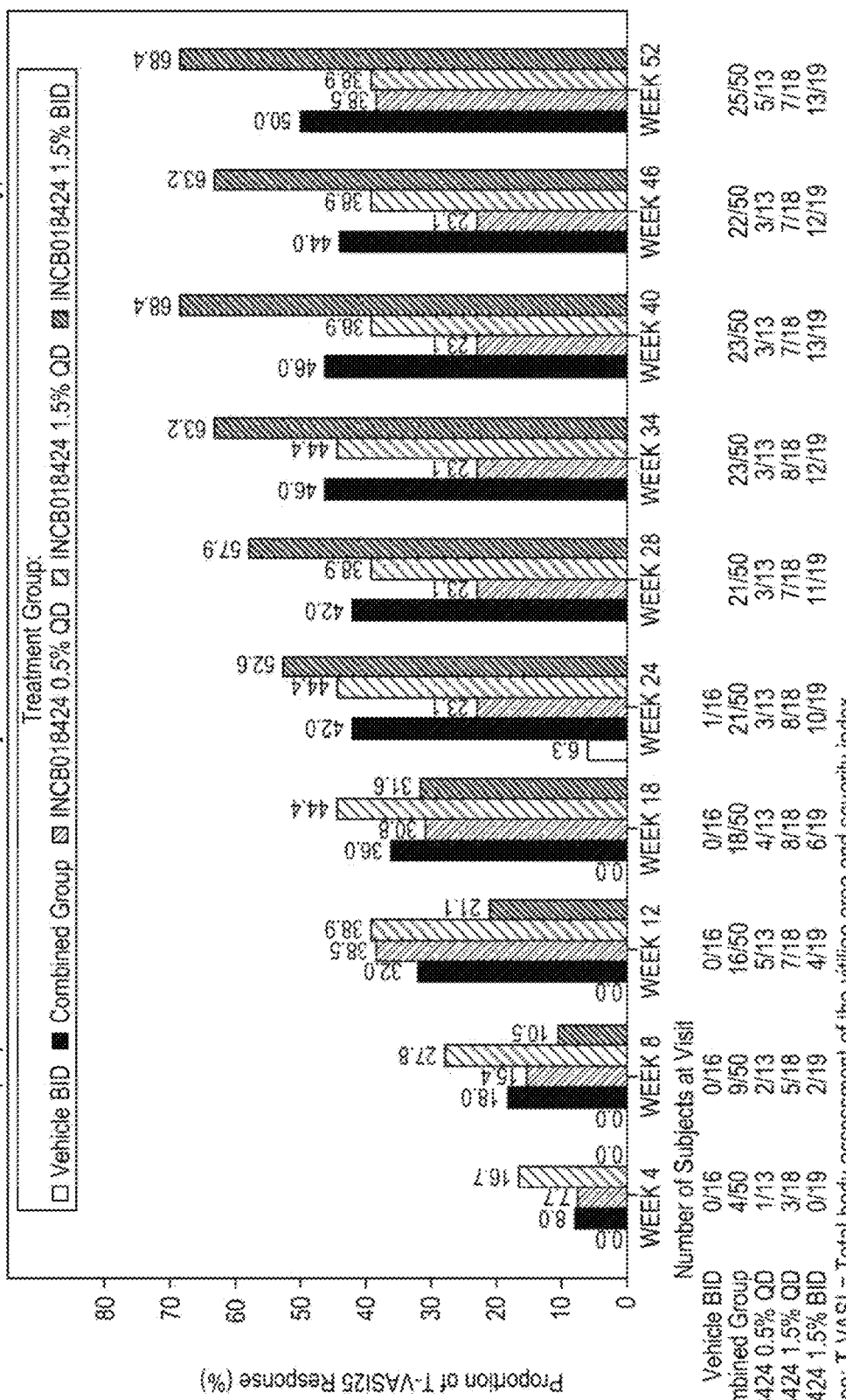
FIG. 44 is a graph depicting proportion of T-VASI25 response (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 45:
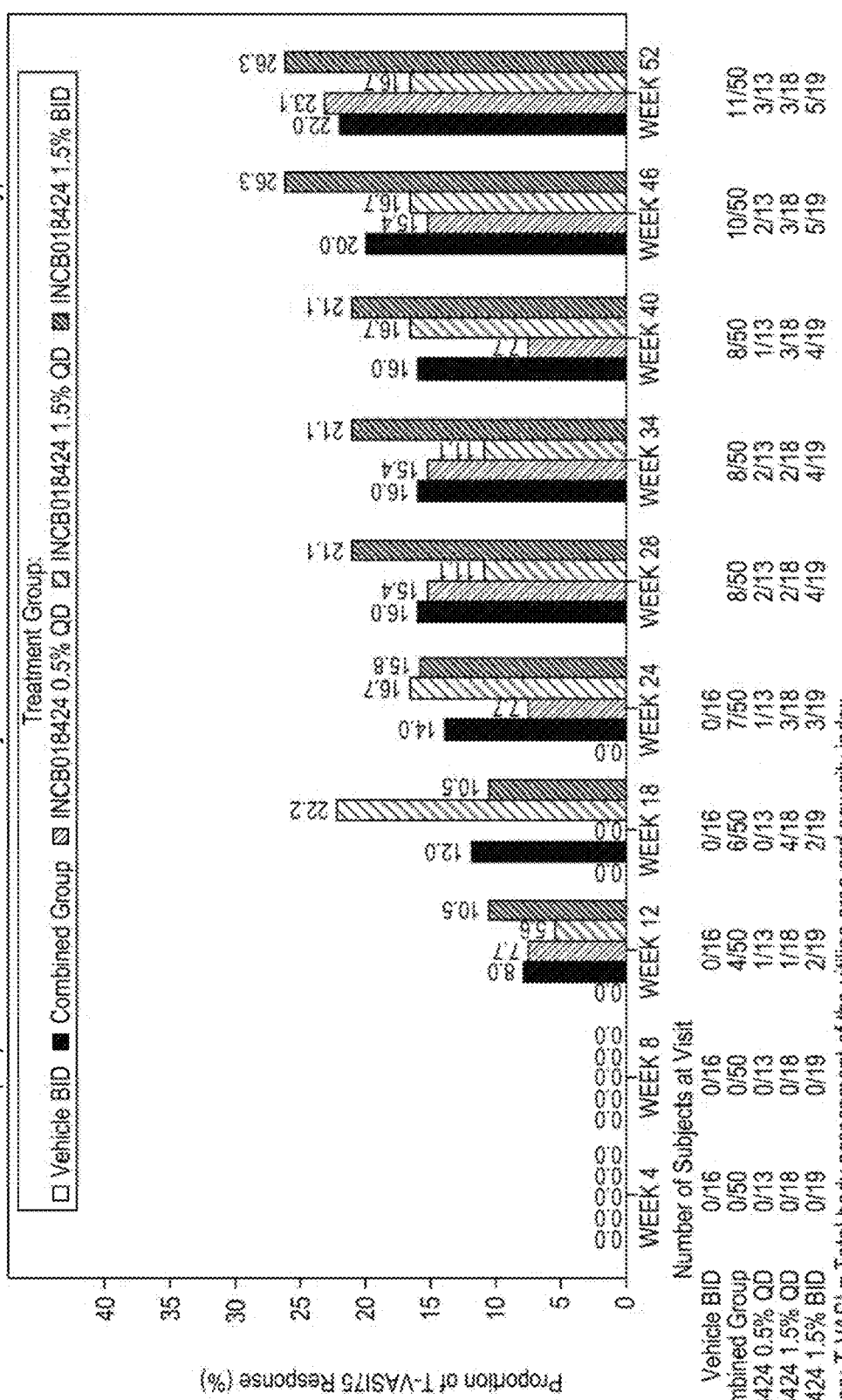
FIG. 45 is a graph depicting proportion of T-VASI75 response (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 46:
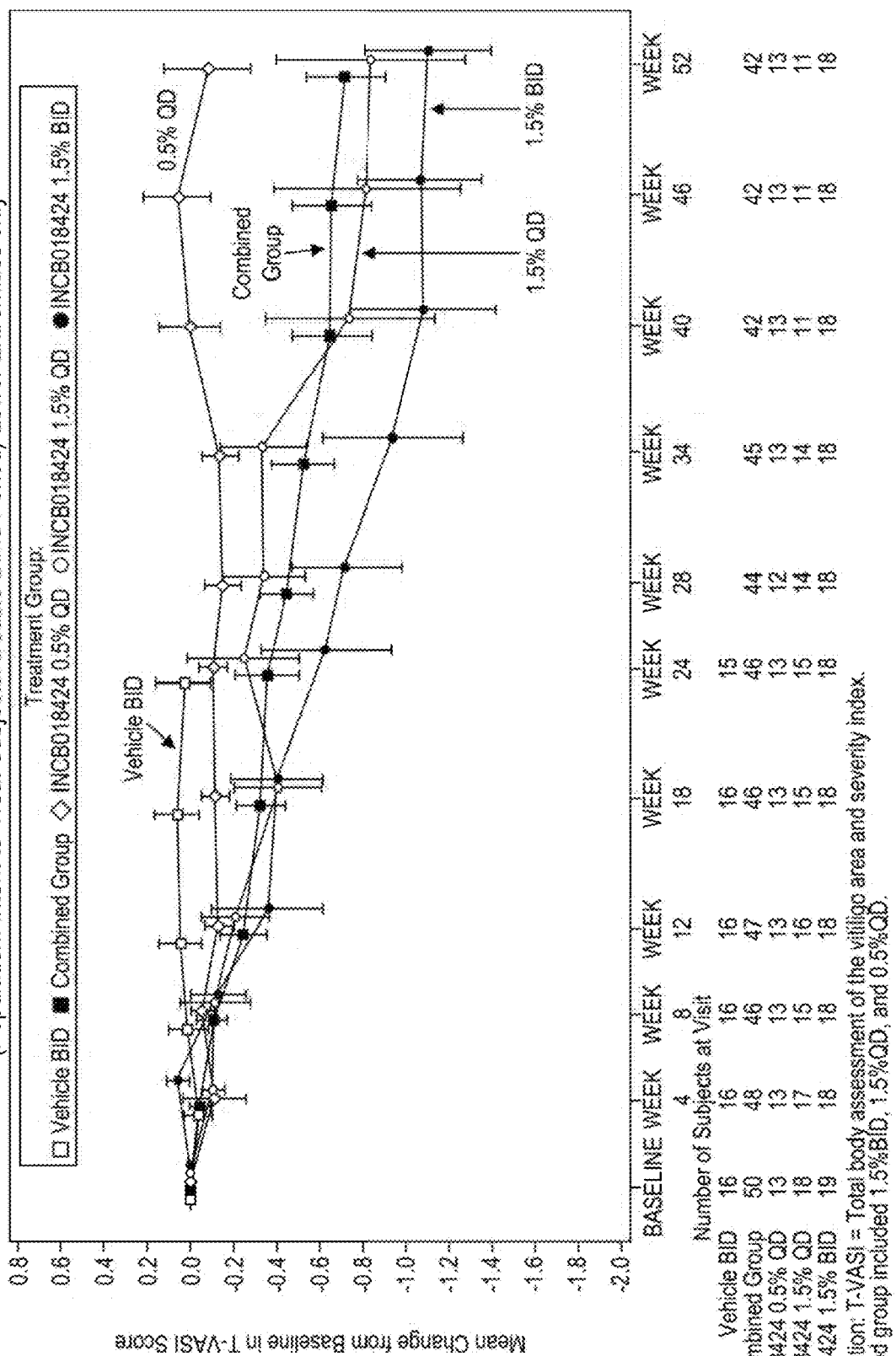
FIG. 46 is a graph depicting mean change from baseline in T-VASI score (trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 47:
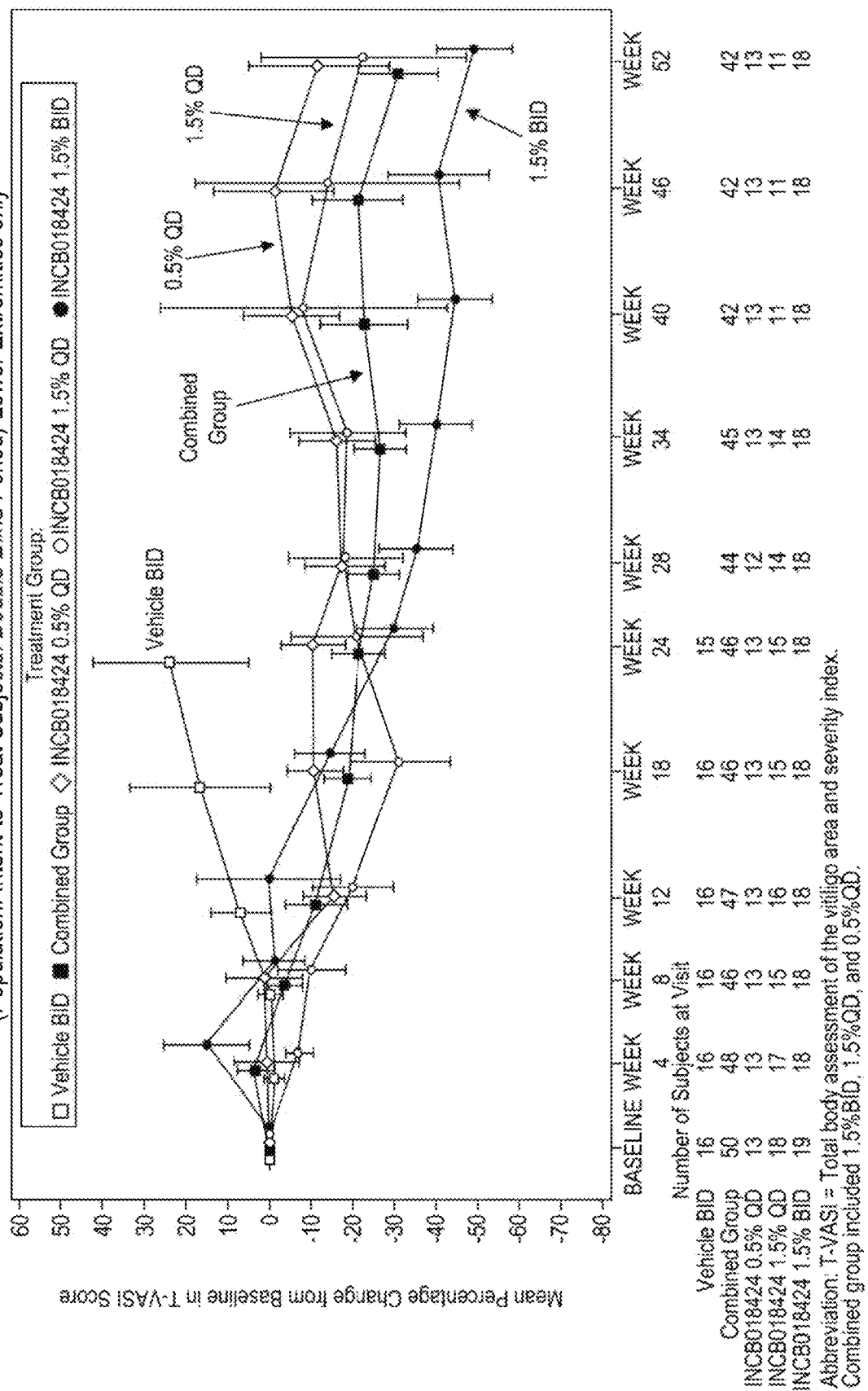
FIG. 47 is a graph depicting mean percentage change from baseline in T-VASI score trunk only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 54:
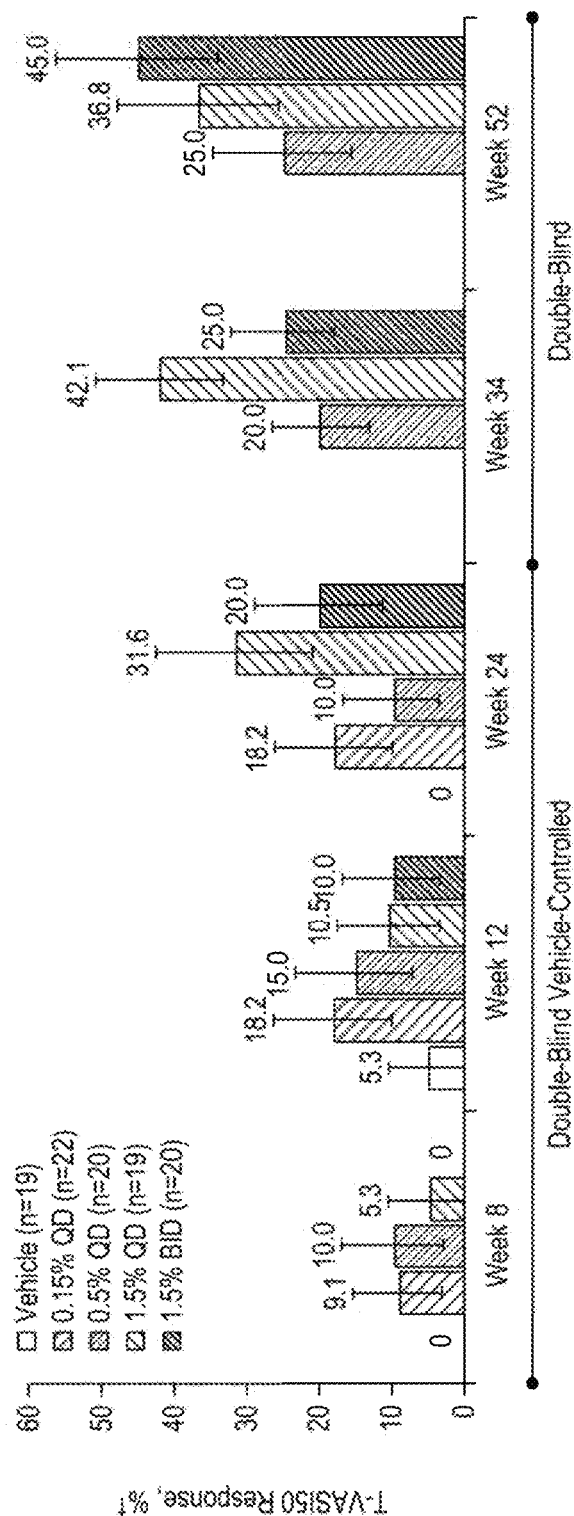
FIG. 54 is a graph depicting T-VASI50 response for patients who treated all depigmented skin at Week 8, Week 12, Week 24, Week 34, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order). T-VASI50 response is reported for the subset of patients with baseline T-BSA≤20% because treatment was limited to lesions constituting≤20% of T-BSA.
Figure 55:
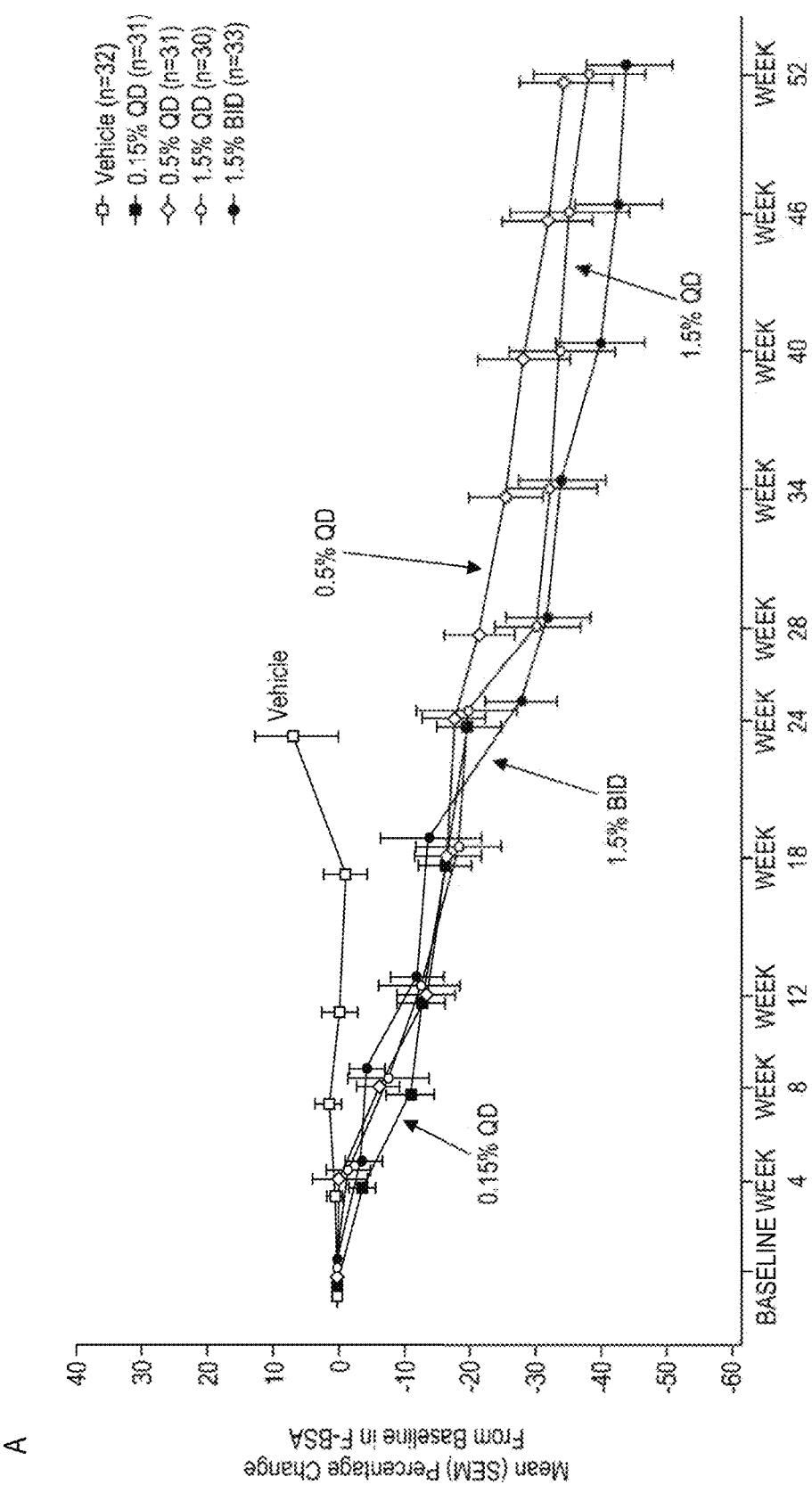
FIG. 55 is a graph depicting mean percentage change in F-BSA from baseline at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order).

Continuous improvement was achieved following 52 weeks of ruxolitinib cream monotherapy, with 1.5% BID producing the highest responses in F-VASI50 (57.6%), F-VASI75 (51.5%), and F-VASI90 (33.3%). (FIG. 5, FIG. 9, and FIG. 11). Among patients who treated all depigmented skin (baseline T-BSA≤20%), T-VASI50 response was 45.0% (1.5% BID) at Week 52 (FIG. 54). T-VASI50 at Week 52, a key secondary endpoint, was achieved by patients in a dose-dependent manner (FIGS. 17-1.5% BID, 36.4%; 1.5% QD, 30.0%; 0.5% QD, 25.8%). Mean percentage change from baseline in VASI (FIG. 14 (F-VASI) and FIG. 16 (T-VASI)) and BSA (FIG. 55 (F-BSA) and FIG. 22 (T-BSA)) showed clear separation from vehicle for face and total body starting as early as Week 8 of treatment with most ruxolitinib cream doses.

Figure 56:
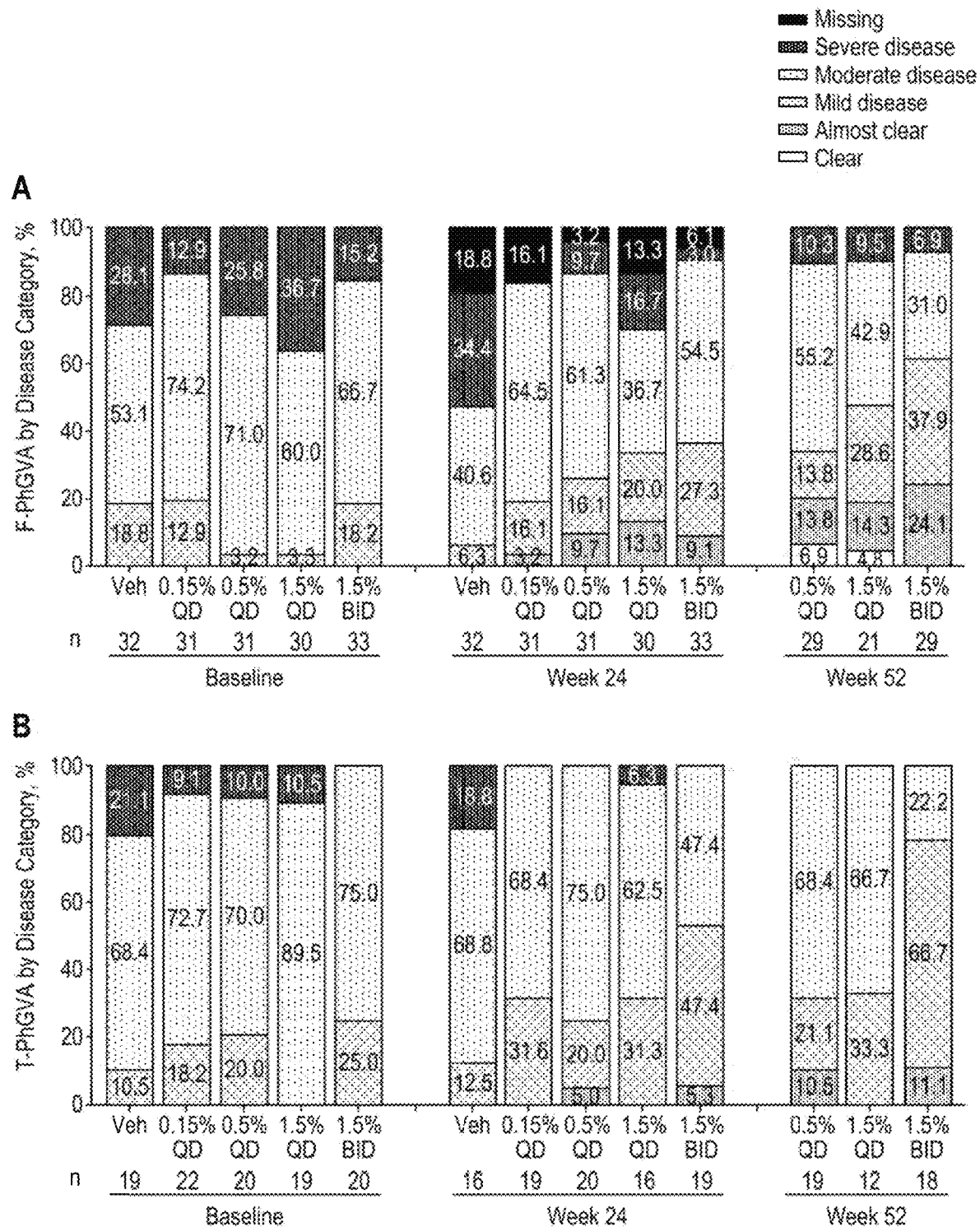
FIG. 56 depicts graphs of F-PhGVA (A) and T-PhGVA (B) by disease category at baseline, Week 24, and Week 52 for vehicle, 0.15% QD ruxolitinib cream, 0.5% QD ruxolitinib cream, 1.5% QD ruxolitinib cream, and 1.5% BID ruxolitinib cream. Bars are shown from bottom to top: Clear (C), Almost Clear (AC), Mild Disease (MiD), Moderate Disease (MoD), Severe Disease (SD), Missing (M). For A/baseline: veh, 0.15% QD, 0.5% QD, 1.5% QD, 1.5% BID (MiD, MOD, SD). For A/Week 24: vch (MiD, MOD, SD, M), 0.15% QD (AC, MiD, MOD. M), 0.5% QD, 1.5% QD, 1.5% BID (AC, MID, MOD, SD, M). For A/Week 52:0.5% QD, 1.5% QD (C, AC, MID, MOD, SD), 1.5% BID (AC, MiD, MOD, SD). For B/baseline: veh, 0.15% QD, 0.5% QD (MiD, MOD, SD), 1.5% QD (MOD, SD), 1.5% BID (MiD, MoD). For B/Week 24:15 veh, 1.5% QD (MiD, MOD, SD), 0.15% QD (MiD, MoD), 0.5% QD, 1.5% BID (AC, MID, MoD). For B/Week 52:0.5% QD, 1.5% BID (AC, MID, MOD), 1.5% QD (MiD, MoD).
Figure 57:
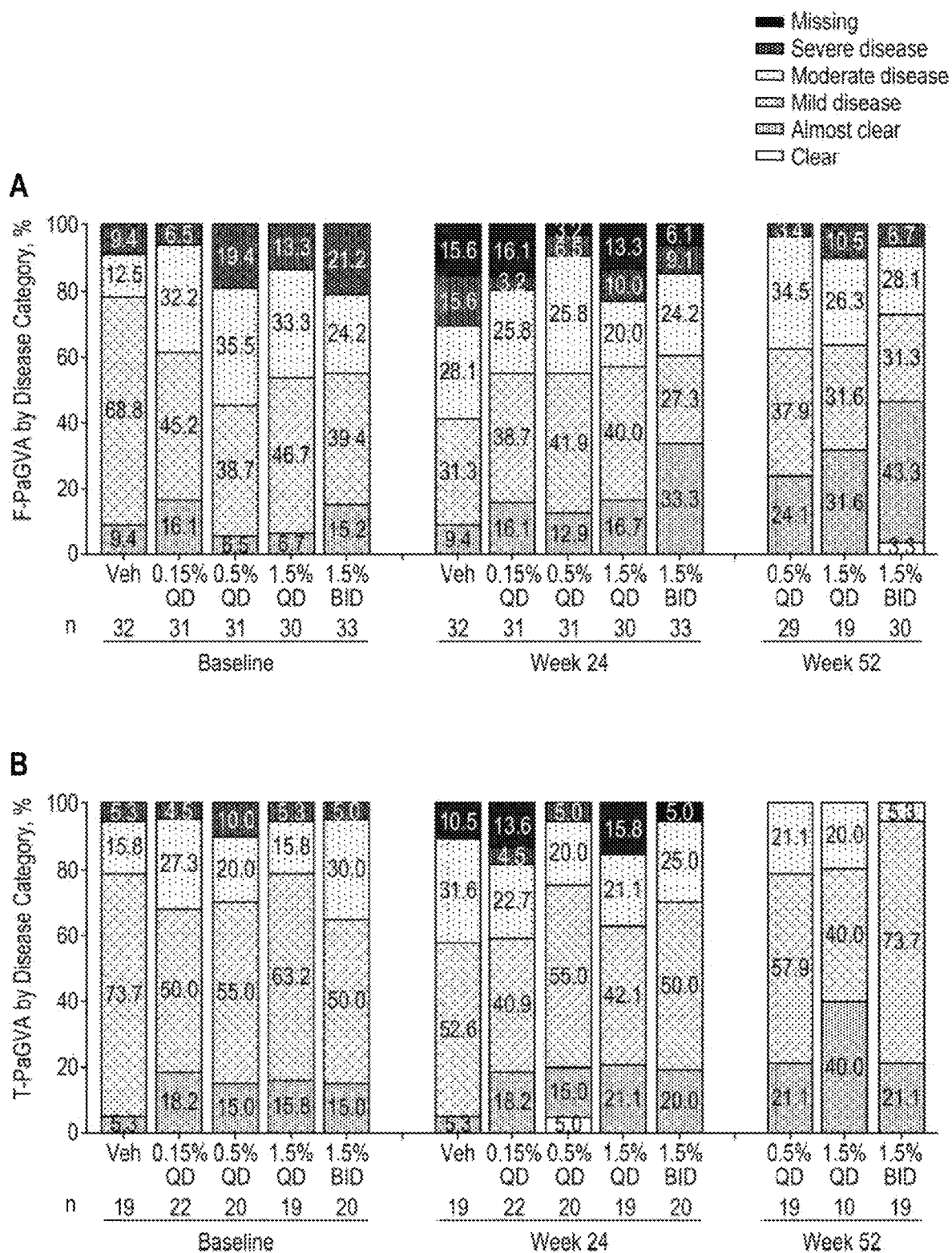
FIG. 57 depicts graphs of F-PaGVA (A) and T-PaGVA (B) by disease category at baseline, Week 24, and Week 52 for vehicle, 0.15% QD ruxolitinib cream, 0.5% QD ruxolitinib cream, 1.5% QD ruxolitinib cream, and 1.5% BID ruxolitinib cream. Bars are shown from bottom to top: No White Patches (NW), Mild (Mi), Moderate (Mo), Severe (S), Very Severe (VS), Missing (M). For A/baseline: veh, 0.15% QD, 0.5% QD, 1.5% QD, 1.5% BID (Mi, Mo, S, VS). For A/Week 24: veh, 0.15% QD, 0.5% QD, 1.5% QD, 1.5% BID (Mi, Mo, S, VS, M). For A/Week 52:0.5% QD, 1.5% QD (Mi, Mo, S. VS), 1.5% BID (NW, Mi, Mo, S, VS). For B/baseline: veh, 0.15% QD, 0.5% QD, 1.5% QD, 1.5% BID (Mi, Mo, S, VS). For B/Week 24: veh, 1.5% QD, 1.5% BID (Mi, Mo, S, M), 0.15% QD (Mi, Mo, S, VS, M), 0.5% QD (NW, Mi, Mo, S, VS). For B/Week 52:0.5% QD, 1.5% QD, 1.5% BID (Mi, Mo, S).
Figure 58:
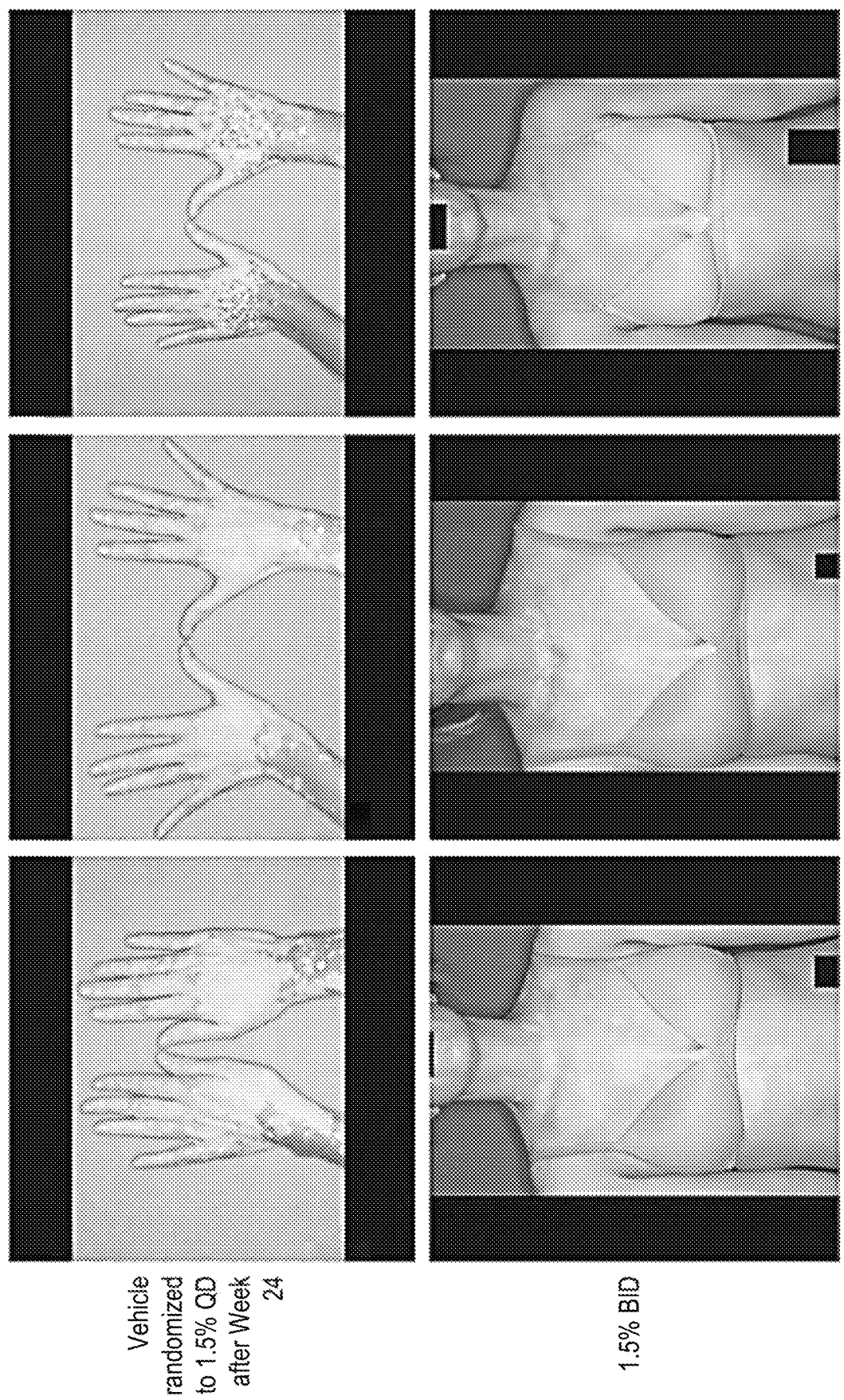
FIG. 58 depicts representative clinical images of patients at Day 1, Week 24, and Week 52 (left to right) for hands (top) and trunk (bottom).
Figure 60:
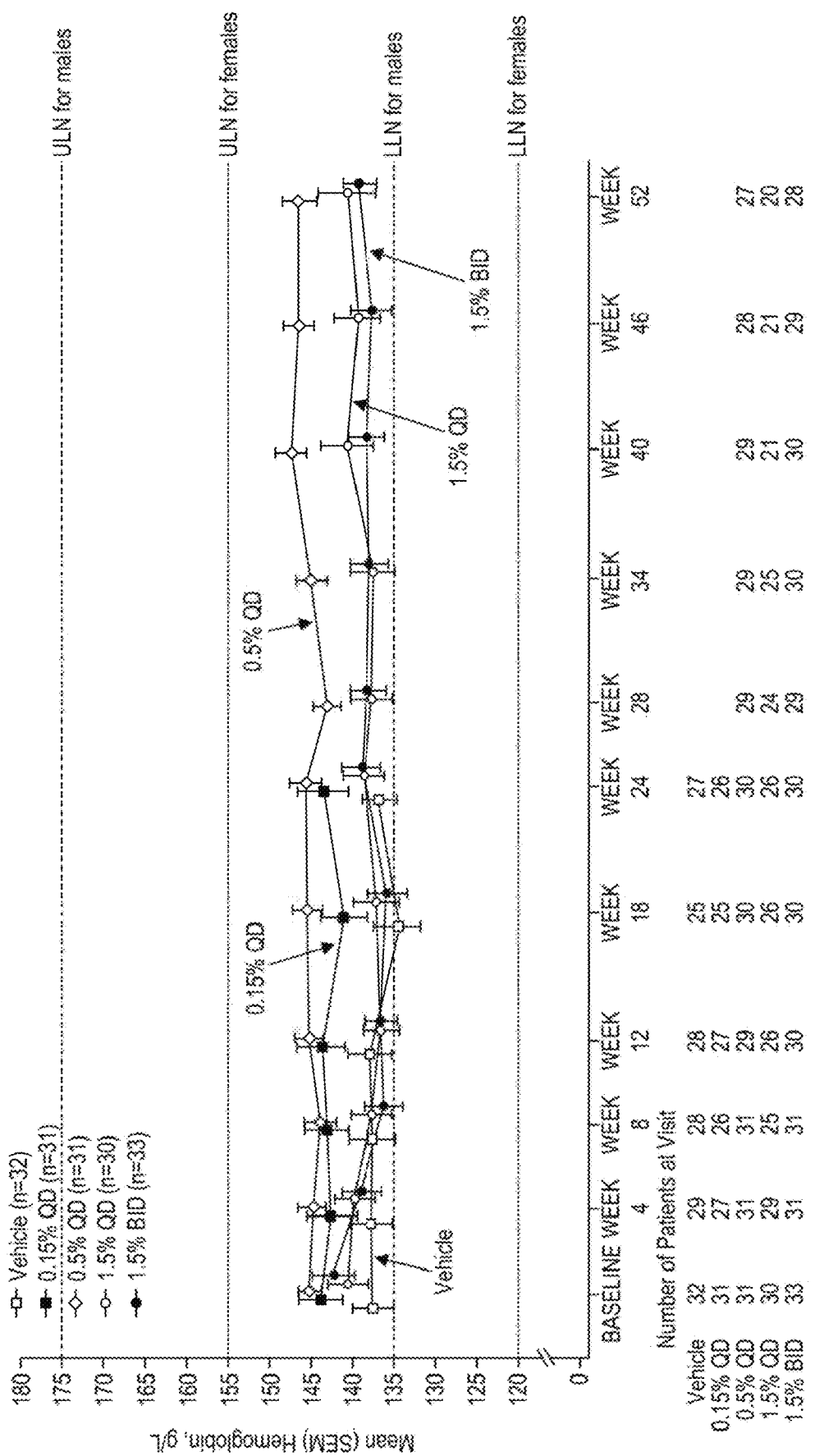
FIG. 60 is a graph depicting mean hemoglobin (g/L) at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream. At Week 52, top line is 0.5% QD, middle line is 1.5% QD and bottom line is 1.5% BID.
Figure 61:
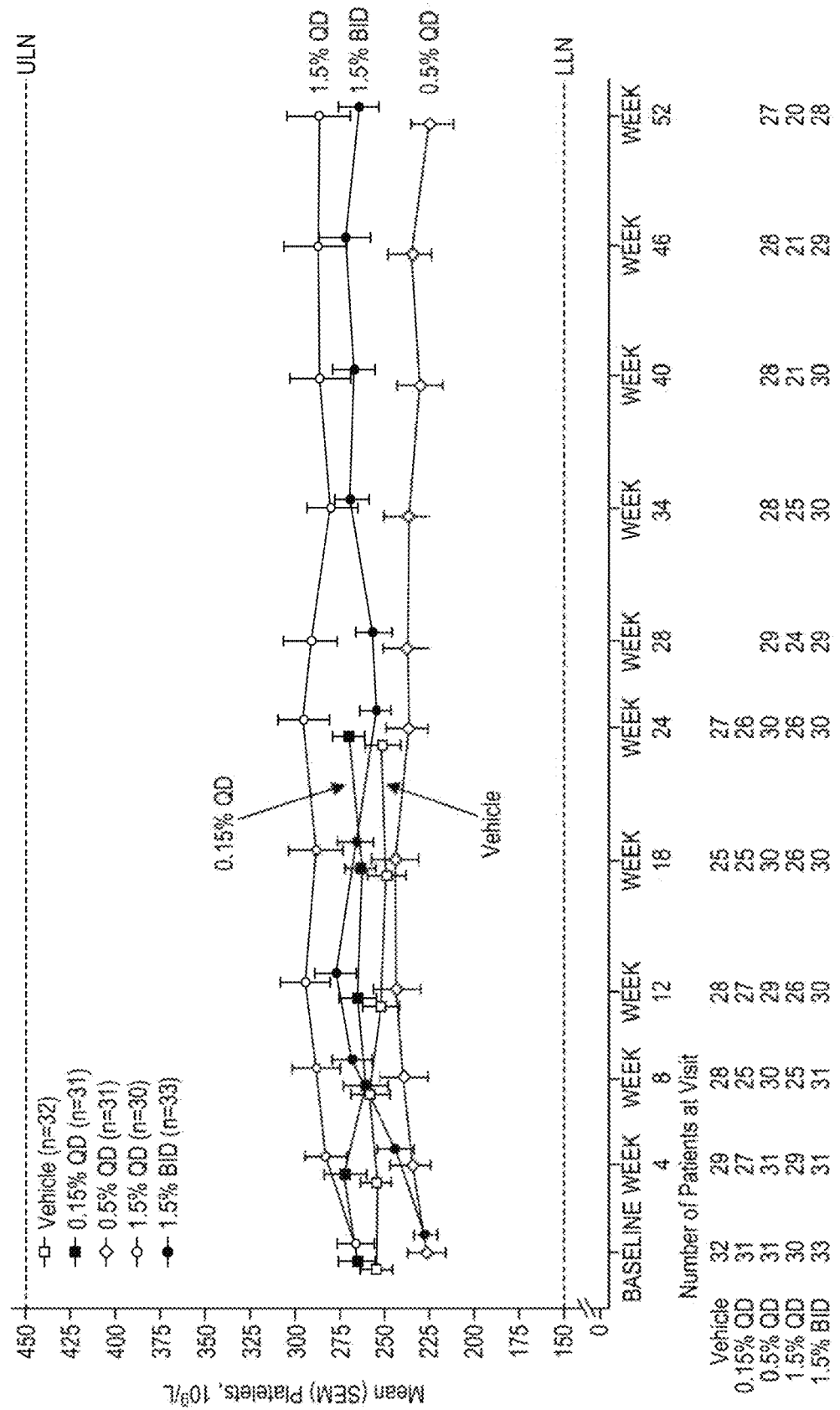
FIG. 61 is a graph depicting mean platelets ($10^9$/L) at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream. At Week 52, top line is 1.5% QD, middle line is 1.5% BID and bottom line is 0.5% QD.

Responses for F-VASI75 and F-VASI90 approximate desired patient outcomes of complete or near-complete repigmentation (Eleftheriadou, et al., Br J Dermatol 2019; 180:574-9); these responses paralleled improvements in PhGVA and PaGVA scores at Week 52. At Week 52, more patients had clear to mild disease versus baseline per F-PhGVA and T-PhGVA assessments (FIG. 56). Similarly, more patients reported mild disease or no white patches per F-PaGVA and T-PaGVA after 52 weeks of treatment with ruxolitinib cream versus baseline (FIG. 57). Patients who received any dose of ruxolitinib cream showed visible improvement in repigmentation of facial and nonfacial vitiligo lesions; repigmentation was most notable with 1.5% QD and 1.5% BID, and patients showed continued improvement through Week 52 (FIG. 58, showing trunk and hands).

Figure 48:
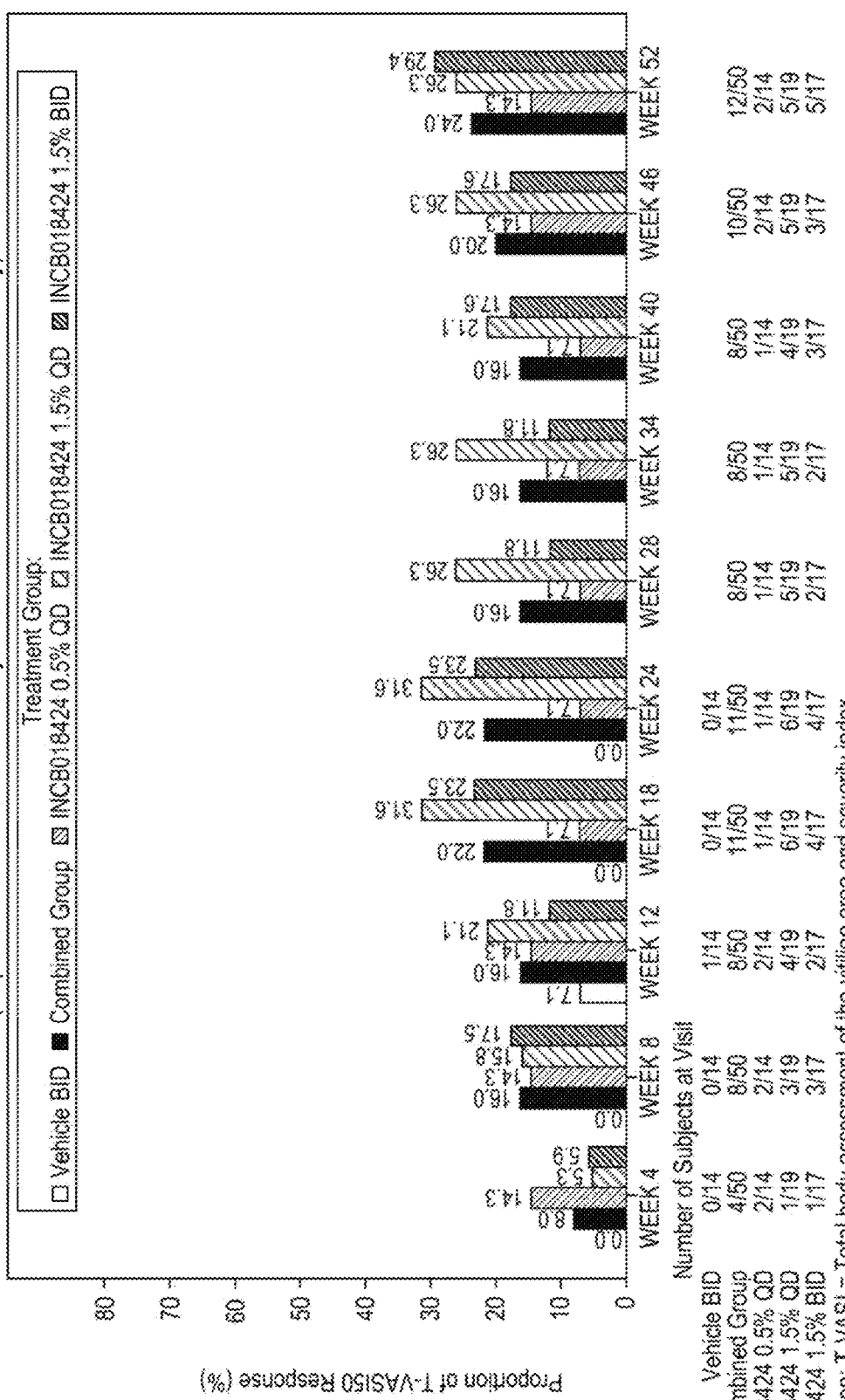
FIG. 48 is a graph depicting proportion of T-VASI50 response (feet only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 49:
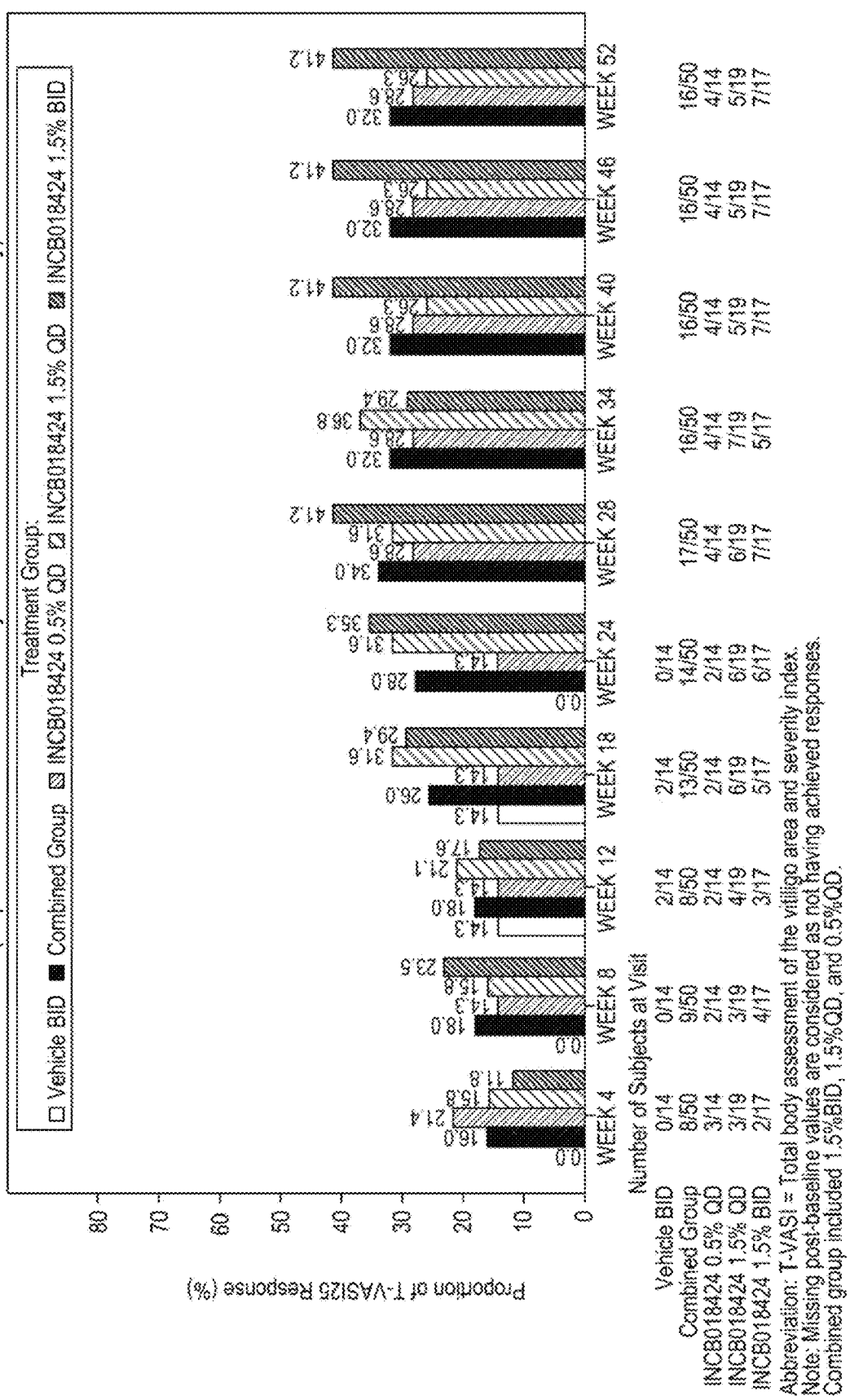
FIG. 49 is a graph depicting proportion of T-VASI25 response (feet only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 50:
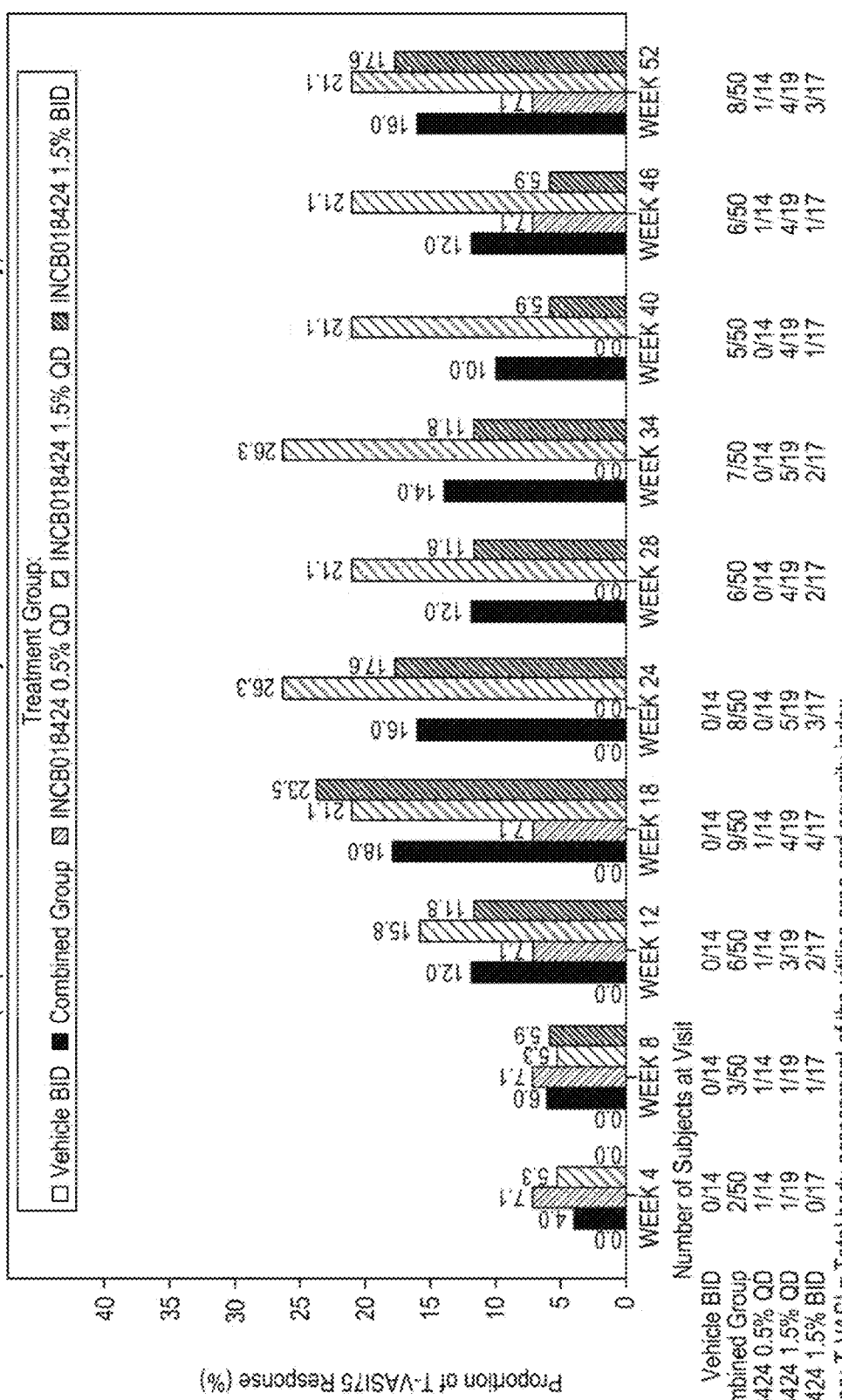
FIG. 50 is a graph depicting proportion of T-VASI75 response (feet only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 51:
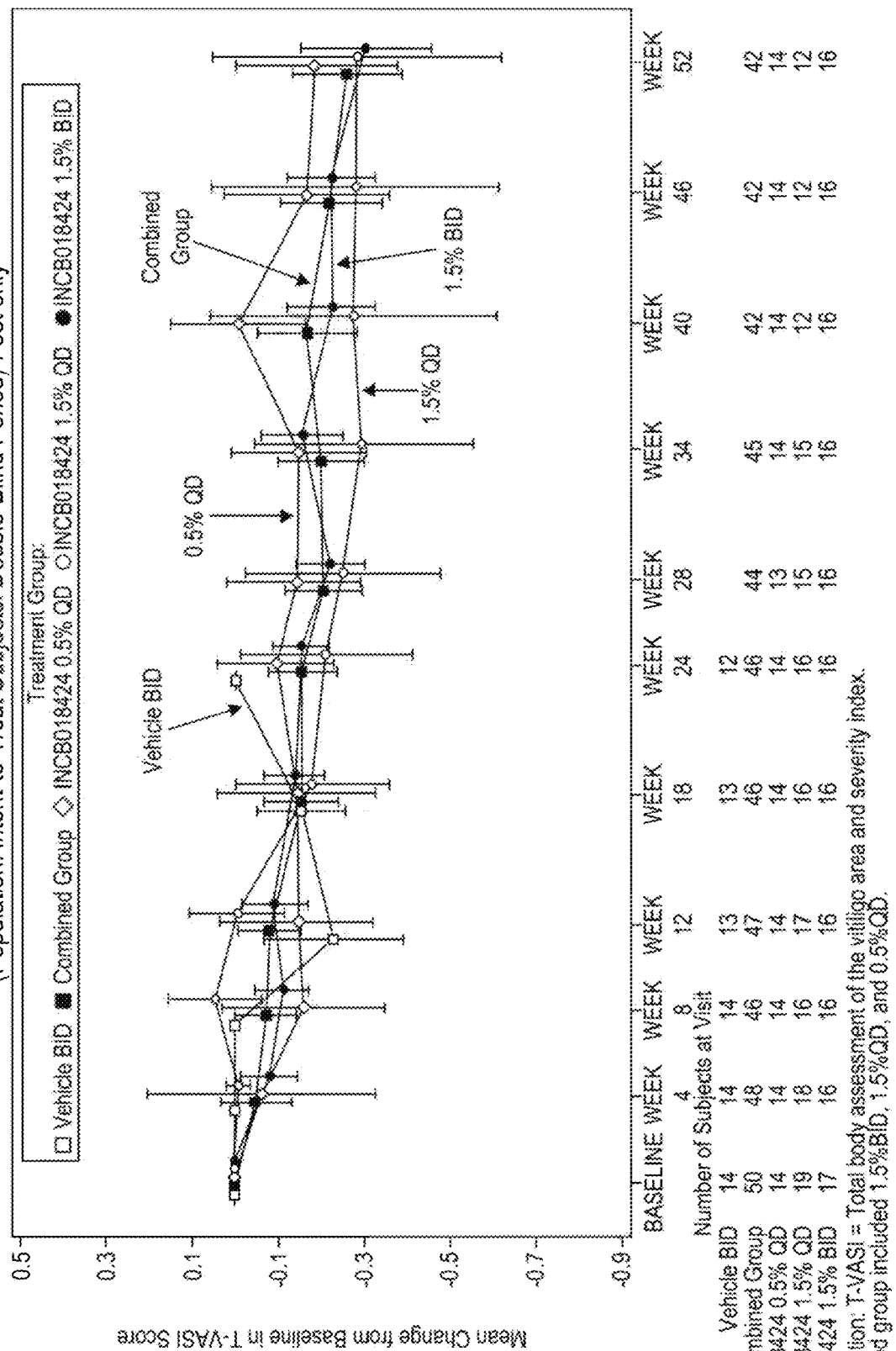
FIG. 51 is a graph depicting mean change from baseline in T-VASI score (feet only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.
Figure 52:
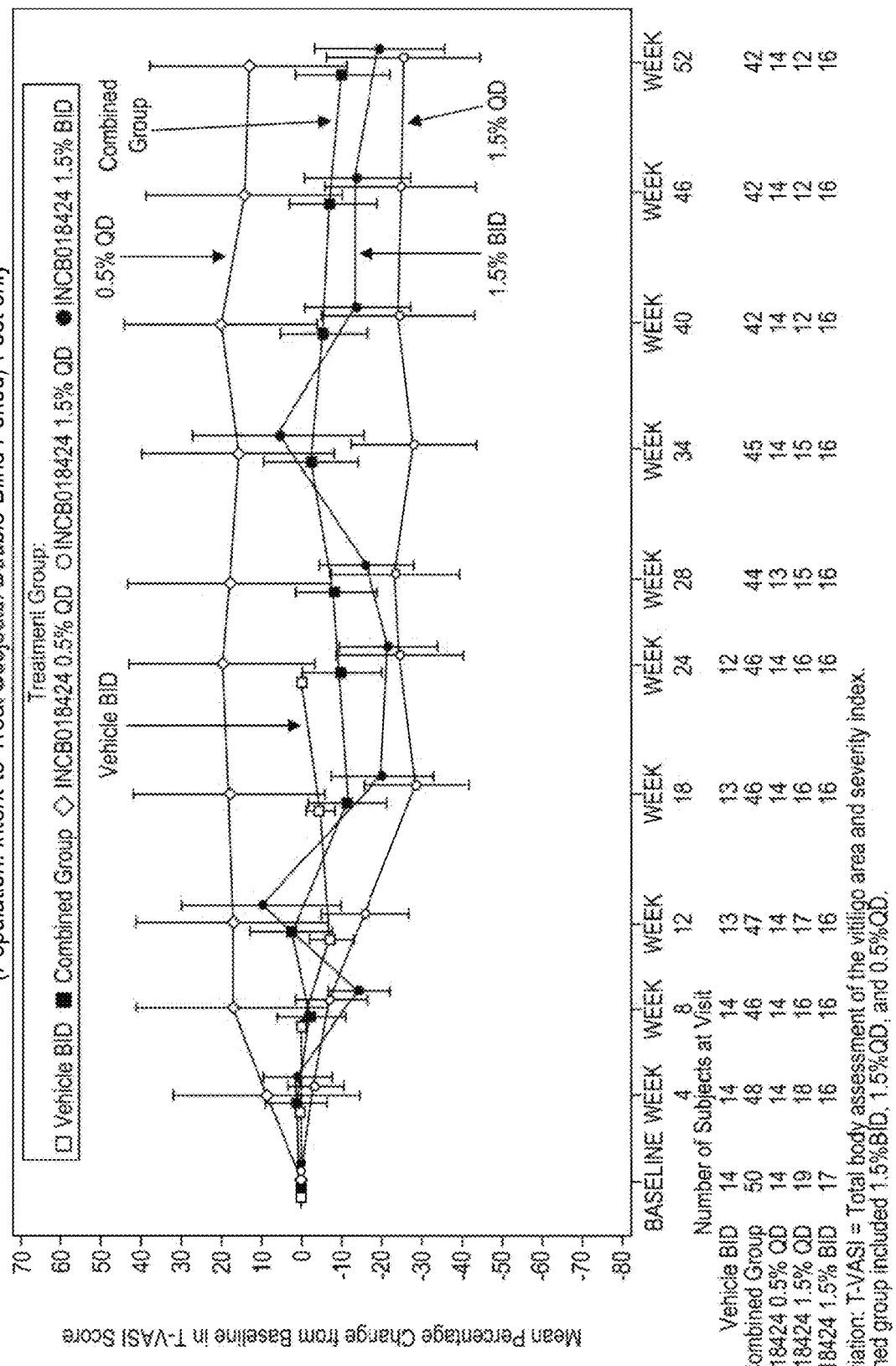
FIG. 52 is a graph depicting mean percentage change from baseline in T-VASI score (feet only) by visit and treatment group at baseline, Week 4, Week 8, Week 12, Week 18, Week 24, Week 28, Week 34, Week 40, Week 46, and Week 52 for vehicle, 0.15% QD ruxolitinib cream, 0.5% QD ruxolitinib cream, 1.5% QD ruxolitinib cream, and 1.5% BID ruxolitinib cream (bars for each group shown consecutive order) for the intent-to-treat subjects population in the double blind period.

Subgroup analysis determined the proportion of patients achieving ≥50% and ≥75% improvement from baseline in total Vitiligo Area Scoring Index (T-VASI50 and T VASI75) at Week 52 by affected body area. Ruxolitinib cream application was limited to ≤20% of total BSA, and analyses were conducted only in these patients. Ruxolitinib cream 1.5% BID produced the highest response in most body areas. At Week 52, 1.5% BID produced substantial overall T-VASI50 and T-VASI75 responses (45.0% and 15.0%) across all body regions: head/neck (60.0% and 55.0%) (FIGS. 24 and 25), trunk (29.4% and 11.8%) (FIGS. 39 and 40), upper extremities (52.9% and 23.5%) (FIGS. 34 and 35), lower extremities (52.6% and 26.3%) (FIGS. 43 and 45), hands (15.0% and 5.0%) (FIGS. 29 and 30), and feet (29.4% and 17.6%) (FIGS. 48 and 50). In summary, ruxolitinib cream produced repigmentation of all body areas in patients with vitiligo, including the hands/feet, which has not been reported with previous treatment modalities.

Out of 157 subjects, there were 11 patients with segmental vitiligo. Four of the patients were administered either 0.5% QD or 1.5% BID ruxolitinib cream. The two patients receiving 1.5% ruxolitinib cream were found to achieve F-VASI75 and T-VASI50 at Week 52 (Table 4).

TABLE 4

| | | F-VASI | | | T-VASI | |
|---|---|---|---|---|---|---|
| Subject | Group | % change from baseline (Week 24) | % change from baseline (Week 52) | F-VASI75 | % change from baseline (Week 52) | T-VASI50 |
| 1 | 1.5% BID | 0.00 | 94.44 | Y | 61.28 | Y |
| 2 | 1.5% BID | 75.00 | 95.00 | Y | 54.32 | Y |
| 3 | 0.5% QD | 33.33 | 33.33 | N | −13.45 | N |
| 4 | 0.5% QD | 0.00 | 16.00 | N | 5.69 | N |

Rates and types of treatment-emergent AEs (TEAEs) were similar across treatment groups (FIG. 59). Four patients experienced serious TEAEs (1.5% BID, subdural hematoma [n=1]; 1.5% QD, seizure [n=1]; 0.5% QD, coronary artery occlusion [n=1] and esophageal achalasia [n=1]) unrelated to study treatment. Application site pruritus was the most common treatment-related AE among patients treated with ruxolitinib cream (1.5% BID, n=1 [3.0%]; 1.5% QD, n=3 [10.0%]; 0.5% QD, n=3 [9.7%]; 0.15% QD, n=6 [19.4%]) and vehicle (n=3 [9.4%]; FIG. 59). Acne was noted as a treatment-related AE in 13 patients (8.3%) who received ruxolitinib cream and in 1 patient (3.1%) who received vehicle. All treatment-related AEs were mild (grade 1) or moderate (grade 2) in severity. Three patients experienced a TEAE leading to treatment discontinuation (0.15% QD and vehicle [both n=1], headache [related to treatment for 0.15% QD]; 1.5% QD [n=1], seizure).

There were no clinically relevant changes in laboratory values. Transient shifts within the normal range in hemoglobin (FIG. 60) and platelet (FIG. 61) levels were observed throughout double-blind treatment. At Week 52, hemoglobin and platelet levels were generally similar to those observed at baseline. Ruxolitinib cream systemic exposure was limited, corresponding to approximately 4% to 5% of the topical dose applied.

Example 2—Phase III Study Regarding Treatment of Vitiligo with Ruxolitinib

A Phase III a randomized, vehicle-controlled study in adolescent and adult (≥12 years old) participants who have been diagnosed with non-segmental vitiligo who have depigmented area including at least >0.5% BSA on the face, ≥0.5 F-VASI, at least ≥3% BSA on nonfacial areas, and ≥3 T-VASI is being conducted. Total body (facial and nonfacial) vitiligo should not exceed 10% BSA. Participants will be randomized on ruxolitinib cream 1.5% BID or vehicle, stratified by age (≤40 or >40 years) and skin type (Fitzpatrick scale Type I and II vs Type III, IV, V, and VI) to receive study treatment for 24 weeks. The ruxolitinib in the cream formulation was present as ruxolitinib phosphate with the percentages as % w/w on a free base basis. The cream formulation was an oil-in-water cream formulation as described in Table 5 of U.S. Patent Publ. No. 2015/0250790, which is incorporated herein by reference in its entirety. Adolescents will make up at least 10% of the study population, and no more than 50% of participants will be greater than 40 years of age. In this study, the area of the face analyzed for F-VASI will include the area on the forehead to the original hairline, on the cheek to the jawline vertically to the jawline and laterally from the corner of the mouth to the tragus. The area of the face analyzed will not include surface area of the lips, scalp, cars, or neck but will include the nose and eyelids.

VASI is based on a composite estimate of the overall area of vitiligo patches at baseline and the degree of macular repigmentation within these patches over time. Facial VASI is measured by percentage of vitiligo involvement (% of BSA) and the degree of depigmentation. The percentage of BSA (hand unit) vitiligo involvement is estimated by the investigator using the Palmar Method (see Section 8.2.1). Hand unit is based on participant's hand size. Investigator uses his/her hand to mimic the participant's hand size to evaluate percentage of BSA vitiligo involvement. The degree of depigmentation for each vitiligo involvement site is determined and estimated to the nearest of the following percentages: 0, 10%, 25%, 50%, 75%, 90%, or 100%. At 100% depigmentation, no pigment is present; at 90%, specks of pigment are present; at 75%, the depigmented area exceeds the pigmented area; at 50%, the depigmented and pigmented area are equal; at 25%, the pigmented area exceeds the depigmented area; at 10%, only specks of depigmentation are present. The F-VASI is then derived by multiplying the values assessed for the vitiligo involvement by the percentage of affected skin for each site on the face and summing the values of all sites together (possible range 0-3).

Total body VASI is calculated using a formula that includes contributions from all body regions (possible range, 0 100).

VASI=Σ[hand units]×[Residual Depigmentation] all body sites

The body is divided into the following 6 separate and mutually exclusive sites: (1) head/neck, (2) hands, (3) upper extremities (excluding hands), (4) trunk. (5) lower extremities (excluding feet), and (6) feet. The percentage of vitiligo involvement is estimated in hand units (% of BSA) by the same investigator during the entire course of the study. Hand unit is based on participant's hand size. The investigator uses his/her hand to mimic the participant's hand size to evaluate % BSA vitiligo involvement. The degree of depigmentation for each body site is determined and estimated to the nearest of the following percentages: 0, 10%, 25%, 50%, 75%, 90%, or 100%. The T-VASI is then derived by multiplying the values assessed for the vitiligo involvement by the percentage of affected skin for each body site and summing the values of all body sites together (Hamzavi I, Jain H, McLean D, Shapiro J, Zeng H, Lui H. Parametric modeling of narrowband UV-B phototherapy for vitiligo using a novel quantitative tool: the Vitiligo Area Scoring Index. Arch Dermatol 2004; 140:677-683).

After completion of the Week 24 assessments, participants will be offered the opportunity to receive an additional 28 weeks of open-label extension treatment with ruxolitinib cream 1.5% BID. To be eligible, participants must have completed the baseline and Week 24 visit assessments, be compliant with study medication, and meet all inclusion/exclusion criteria with exceptions that there will be no required lower limit or upper limit to the % BSA and the exclusion criterion of no prior JAK inhibitor treatment is not applicable for participants who receive ruxolitinib cream in the first 24 week double-blinded vehicle control period. The treated area should not exceed 10% BSA or 20% BSA. On areas that are fully repigmented, the participants may stop applying study drug and continue to be observed. Approval to treat additional areas (new vitiligo areas or expansion of the existing vitiligo areas) may occur via telephone during the open-label extension period, although the investigator, at his/her discretion, may ask the participant to return for an unscheduled visit. Patients receiving laser or any kind of phototherapy, including tanning bed or intentional UV exposure, are excluded from the study. Also excluded are subjects who have no pigmented hair within any of the vitiligo areas on the face; subjects who have other forms of vitiligo (eg, segmental) or other differential diagnosis of vitiligo or other skin depigmentation disorders (eg, piebaldism, pityriasis alba, leprosy, postinflammatory hypopigmentation, progressive macule hypomelanosis, nevus anemicus, chemical leukoderma, and tinea versicolor); subjects who have used depigmentation treatments (eg, monobenzone) for past treatment of vitiligo or other pigmented areas; and subjects who use protocol-defined treatments within the indicated washout period before baseline.

The primary endpoint for the study is the proportion of participants achieving F-VASI75 at Week 24. Secondary endpoints include: the percentage change from baseline in F-BSA (facial body surface area) at Week 24; the proportion of participants achieving F-VASI50 at Week 24; the proportion of participants achieving F-VASI90 at Week 24; the proportion of participants achieving T-VASI50 at Week 24; the proportion of participants achieving F-VASI75 at Week 52; the proportion of participants achieving F-VASI90 at Week 52; the proportion of participants achieving T-VASI50 at Week 52; the proportion of participants achieving T-VASI75 at Week 52; and the proportion of patients achieving a Vitiligo Noticeability Scale (VNS) of 4 ("a lot less noticeable") or 5 ("no longer noticeable) at Week 24; number of treatment-emergent adverse events upto 56 Weeks including any adverse event either reported for the first time or worsening of a pre-existing event after first dose of study drug; proportion of participants achieving F-VASI25/50/75/90 upto 52 Weeks (≥25%/50%/75%/90% improvement from baseline in F-VASI score); percentage change from baseline in F-VASI upto 52 Weeks; percentage change from baseline in F-BSA upto 52 Weeks; percentage change from baseline in T-VASI upto 52 Weeks; percentage change from baseline in total body surface area (T-BSA) upto 52 Weeks; proportion of participants achieving T-VASI25/50/75/90 at 52 Weeks (≥25%/50%/75%/90% improvement in T-VASI); proportion of participants in each category of VNS at 52 Weeks; population-based (trough) plasma concentrations of ruxolitinib at Week 4; population-based (trough) plasma concentrations of ruxolitinib at Week 24; population-based (trough) plasma concentrations of ruxolitinib at Week 40. The studies will also track the frequency, duration and severity of adverse events associated with the use of ruxolitinib cream.

What is claimed is:

1. A method of treating nonsegmental vitiligo in a patient, comprising:
    topically administering to a depigmented skin area of the patient a pharmaceutical composition comprising about 1.5% w/w ruxolitinib, or a pharmaceutically acceptable salt thereof, on a free base basis, twice per day;
    wherein:
    the patient suffers from nonsegmental vitiligo with depigmented area of: (i) 0.5% or greater body surface area (BSA) on the face, (ii) 3% or greater BSA on non-facial areas, and (iii) not exceeding 10% BSA on total body area; and
    the patient achieves a 75% or greater improvement in total body Vitiligo Area Scoring Index (T-VASI75).

2. The method of claim 1, wherein the method does not comprise administering laser or phototherapy.

3. The method of claim 1, wherein the ruxolitinib, or the pharmaceutically acceptable salt thereof, is ruxolitinib phosphate.

4. The method of claim 1, wherein topically administering is for at least 24 weeks.

5. The method of claim 4, wherein the patient achieves a 75% or greater improvement in T-VASI75 at week 24.

6. The method of claim 1, wherein the administering is for at least 52 weeks.

7. The method of claim 6, wherein the patient achieves a 75% or greater improvement in T-VASI75 at week 52.

8. The method of claim 1, wherein the patient has been clinically diagnosed with vitiligo.

9. The method of claim 1, wherein the patient is aged 12 years or older.

10. The method of claim 1, wherein the pharmaceutical composition is an oil-in-water emulsion, which is a cream.

11. The method of claim 1, wherein topically administering is continued until the patient achieves a 75% or greater improvement in facial Vitiligo Area Scoring Index after 24 weeks of the administering.

12. The method of claim 1, wherein topically administering is continued until the patient achieves a 90% or greater improvement in facial Vitiligo Area Scoring Index after 24 weeks of the administering.

13. The method of claim 1, wherein topically administering is continued until the patient achieves a 75% or greater improvement in facial Vitiligo Area Scoring Index after 52 weeks of the administering.

14. The method of claim 1, wherein topically administering is continued until the patient achieves a 90% or greater improvement in facial Vitiligo Area Scoring Index after 52 weeks of the administering.

15. The method of claim 1, wherein the pharmaceutical composition is administered to a patient population.

* * * * *